US006207881B1

(12) United States Patent
Theologis et al.

(10) Patent No.: US 6,207,881 B1
(45) Date of Patent: Mar. 27, 2001

(54) CONTROL OF FRUIT RIPENING THROUGH GENETIC CONTROL OF ACC SYNTHASE SYNTHESIS

(75) Inventors: Athanasios Theologis, Los Altos Hills, CA (US); Takahido Sato, Tokyo (JP)

(73) Assignee: The United States of America as represented by the Department of Agriculture, Washington, DC (US)

( * ) Notice: Subject to any disclaimer, the term of this patent is extended or adjusted under 35 U.S.C. 154(b) by 0 days.

(21) Appl. No.: 08/378,313

(22) Filed: Jan. 25, 1995

Related U.S. Application Data

(63) Continuation of application No. 07/862,493, filed on Apr. 19, 1992, now abandoned, which is a continuation-in-part of application No. 07/579,896, filed on Sep. 10, 1990, now abandoned.

(51) Int. Cl.[7] .............................. A01H 5/00; C12N 5/14; C12N 15/29; C12N 15/52; C12N 15/82
(52) U.S. Cl. ....................... 800/298; 435/320.1; 435/419; 536/23.2; 536/23.6
(58) Field of Search ................................ 435/69.1, 320.1, 435/419, 468; 536/23.2, 23.6; 800/278, 283, 298

(56) References Cited

U.S. PATENT DOCUMENTS 5,034,323 * 7/1991 Jorgensen et al. ................. 435/172.3
5,107,065 * 4/1992 Shewmaker et al. ................ 800/205

FOREIGN PATENT DOCUMENTS

WO 91/01375  2/1991 (WO) .
WO 92/11371  7/1992 (WO) .

OTHER PUBLICATIONS

Tigchelair, et al. in Tomato & Pepper Production in the Tropics. International Symposium on Integrated Management Practices, 1989, pp. 123–136 (Griggs, et al., eds.).*
Guzman, et al (Jun. 1990) The Plant Cell 2:513–523.*
Napoli, et al (Apr. 1990) The Plant Cell 2:279–289.*
van der Krol, et al. (Apr. 1990) The Plant Cell 2:291–299.*
van der Krol, et al. (1990) Plant Molecular Biology 14:457, Abstract.*
van der Straeten, et al (Jun. 1990) Proc. Natl. Acad. Science USA 87:4859–4863.*
Nakajima, et al (1990) Plant Cell Physiol. 31(7):1021–1029.*
Benfey et al (Apr. 1989) Science 244:174–181.*
van der Straeten, et al. (1989) Eur J. Biochem. 182:639–647.*
Wallace et al (Nov. 1987) Methods in Enzymology 152:432–442.*
Bleecker, et al (Oct. 1986) Proc. Natl. Acad. Sci. USA 83:7755–7759.*
Helfman et al (1987) Methods in Enzymology 152:451–457.*
Sargent et al, ibid, pp. 423–432.*
Walbot et al., *Nature* 334:196–197 (1988).
Napoli et al., *Plant Cell* (1990) 2:279–289.
van der Krol et al., *Plant Cell* (1990) 2:291–299.
Goring et al.,*Proc. Natl. Acad. Sci.* (1991) 88:1770–1774.
Smith et al., *Mol. Gen. Genetics* (1990) 224:447–481.
Elkind et al., *Proc. Natl. Acad. Sci.* (1990) 87:9057–9061.
Cameron et al., *Nucleic Acids Research* (1991) 19:469–475.
Nakajima et al., *Plant Cell Physiol.* (1986) 27(6):969–980.
Mehta et al., *Proc. Natl. Acad. Sci.* (1988) 85:8810–8814.
Tsai et al.,*Arch. Biochem. Biophys.* (1988) 264(2):632–640.
Bleecker et al., *Proc. Natl. Acad. Sci.* (1986) 83:7755–7759.
Privalle et al., *Arch. Biochem. Biophys.* (1987) 253(2):333–340.
Satoh et al., *Plant Physiol.* (1988) 88:109–114.
Van Der Straeten et al., *Eur. J. Biochem.* (1989) 182:639–647.
Theologis, A., et al., *J. Cell Biochem.* (1989) Suppl. 13D, UCLA Symposia on Molecular and Cellular Biology, Mar. 27–Apr. 7, 1989, p. 241.
Sato, *Proc. Natl. Acad. Sci.* (1989) 86:6621–6625.
Theologis, A., et al., *J. Cell Biochem.* (1990) Suppl. 14E, UCLA Symposia on Molecular and Cellular Biology, Mar. 31–Apr. 22, 1990, p. 356.
Theologis, et al., *Horticultural Biotechnology* (1990) Wiley– Liss, Inc., pp. 237–246.
Theologis, et al., *Plant Gene Transfer* (1990) Alan R. Liss, Inc., pp. 289–299.
Peter et al., *Plant Molecular Biology 1990* conducted by the NATO Advanced Study Institute, May 14–23, 1990, Bavaria, Germany, 1 page total.
Huang et al., SCBA Third International Symposium & Workshop Jun. 24–30, 1990, p. 230.
Sato et al., *J. Biol. Chem.* (1991) 266(6):3752–3759.
Van Der Straeten et al., *Pro. Natl. Acad. Sci.* (1990) 87:4859–4863.
Nagai et al., *Methods in Enzymol.* (1987) 153:461–481.
Rosenberg et al., *Gene* (1987) 56:125–135.
Acaster et al., *Plat Physiol.* (1983) 72:139–145.
Boller et al., *Planta* (1979) 145:293–303.
Yu et al., *Arch. Biochem. Biophys.* (1979) 198(1):280–286.
McCormick et al., *Plant Cell Reports* (1986) 5:81–84.

* cited by examiner

*Primary Examiner*—Che S. Chereskin
(74) *Attorney, Agent, or Firm*—Morrison & Foerster LLP

(57) ABSTRACT

Recombinant materials for the production of tomato ACC synthase are disclosed.

8 Claims, 39 Drawing Sheets

```
caactttcaaATGGGGTTTCATCAAATCGACGAAAGGAACCAAGCTCTTC
           M  G  F  H  Q  I  D  E  R  N  Q  A  L
                                E  R  N  Q  A  L
TCTCGAAGATCGCCCTCGACGATGGCCATGGCGAGAACTCCCCGTATTTC      100
 L  S  K  I  A  L  D  D  G  H  G  E  N  S  P  Y  F
 L  S  K  I  A  L  D  D  G  H  G  E  N  S  P  Y  F ←—pACC7
GATGGGTGGAAAGCTTACGATAACGATCCGTTTCACCCTGAGAATAATCC
 D  G  W  K  A  Y  D  N  D  P  F  H  P  E  N  N  P
 D  G  W  K  A  Y  D  N  D  P  F  H  P  E  N  N  P
TTTGGGTGTTATTCAAATGGGTTTAGCAGAAAATCAGCTTTCCTTTGATA      200
  L  G  V  I  Q  M  G  L  A  E  N  Q  L  S  F  D
  L  G  V  I  Q  M  G  L  A  E  N  Q  L  S  F  D
TGATTGTTGACTGGATTAGAAAACACCCTGAAGCTTCGATTTGTACACCG
 M  I  V  D  W  I  R  K  H  P  E  A  S  I  C  T  P
 M  I  V  D  W  I  R  K  H  P  E  A  S  I  C
GAAGGACTTGAGAGATTCAAAAGCATTGCCAACTTCCAAGATTACCACGG      300
  E  G  L  E  R  F  K  S  I  A  N  F  Q  D  Y  H  G
CTTA CAGAGTTTCGAAATGCAATTGCAAATTTTATGGGGAAAGTAAGAG
   L  P  E  F  R  N  A  I  A  N  F  M  G  K  V  R
GTGGGAGGGTAAAATTCGACCCGAGTCGGATTGTGATGGGTGGCGGTGCG      400
 G  G  R  V  K  F  D  P  S  R  I  V  M  G  G  G  A
ACCGGAGCGAGCGAAACCGTCATCTTTTGTTTGGCGGATCCGGGGGATGC
 T  G  A  S  E  T  V  I  F  C  L  A  D  P  G  D  A
TTTTTTGGTTCCTTCTCCATATTATGCAGGATTTGATCGAGACTTGAAAT      500
    F  L  V  P  S  P  Y  Y  A  G  F  D  R  D  L  K
GGCGAACACGAGCACAAATAATTCGGGTCCATTGCAACGGCTCGAATAAC
 W  R  T  R  A  Q  I  I  R  V  H  C(N) G  S  N  N
TTCCAAGTCACAAAGGCAGCCTTAGAAATAGCCTACAAAAAGGCTCAAGA      600
  F  Q  V  T  K  A  A  L  E  I  A  Y  K  K  A  Q  E
GGCCAACATGAAAGTGAAGGGTGTTATAATCACCAATCCCTCAAATCCCT
   A  N  M  K  V  K  G  V  I  I  T  N  P  S  N  P
TAGGCACAACGTACGACCGTGACACTCTTAAAACCCTCGTCACCTTTGTG      700
  L  G  T  T  Y  D  R  D  T  L  K  T  L  V  T  F  V
AATCAACACGACATTCACTTAATATGCGATGAAATATACTCTGCCACTGT
  N  Q  H  D  I  H  L  I  C  D  E  I  Y  S  A  T  V
CTTCAAAGCCCCAACCTTCACCAGCATCGCTGAGATTGTTGAACAAATGG      800
  F  K  A  P  T  F  T  S  I  A  E  I  V  E  Q  M
```

FIG. 1B(i)

```
AGCATTGCAAGAAGGAGCTCATCCATATTCTTTATAGCTTGTCCAAAGAC
 E  H  C  K  K  E  L  I  H  I  L  Y  S  L  S  K  D
ATGGGCCTCCCTGGTTTTCGAGTTGGAATTATTTATTCTTACAACGATGT    900
 M  G  L  P  G  F  R  V  G  I  I  Y  S  Y  N  D  V
CGTCGTCCGCCGTGCTCGGCAGATGTCGAGCTTCGGCCTCGTCTCGTCCC
 V  V  R  R  A  R  Q  M  S  S  F  G  L  V  S  S
AGACTCAACATTTGCTCGCCGCCATGCTTTCCGACGAGGACTTTGTCGAC   1000
 Q  T  Q  H  L  L  A  A  M  L  S  D  E  D  F  V  D
AAATTTCTTGCCGAGAACTCGAAGCGTGTGGGCGAGAGGCATGCAAGGTT
 K  F  L  A  E  N  S  K  R  V  G  E  R  H  A  R  F
CACAAAAGAATTGGATAAAATGGGGATCACTTGCTTGAACAGCAATGCTG   1100
 T  K  E  L  D  K  M  G  I  T  C  L  N  S  N  A
GAGTTTTTGTGTGGATGGATCTACGGAGGCTATTAAAAGACCAAACCTTC
 G  V  F  V  W  M  D  L  R  R  L  L  K  D  Q  T  F
AAAGCTGAAATGGAGCTTTGGCGTGTGATTATCAATGAAGTCAAGCTCAA   1200
 K  A  E  M  E  L  W  R  V  I  I  N  E  V  K  L  N
TGTTTCTCCTGGCTCATCCTTTCATGTCACTGAGCCAGGTTGGTTTCGAG
 V  S  P  G  S  S  F  H  V  T  E  P  G  W  F  R
TTTGTTTCGCAAACATGGACGACAACACCGTTGACGTTGCTCTCAATAGA   1300
 V  C  F  A  N  M  D  D  N  T  V  D  V  A  L  N  R
ATCCATAGCTTTGTCGAAAACATCGACAAGAAGGAAGACAATACCGTTGC
 I  H  S  F  V  E  N  I  D  K  K  E  D  N  T  V  A
AATGCCATCGAAAACGAGGCATCGAGATAATAAGTTACGATTGAGCTTCT   1400
 M  P  S  K  T  R  H  R  D  N  K  L  R  L  S  F
CCTTCTCAGGGAGAAGATACGACGAGGGCAACGTTCTTAACTCACCGCAC
 S  F  S  G  R  R  Y  D  E  G  N  V  L  N  S  P  H
ACGATGTCGCCTCACTCGCCGTTAGTAATAGCAAAAAATTAAttaaaaac   1500
 T  M  S  P  H  S  P  L  V  I  A  K  N
attttcaaaatattcataccattcatatagtttttttttttttttttttt
tgggtcaatgttgactaaagttacgtatatttttccacagtggatatga    1600
tgtaaacttcatattttttggtgggatggtgatagatgtaatgtatttgg
ttttttcccttagggaactcatacttatttattaatgaaatgattgtgatt   1700
tat
```

FIG. 1B(ii)

```
            10        20        30        40
             .         .         .         .
                                                    cg
cattggttggagagagaggaacgagtgcaacgaggatgctgggctctgaa
aaggggtggattgtgagatcccacgaacgaaacattctttgtaagggtgt
gaaaacctctccctagcatactcgttttaaaaacctcaaggagaagtaca         -2501
aaaagaaaagccgaggaaggatttcaaaaagttagaacttcattaaaaat
gaaagcacaaagaagagaattattagtaatgttcttgcacaagtataagt
tgaaaaactaattctatcaagtgtgaatccacactcatctttcaaaatta
agcaaacaaaacgagtcatgcttgccttctccaaattttatcactaatag
tgtgacactcaatgtcccacttaccattcttggcccccacaaccacctcc
aagaaacaataacttttactacccaaccccaattttggaacaaaaatga
gtcaaatatatgaacaataacatcgtgtttcttcttaccgactcggttga
atatgcaacgtttataatatacttcaagaaattttgagacattactcaaa
taaagtctctcacaaaaatagaatatctttatactagtataatgaattgt
ccacttcgatttaaatcctctaaagttcactttcgtaaatggcttaatga        -2001
acagatttattaggatcaaattcaaaagttgaatgagactaaatagatat
aataaaatctgattgttgcatgaagtatgcagctcaaagatgatgttttg
cgaaaaaaatgcaaactaagcatgagtgcttctgtaaaaaaaaaatgaaa
aagaaaaatatatatcgtactatcaaaaacattgtccttacttagacagc
tcaaaacttttcatattcctatatttgtttatattgaaactttttccatt
tcatttgtttaaatcatatttggttgtttaaataagaatactgtaacagt
ccaagctcactgttagtagatattgtcttcttcggacttttccggcttct
tctcaaggttttaaaatgtgtctactagggagagattttcacacacttat
aaagaatgattcgttctcctcttcaactaatgtaaaatctcacaaatact
aaacaattggaatttattaggatcagaatcaaaagttgagagatatagtg        -1501
gaaacgaccgtcgagattaaatagatacaatcaagtttgatcattgtact
aaataagtagctcggagatgtatacgagaaaagaaagcgcactataaaaa
tgaggtaaaaagtggtcggagtagtatacaatgtgagaggtatgcaaata
tacgtatttcctttaggtgaaaaagtccgaaaccacaccaaaaagcactc
ttaaaaatgtgccaaaacggttctatcactcaatgtcaaatctttcaatt
caaaagcatgtgggtattgattgctgcttccaacgaagcttcattctcct
acttgttacacacacacaaactcgttgttcatgaccaattctatcccctt
tcccatgtcatcctccaaacttttgacccttcaatttggtcccctaaccc
ttttttttcatcacatgggatgcaaccattttgatttagtctacgacattc
ttttcatttatctacttacgccctccgagggaacagttggattgaaagtt        -1001
cgacttcttagccttggagatgagagaaccggtacactccatgaattaca
aaatttaaatctctaatcctaactttggagctacgtatgacctttgtatc
```

FIG. 3A

```
tttgtaagagcttttctcaatgctaacaaatattgtctatttcagctggt
tacgcattgtcgtctgcttcccgattttaaaatacgtctattaaggagag
gttttcacacccttactagaaacgtttcgttctccctcaaatgtgagat
ctcaccgtaactagctagagattaaaatgttattatagctagagattcaa
ccaaacataacacaaaaagataatcatagggatcaacaaaattcataact
agttcttataatatgcaataaaattcaaattaattatgcattagaagaaa
ataaaaaaacaattaagataacccaaaaattaatttccttctacctataa
atctataataagattcgagtattagattaaaattatcccaaatcaagaac          -501
ataaattaagatcataaacgtaatatattttaatcgagaacgtaaataca
ggacatacagattaagaattcaaatattttgaattataatatgaatttga
tagaaaataaaacaaaaactaaaaaataaacttagtaattatgatgagat
aaaagaagattttgtgacatgatattttgttatgttccaaatctagagt
atgcctccacacatgcggggtcgggtcggctgtgtgtgtggctcgtctgc
ttgcttgaatcacaaccctccacgcatgcaattacgccctccttgactca
aaccccattttaactctctcttccattttattattttttctttaattt
tttcatcactgtttttttttttttttttttcatggtttgaactttgaaa
agttgaattttctacacgtttgattttcctggtaagaacttgatcttgtt
ggatcttcctcactgcttataaattcactcaattctcttctttctttcct          -1
ATCTTACAACCCAAAACCTCTCATTTTTAGGCACATCTCAACAACTTTCA
AATGGGGTTTCATCAAATCGACGAAAGGAACCAAGCTCTTCTCTCGAAGA           100
    M  G  F  H  Q  I  D  E  R  N  Q  A  L  L  S  K
TCGCCCTCGACGATGGCCATGGCGAGAACTCCCCGTATTTCGATGGGTGG
   I  A  L  D  D  G  H  G  E  N  S  P  Y  F  D  G  W
AAAGCTTACGATAACGATCCGTTTCACCCTGAGAATAATCCTTTGGGTGT
   K  A  Y  D  N  D  P  F  H  P  E  N  N  P  L  G  V
TATTCAAATGGGTTTAGCAGAAAATCAGgtttggtatatcgtgttttcgt
   I  Q  M  G  L  A  E  N  Q
gttttcttatatgacttcacgtttgaaaatttcgctaactttgtttttt
tgtgaatttcgatagCTTTCCTTTGATATGATTGTTGACTGGATTAGAAA
                 L  S  F  D  M  I  V  D  W  I  R  K
ACACCCTGAAGCTTCGATTTGTACACCGGAAGGACTTGAGAGATTCAAAA
   N  P  E  A  S  I  C  T  P  E  G  L  E  R  F  K
GCATTGCCAACTTCCAAGATTACCACGGCTTACCAGAGTTTCGAAATgta
   S  I  A  N  F  Q  D  Y  H  G  L  P  E  F  R  N
```

FIG. 3B

```
cgagatatgatatactcttaactatatctgaactcaaaaggttaagttga           500
tgggttatgataaaatttctttcttgtcagGCAATTGCAAATTTTATGGG
                              A  I  A  M  F  M  G
GAAAGTAAGAGGTGGGAGGGTAAAATTCGACCCGAGTCGGATTGTGATGG
 K  V  R  G  G  R  V  K  F  D  P  S  R  I  V  M
GTGGCGGTGCGACCGGAGCGAGCGAAACCGTCATCTTTTGTTTGGCGGAT
 G  G  A  T  G  A  S  E  T  V  I  F  C  L  A  D
CCGGGGGATGCTTTTTTGGTTCCTTCTCCATATTATGCAGGgtgagttct
 P  G  D  A  F  L  V  P  S  P  Y  Y  A  G
tctttcatttccttttgttcactttttctttaagtcaatattccttagtcc
aacctggaaagagaaagaagagagagaaagaaaccatttgacaaattaat
aactctacaaattctctttgaaagtttgatgttttttttaaggtcaaaac
ttcaaccattctcttgcaaagaaaaaaaaaagtcataattataatgaaga
aaaaactaggccatccaagtcaaccttttttaaatgctaataaagtcaata
tgctttgtaggtttaaaaaacaataaaattgcttaatcatttcttaaattt     1000
taattaaaccccttttgactttatcattacccatttacataaattaacaat
ttattgctcttttttgtagtaaaattaataaaaaaaaagttaggtgtaaaac
gtacagtattatgttattgtaaaaatactgagaagtgttagtatgttgtt
tttcagATTTGATCGAGACTTGAAATGGCGAACACGAGCACAAATAATTC
       F  D  R  D  L  K  W  R  T  A  Q  I  I
GGGTCCATTGCAACCGCTCGAATAACTTCCAAGTCACAAAGGCAGCCTTA
 R  V  H  C  N  R  S  N  N  F  Q  V  T  K  A  A  L
GAAATAGCCTACAAAAAGGCTCAAGAGGCCAACATGAAAGTGAAGGGTGT
 E  I  A  Y  K  K  A  Q  E  A  N  M  K  V  K  G  V
TATAATCACCAATCCCTCAAATCCCTTAGGCACAACGTACGACCGTGACA
 I  I  T  N  P  S  N  P  L  G  T  T  Y  D  R  D
CTCTTAAAACCCTCGTCACCTTTGTGAATCAACACGACATTCACTTAATA
 L  K  T  L  V  T  F  V  N  Q  H  D  I  H  L  I
TGCGATGAAATATACTCTGCCACTGTCTTCAAAGCCCCAACCTTCACCAG
 C  D  E  I  Y  S  A  T  V  F  K  A  P  T  F  T  S
CATCGCTGAGATTGTTGAACAAATGGAGCATTGCAAGAAGGAGCTCATCC     1500
 I  A  E  I  V  E  Q  M  E  H  C  K  K  E  L  I
ATATTCTTTATAGCTTGTCCAAAGACATGGGCCTCCCTGGTTTTCGAGTT
 H  I  L  Y  S  L  S  K  D  M  G  L  P  G  F  R  V
GGAATTATTTATTCTTACAACGATGTCGTCGTCCGCCGTGCTCGGCAGAT
 G  I  I  Y  S  Y  N  D  V  V  V  R  R  A  R  Q  M
GTCGAGCTTCGGCCTCGTCTCGTCCCAGACTCAACATTTGCTCGCCGCCA
 S  S  F  G  L  V  S  S  Q  T  Q  N  L  L  A  A
```

FIG. 3C

```
TGCTTTCCGACGAGGACTTTGTCGACAAATTTCTTGCCGAGAACTCGAAG
 M  L  S  D  E  D  F  V  D  K  F  L  A  E  N  S  K
CGTGTGGGCGAGAGGCATGCAAGgtttgttaaactacaccattattattt
 R  V  G  E  R  H  A  R
gtgggattgaaaagcattacttttttgcaattaatttaagaatgtattaat
caaattcagGTTCACAAAAGAATTGGATAAAATGGGGATCACTTGCTTGA
          F  T  K  E  L  D  K  M  G  I  T  C  L
ACAGCAATGCTGGAGTTTTTGTGTGGATGGATCTACGGAGGCTATTAAAA
 N  S  N  A  G  V  F  V  W  M  D  L  R  R  L  L  K
GACCAAACCTTCAAAGCTGAAATGGAGCTTTGGCGTGTGATTATCAATGA
 D  Q  T  F  K  A  E  M  E  L  W  R  V  I  I  N  E
AGTCAAGCTCAATGTTTCTCCTGGCTCATCCTTTCATGTCACTGAGCCAG        2000
 V  K  L  N  V  S  P  G  S  S  F  H  V  T  E  P
GTTGGTTTCGAGTTTGTTTCGCAAACATGGACGACAACACCGTTGACGTT
 G  W  F  R  V  C  F  A  N  M  D  D  N  T  V  D  V
GCTCTCAATAGAATCCATAGCTTTGTCGAAAACATCGACAAGAAGGAAGA
 A  L  N  R  I  H  S  F  V  E  N  I  D  K  K  E  D
CAATACCGTTGCAATGCCATCGAAAACGAGGCATCGAGATAATAAGTTAC
  N  T  V  A  M  P  S  K  T  R  H  R  D  N  K  L
GATTGAGCTTCTCCTTCTCAGGGAGAAGATACGACGAGGGCAACGTTCTT
 R  L  S  F  S  F  S  G  R  R  Y  D  E  G  N  V  L
AACTCACCGCACACGATGTCGCCTCACTCGCCGTTAGTAATAGCAAAAAA
  N  S  P  H  T  M  S  P  H  S  P  L  V  I  A  K  N
TTAATTAAAAACATTTTTCAAAATATTCATACCATTCATATAGTTTTTTT
  *
TTTTTTTTTTTTTGGGTCAATGTTGACTAAAGTTACGTATATTTTTTCC
ACAGTGGATATGATGTAAACTTCATATTTTTTGGTGGGATGGTGATAGAT
GTAATGTATTTGGTTTTTCCCTTAGGGAACTCATACTTATTTATTAATGA
AATGATTGTGATTTATGAattataattgtatattttctttaaaagtatt          2500
ttattgcaaaaataaataagtattatgaggaattgtaattgaatggaaaa
ggtatagagtcaaagggaataaacatatattttatttttttcttatggaag
ttttgttcatacttaaaatgtattatatttatggaaactttattgacttt
aaagatttgggacaaagggtatgatatgttcaagtttattacgtttgttg
gattagtcacttcattgacattgatgttttgttgtcatattttgtcatt
attaccacacttttttttgtctaaaagcaagcttatattcaatgaggatgc
aaaaatactttataaatggtttgtctatgtttgggtctcatagatgcacc
tttatacaaaaccgttcatacaaacaaccaaattatatatgtcgatccag
aaacgctatatacaaagtcaaatactttactgacaaactacgatcgttca
```

FIG. 3D

```
ccgtcctataacatctttttcgagtctaaccattcaatgttacatcgttt         3000
ttttttttttgtttggtaaatactttttcttttttgctttgttaaattataa
cttgggtttgttatgtgcaatttatctatttatatgcagttaacttagtt
agcttgtattgttctagtagtgaatgactagtatcttgagttgaggggct
acctcataaaatctagtaggacgacatgatagcgtggatctgaatattat
ttatggaaggttaattaacatactcttctacaagaccataaagtcatact
aaatttgggggagtgacctcgtgtacttgccagctagtaagttacgtgta
tggtccctcaccctccctcaccctctagtcatttcgactagataaagaca
catggttgccttgacgtgatatattatttggcccaggcaaacttgatgg
tacaactgttgtgctcctaccactaaaataactgatctaggtcacacatg
gctattaggtttgttaagctttcttaatcatccttggatgcttcgaggtt         3500
tattaggttttcaggatgtctagattgtttaaatctcgaactctcatttc
taggaactctggactgcacctctaggctaatctagtttataggagcacta
tggtcctgaccactgatcttcactcacgatcctagggtactcgttctaga
atgggtgttagagttagaacagtttcacgttgacctaggtcagaacgttt
tcattagaccgaacacgctaagatcgtgagcgacaatcaatggtcaagat
tatagtgctcctataaactagattagtcccaaggtgcagtccattgtgca
tagaaatgagagttggagatttaaacaacctagatgtcctaaaacctagt
aaacctcgaaggcatccaatgatgactaagaaatcttaacaaggctatta
gcagtgtgaacggtgtcatgagagcatttgcctcctatcttcttcggtac
gtcattagctctatcaatgacctaggtcagttcttttagtggcgtgtcaa         4000
gtggtaggagcacaagagttgtaccatcaagcttggcctaggccaaatag
tatagcacgtcgaggaaaccatgtgtctttatccagtcaaaatgactagg
ggacttctaaaaaaggtctctgcaccataaactgatcccgagagagggtg
agggaccatacaggtaacttagtagctgacaagcacacgaggtcgctccc
ccaaatttagtgactttatggtcgtggagaagagtatgttagttaaccttt
ccataaataatgttcacatccacgatatcatacggtcgtattagatttta
tcactattgtgtttgtatgcatggttttgcataaaggtagatctgtagca
gacagtttgcgtattggaatggcaccgccattgttaagaaggtggacacc
gtgtggccgaactctgatatgaacaaaatgaagacaagacaagtggacat
atataatcccatgaaccaggtttggacgtaaaacaatataatgcctgtcg         4500
ttttcagctgcccatttcgacaaacactcatctccattgtccagtgggtt
ctccttatattcaacaaaaatttgtttgaatgtttaaagataaaaatttg
acttttaaaccaaaaccgtgataacttaggatggtgtgataatatttaag
tcccaattttcatttgaattttaaaattgtttgaaaaaaaacatatatatt
ttttattaaaataaaagatgaaggttgacatcgaaatcttacgagataat
ccttatcggcgttctaacgaaattaatactatcatggtcttattctaaaa
gtctatgtcttttatgtattgtttaatcaaatatgaattacttggaaaat
```

FIG. 3E

```
gggatcttgtgtgtttgacttgagtttgaacaattgtcaaaatgttagct
gtaaagtagtcgcccttctcatccatttagtttaaaggatgtttcgagtt
taaattttcttctctcactccaagggagaatcatctatgtcattatatat        5000
gcaagggtggtttgattatgatagatagatgtacatttaacctgttaagt
aggggtcatgcggatcagagatctactttaaatggcgtagaaaatcctgt
ttaaacagggtcgggaataaggattatcatactctaccctgctcacttct
tatgtataaatatagatagaataaatgagaaattttatggaaatgaaaat
tgaagtaggaggaaggcgcagggacgggtaagacttccccgttctcacgc
ttccccataaacatcatacttcaactttgatgaagtatgaaattttgttt
ggtggatatccaataagtctcattgcactaaacaaagccagggaagagtt
cataaataagacgtaaagttgtggtctccaacacgtaaaacatagttact
cctcttgatttcccatgtaattgagaatttagagctttagtgtgtttaga
cgaggaagattgctttcactgaacactgagttgttccctaaatctatttg        5500
ttacaacgaggtttatcactgcttaagtgatgtaatttaggttttaattt
ctagaaaacgtgactatgtgtaatgtcagacttgttaggactttgagcat
aagctctcatgtctttgatttgaactttcttaaaaagtttcataccaatg
gagatgtattcctcgtttataaactcaagatcattcgctaacgtgggact
tccttccgataatcctcaacaaaactcagtattaacttcagtttgtttgg
tgaagtgttagaccctttctttaatcacatgcaatcatggtgagatttgt
cttttcataaaaatattatggccttatattctatttccagtctgaacaga
gttgaatgagttgtacttctctacaatcagcccatgcacacatacgagaa
cccaccagacggactcatgtctaaacaaaagggaagaatcacattagagg
gtgaagaagaaacattttacacaagtgctcggagcaacaatacgtcattt        6000
accaaacatggatataaaaatggtgacaaaggaagaagctatcaagcaca
atcagggagagctcagaagaacgacaacaataactctcaagtgaagagat
tttggggtatttactacaactgcggaaaaagggctacatgtccagagatg
gttggtctaagaaaattttttgttgaaagcaatgtggcaacatccaaaaag
gagatggaagataaatgggatgcagaggcaatatgtgtcgtagaagaaga
cgagctagcacttatggtaataaagagagaacatattgattatgaggatg
actgaatcattgattcaggatgcttaaaccacatgattaacaatcagagt
ggaacaattggatgcggagtggccctcagagaatgaagtatttcaaggct
tggaattc
```

FIG. 3F

```
                    10        20        30        40
                     .         '         ,         .
                                    aagcttaatgactacgaatcaa
          gctacttatcatccattaatcatttaatatacctcaatacgtctaactca          -2501
          atcatgttctcatcatattttttgacgtttaactgttcgtgggttggattg
          ggttgaattgaaacggttcttagatctaactaaattgttcgagtttcaac
          tttgattaaataatgaactcaactcaacccaaccgaatcataaagttttg
          gattgaacttgtttgggtaacctaattctatacaagcaagttcgtaatcc
          aaatgaaactatatatattgagttaagctgatcgaattttttcgaattcaa
          attttgttgattatcttctcattgttctatcaacctttgtatagttcttt
          gtcacaaaaacaaatcctcaccgaccatactattaattgtgatctaacgt
          aaaaaaaacgtttgtttatgtaacactttaatgatcatatttctagattc
          actaaaaagatcatgtacaaacaaaatagtcgatcacaaagactatattc
          agaagccaattttttattttaattcgactcgttttgaatctgtgttttttt          -2001
          tttttttttttttgaatctagacgaagaataacaaaaatctctccaaaatt
          cgatctccattgacttttttggtaccgatccattaatgaacgtgggtttga
          ttttagaagccctattgaattttcttgtttgaatttattaatcttctttg
          attgcgattgaccaattgatttggttgagactcaaaatcccaaaacatac
          aaaagtcttaatgtaacaacgaactcatgaacatatcgttaatgcataca
          tatcacaaaagcgtttcaacacatttgagtaaaagtgacgaaaagctgaa
          cttttttaaaacaaacttcgaaccttttaactttttatatgaattgaaca
          taacaacaaaatgttaacattgtattgacatcattatatttaacaatttt
          ccaccgaccatactactaattgtactcttaaatggaagttcttattttcg
          ttctcaaatattctaatcgttttattcattcatcgttcaacagctactc          -1500
          ttatgcattattttcttccgttatcaatttacatttctagatccactaa
          aagttcataaacaaacaaaatagtcgatcccagtcgatcccaccgaccat
          cttcctatagaagccaattttttattttaattcgactcattttgaaattat
          gttatttccccaaaattcatctccttcaacttttttggtgccaatccatta
          atgaacgtgaggttggtttagaagtccattgggttttgttgtatgattta
          attattttctttgccaacttttttcgtggtcaagcccatcgatttaaatat
          ttattatttgtttcttatcattttcttatcggctaatacgatagttttct
          atttgagcgagaaaaagcgtgctaggagattcatattggtttgtgggatt
          gtctaaacgtgaccatttgtaggagatgcaagggaataatgagacataca
          tgtgctgaattcagattcagaattgtttcaaattccgagcatggatactt          -1001
          cgtaaaagttgaaaaaccatgcacacctcgaacgagtgaacaataatatt
          gcctttctttcgcccccatactcaagaaagcttgggacgctacataagaa
          gttaaattaggtatcattgaaataggatatatttgtacttgtatgatgta
          ttgtcatacttctcgacttcatctaattatagagtttcgaagttttcata
          ctttcccattttttgttgaaaatgtattattgcacgagtgcagttggatta
          aacatctgaaccccaacgagaattaattttctcgaattttttcatttacga
```

FIG. 4A

```
tcaagcttccagaattttattgaaaaccttagagatcgaatttaggaata
cagtagaagagaatgatgctcggaatgttttctagaagctcgaaaaaata
taaaataaaatcgtagaaaataaaaaaatgtgtggtcaaagtcaatagaa
ttttgcccctcctagtattttggagaccctcgaaaaacccgagtgaatga       -501
tcattttaggtttcggttttcctcaaaatctaaagtgtatgaagaaatta
gcatatgaaaatttagtatgttgatcttgtcatgatttcgcacattttc
ttaaaagaacctgaagtcaaatcataacggaactaggagatcgaagaaga
cccaagaacggtataaacacataaatatgaaggttttgagaggggacgaa
agactacataagtagtatattgaggagctattattgtgtatggaggaagc
ccactctgagaggagatgagagactacaaaagtagatcagctgtgtctcg
aagcctaaaaaattgggttgtgacattgaaagttcgattttttcctaaggt
gacataaggggatctataacatcgtactctttgttttgttccaatttcct
acacacacgacttggtcggctgtttgtggcttgtcttttacatggtttc
aacgtgaccctgggcttataaattcactcccattttgttctttctttcgt        -1
atcttaacaacccaaaagctctcattttagggacacaaaaacaaacacc
tcaacaactttcaaATGGGGTTTCATCAAATTGACGAAAGGAACCAAGCT        100
               M  G  F  H  Q  I  D  E  R  N  Q  A
CTTCTCTCTAAGATCGCTATCGACGATGGCCATGGCGAGAACTCAGCCTA
 L  L  S  K  I  A  I  D  D  G  H  G  E  N  S  A  Y
TTTCGATGGGTGGAAAGCTTATGATAACAATCCGTTTCACCCCGAGAATA
 F  D  G  W  K  A  Y  D  N  N  P  F  H  P  E  N
ATCCTTTGGGTGTTATTCAAATGGGTTTAGCAGAAAATCAAgtttcgtat
 N  P  L  G  V  I  Q  M  G  L  A  E  N  Q
atagtgttttcatgttttcttatatcatttcacgtttgaaaatttcgct
aactttgtttctgtgtgaatttcgatagCTTTCTTTTGGTATGATTGTTG
                             L  S  F  G  M  I  V
ACTGGATTAGAAAACACCCCGAAGCTTCGATTTGTACACCTGAAGGACTT
 D  W  I  R  K  H  P  E  A  S  I  C  T  P  E  G  L
GAGAAAATTCAAAAGCATTGCCAACTTTCAAGATTATCATGGCTTACAAGA
 E  K  F  K  S  I  A  N  F  Q  D  Y  H  G  L  Q  E
GTTTCGAAAAgtactagatatgatattctaactatatctaaactcagaag         500
 F  R  K
cttaagtcgatggattatgatatatatatatatattttattttcagGCG
                                                A
ATGGCGAGTTTCATGGGGAAGGTAAGGGGTGGGAGGGTGAAATTCGACCC
 M  A  S  F  M  G  K  V  R  G  G  R  V  K  F  D  P
GAGTCGGATTGTGATGGGTGGCGGTGCGACCGGAGCGAGCGAAACCGTCA
  S  R  I  V  M  G  G  G  A  T  G  A  S  E  T  V
TCTTTTGTTTGGCGGATCCGGGGGATGCTTTTTTGGTTCCTTCTCCATAC
 I  F  C  L  A  D  P  G  D  A  F  L  V  P  S  P  Y
```

FIG. 4B

```
TATGCAGCgtaagttttttttttttttttttctttttaaatctctcctttt
 Y  A  A
cactttacatatagagagagaaaccatttgacaaattattaactctacaa
attctctttgaaagtcgtatgttttgggagggtccaaacttcaaccattc
taccaagtaaacaatccacctctttcatgcctcattgctggcatacctcc
tcgtcttctccctatactttctttctttgtattcttctccctaaccgatg
tgtaatttcacaatctactccttcgagctccagcattcttgttggcacac     1000
cactttgtgtccactcccttcgaggctcagccttctcgctagctcattg
ctcggtgtctggttctaatatcatttgtaacagtccaagtccaatgctag
tagatattgtcctcgctttgggctttccctctcggacattccatcaagtt
tttagaacacgtctgctaagaaaaagttttcacacccttataaataatgc
ttcgttctcctccctaaccgatatgggatctcactgaatattaccccactt
gaataaactaataacttgtgctcttcgttcttgatatgaaaatcaacccg
atggaaagaactgatgtcaaatgataagaaaatcactataagggaagtaa
gattcggattaccttgttgatcgaatatctcaaggcaagaacacttgttt
gaaattcgaatcactccacaaccaagattgatcatgttgagcttgaatga
ttctgcatgcaatctaaactacatagaattacaaagaaacttagtcattg     1500
gctaaagaaagcacaaatgtttcttttactatattttccaagtcggctta
caaatacaacatacatgacttcgtataatctcaaaatgaaactatttaag
gcattataagagtggtaacattcataatttatgaccataattaaccatta
tgtaaatataatctaaggtaaataaaaagccttaaaacatattaatgaaa
tacaataactccaaattttctagattgtaatccacccaaaatttataaaa
atgaaacttcattcttcttcaatgtgacatgtggcatgaactgaaatatc
tattttcttcccatgttcatcgaaatatagtgtatgattgatgtctcttg
gttcatatcagttctttacatatattaataaccttttggtacgaggtgaa
caatgtcgtattattgtaaaaatactcaaaagtctttgtcctaacaatca
gtacgttgttttttcagGTTTGATCGAGACCTAAAATGGCGAACACGAGCA      2000
                  F  D  R  D  L  K  W  R  T  R  A
CAAATAATTCCTGTTCATTGCAACAGCTCGAACAACTTCCAAGTCACAGA
 Q  I  I  P  V  H  C  N  S  S  N  N  F  Q  V  T  E
GGCAGCCTTAGAAATAGCCTATAAAAAGGCTCAAGAGGCCAACATGAAAG
 A  A  L  E  I  A  Y  K  K  A  Q  E  A  N  M  K
TGAAGGGTGTTATAATCACCAATCCCTCAAATCCCTTAGGCACAACGTAC
 V  K  G  V  I  I  T  N  P  S  N  P  L  G  T  T  Y
GACCGTGACACTCTTAAAACCCTCGTCACCTTTGTGAATCAACACGACAT
 D  R  D  T  L  K  T  L  V  T  F  V  N  Q  H  D  I
```

FIG. 4C

```
TCACTTAATATGCGATGAAATATACTCTGCCACTGTCTTCAAAGCCCCAA
  H  L  I  C  D  E  I  Y  S  A  T  V  F  K  A  P
CCTTCACCAGCATCGCTGAGATTGTTGAACAAATGGAGCATTGCAAGAAG
  T  F  T  S  I  A  E  I  V  E  Q  M  E  H  C  K  K
GAGCTCATCCATATTCTTTATAGCTTGTCCAAAGACATGGGCCTCCCTGG
  E  L  I  H  I  L  Y  S  L  S  K  D  M  G  L  P  G
TTTTCGAGTTGGAATTATTTATTCTTACAACGATGTCGTCGTCCGCCGTG
  F  R  V  G  I  I  Y  S  Y  N  D  V  V  V  R  R
CTCGGCAGATGTCGAGCTTCGGCCTCGTCTCGTCCCAGACTCAACATTTG
  A  R  Q  M  S  S  F  G  L  V  S  S  Q  T  Q  H  L
CTCGCCGCCATGCTTTCCGACGAGGACTTTGTCGACAAATTTCTTGCCGA      2500
  L  A  A  M  L  S  D  E  D  F  V  D  K  F  L  A  E
GAACTCGAAGCGCCTGGGCGAGAGGCATGCAAGgtttgttaaactacacc
  N  S  K  R  L  G  E  R  H  A  R
attattatttgtgggattgaaaagcattacaaaatgcaattaatttaaga
atgtattaatcaaattcagGTTCACAAAAGAATTGGATAAAATGGGGATC
                    F  T  K  E  L  D  K  M  G  I
ACTTGCTTGAACAGCAATGCTGGAGTTTTTGTGTGGATGGATCTACGGAG
  T  C  L  N  S  N  A  G  V  F  V  W  M  D  L  R  R
GCTATTAAAAGACCAAACCTTCAAAGCTGAAATGGAGCTTTGGCGTGTGA
  L  L  K  D  Q  T  F  K  A  E  M  E  L  W  R  V
TTATCAATGAAGTCAAGCTCAATGTTTCTCCTGGCTCATCCTTTCATGTC
  I  I  N  E  V  K  L  N  V  S  P  G  S  S  F  H  V
ACTGAGCCAGGTTGGTTTCGAGTTTGTTTCGCAAACATGGACGACAACAC
  T  E  P  G  W  F  R  V  C  F  A  N  M  D  D  N  T
CGTTGACGTTGCTCTCAATAGAATCCATAGCTTTGTCGAAAACATCGACA
  V  D  V  A  L  N  R  I  H  S  F  V  E  N  I  D
AGAAGGAAGACAATACCGTTGCAATGCCATCGAAAACGAGGCATCGAGAT
  K  K  E  D  N  T  V  A  M  P  S  K  T  R  H  R  D
AATAAGTTACGATTGAGCTTCTCCTTCTCCGGGAGAAGATACGACAAGGG      3000
  N  K  L  R  L  S  F  S  F  S  G  R  R  Y  D  K  G
CAACGTTCTTAACTCACCGCACACGATGTCGCCTCACTCGCCATTGGTAA
  N  V  L  N  S  P  H  T  M  S  P  H  S  P  L  V
GAGCCAGAACTTATTAAagatgagtttgagaagatattatcataagtttt
  R  A  R  T  Y  *
ttttagctcattaatgaatggatggatatttaaaactatgaagtgtagca
ctcatgctccgaaggaattaatttcttgattgctgaattttaagacgata
taaaagagaaaaaatgtttagaaaaatctaaaaaatgggagaaaaaaag
```

FIG. 4D aaaacaattaaaatttaaaaatcagtcaaaatcattaaagtagtacatat
agctcatactagaaggtgagacaagactctgaaatgattttatgatacg
tctttaactacgattgcatttcttgactggggttactgcatttcttgact
ggggttacttactaagtatttctagaaatactcaagtcacatgctactct
tattttcaggtaaaggcaatgtacctcttcacggacgatgacgtcgcggt 3500
gacgccatgagattgaagctagggtagaagtattcatgttatttttgtag
cccttaggttagatcaaaatatcgtcttatttttattttatttatcaaa
atttacgtgatttgttttccattttaattgttcaataattttattatga
acatgtaagttcatggcactttttaaaatattttaaaagttttttttt
tcgattcttaattaatttatgcatgtagtagcgagtttatcatagtcaag
gaggatgttttgtgaaatgttaagctgaatggttatgtgtaaaacggaga
gtctactaatgctattaagattttatgtaaacaagtcttccacttgatt
tctgtcttgatttgctacatctcgatttcttccgtcaagaatttctctct
aacgaaatgataatgcacctccacatgttttattctagcatgaaacatcg
aattttctgttaggcaaatcgcagattggttgttgtaatgaagtggtatt 4000
ggatagtcaattttcttgtgccgatctttcatcaagagtttcagtcatgt
actttcctaaactgctccaaccgctactctgtactctacttctctagttg
acaatgatactgttgattttcttttgctacactgagaagttgttctcgaa
ccgagcttgaacacatacctggtgcttgatcttcgggtattgtgatattc
tacatagtcagcatcacggtatctggataacttgtagtcttcgcttcttt
tatacaaacgatcataatgattgtgcctttgacatatctcaaggtccgtc
aagtcgcatccaaatgaggtttctttgcactttgtatgtactgactaatg
actccaactccgttctcaaatttcttcggttggttcatgtagatctctct
atttaactctccgtgcaagaaagcattcttcatatccatctgtcgtaatt
tccaatctttatttaccacaagtgctggaggaacctatatgatggtgatc 4500
tttgccactgaactaaatgtttcatcatagtccatattgttgagagaacc
ctggagctacagtctgagttgtgtatctcactattcatccattcgggata
cactttattttgtaaatccacttgcaaaagatggatttgacatcttctgg
tctttgtactaattcccaggtttgatttatctcgaagggtataatttctt
cctccattgtctgctgccaagccgtattgcgtgatgcttctttatacgtc
tctagctctttactttgtcttctaaaatagttatattgaacatactttgg
atttggcttatggattctttctaaccatctaagtcgttgaggtgtcattt
ccttttcactaggttcgcttgattgagtcactccttgctcaccaacatta
gtgtcacttggatatttagacacatcagcatttaagaaaatgtgtacagt
tttctcccccgtattctgtggaagaatttcttcagtttgctcccccgtct 5000
tctgtggaagaattc

```
                 10        20        30        40
                  .         .         .         .
ptACCI→ tgtagttgtgtacattttattaatcttcatcttcttaattctcttcagtt
        tttaatttcttcacttctaaactcatttagtaaaaaaaaaaATGGGATTTG      100
                                                 M  G  F
        AGATTGCAAAGACCAACTCAATCTTATCAAAATTGGCTACTAATGAAGAG
         E  I  A  K  T  N  S  I  L  S  K  L  A  T  N  E  E
        CATGGCGAAAACTCGCCATATTTTGATGGGTGGAAAGCATACGATAGTGA        200
         H  G  E  N  S  P  Y  F  D  G  W  K  A  Y  D  S  D
        TCCTTTCCACCCTCTAAAAAACCCCAACGGAGTTATCCAAATGGGTCTTG
          P  F  H  P  L  K  N  P  N  G  V  I  Q  M  G  L
        CTGAAAATCAGCTTTGTTTAGACTTGATAGAAGATTGGATTAAGAGAAAC        300
         A  E  N  Q  L  C  L  D  L  I  E  D  W  I  K  R  N
        CCAAAAGGTTCAATTTGTTCTGAAGGAATCAAATCATTCAAGGCCATTGC
          P  K  G  S  I  C  S  E  G  I  K  S  F  K  A  I  A
        CAACTTTCAAGATTATCATGGCTTGCCTGAATTCAGAAAAGCGATTGCGA        400
          N  F  Q  D  Y  H  G  L  P  E  F  R  K  A  I  A
        AATTTATGGAGAAAACAAGAGGAGGAAGAGTTAGATTTGATCCAGAAAGA
          K  F  M  E  K  T  R  G  G  R  V  R  F  D  P  E  R
        GTTGTTATGGTTGGTGGTGCCACTGGAGCTAATGAGACAATTATATTTTG        500
         V  V  M  V  G  G  A  T  G  A (N) E  T  I  I  F  C
        TTTGGCTGATCCTGGCGATGCATTTTTAGTACCTTCACCATACTACCCAG
          L  A  D  P  G  D  A  F  L  V  P  S  P  Y  Y  P
        CATTTAACAGAGATTTAAGATGGAGAACTGGAGTACAACTTATTCCAATT        600
         A  F  N  R  D  L  R  W  R  T  G  V  Q  L  I  P  I
        CACTGTGAGAGCTCCAATAATTTCAAAATTACTTCAAAAGCAGTAAAAGA
         H  C  E  S  S  N  N  F  K  I  T  S  K  A  V  K  E
        AGCATATGAAAATGCACAAAAATCAAACATCAAAGTAAAAGGTTTGATTT        700
         A  Y  E  N  A  Q  K  S  N  I  K  V  K  G  L  I
        TGACCAATCCATCAAATCCATTGGGCACCACTTTGGACAAAGACACACTG
          L  T  N  P  S  N  P  L  G  T  T  L  D  K  D  T  L
        AAAAGTGTCTTGAGTTTCACCAACCAACACAACATCCACCTTGTTTGTGA        800
          K  S  V  L  S  F  T  N  Q  H  N  I  H  L  V  C  D
        CGAAATCTACGCAGCCACTGTCTTTGACACGCCTCAATTCGTCAGTATAG
          E  I  Y  A  A  T  V  F  D  T  P  Q  F  V  S  I
```

FIG. 5A

```
CTGAAATCCTCGATGAACAGGAAATGACTTACTGCAACAAAGATTTAGTT    900
 A  E  I  L  D  E  Q  M  T  Y  C  N  K  D  L  V
CACATCGTCTACAGTCTTTCAAAAGACATGGGGTTACCAGGATTTAGAGT
 H  I  V  Y  S  L  S  K  D  M  G  L  P  G  F  R  V
CGGAATCATATATTCTTTTAACGACGATGTCGTTAATTGTGCTAGAAAAA    1000
    G  I  I  Y  S  F  N  D  D  V  V  N  C  A  R  K
TGTCGAGTTTCGGTTTAGTATCTACACAAACGCAATATTTTTTAGCGGCA
  M  S  S  F  G  L  V  S  T  Q  T  Q  Y  F  L  A  A
ATGCTATCGGACGAAAAATTCGTCGATAATTTTCTAAGAGAAAGCGCGAT    1100
  M  L  S  D  E  K  F  V  D  N  F  L  R  E  S  A  M
GAGGTTAGGTAAAAGGCACAAACATTTTACTAATGGACTTGAAGTAGTGG
  R  L  G  K  R  H  K  H  F  T  N  G  L  E  V  V
GAATTAAATGCTTGAAAAATAATGCGGGGCTTTTTTGTTGGATGGATTTG    1200
  G  I  K  C  L  K  N  N  A  G  L  F  C  W  M  D  L
CGTCCACTTTTAAGGGAATCGACTTTCGATAGCGAAATGTCGTTATGGAG
  R  P  L  L  R  E  S  T  F  D  S  E  M  S  L  W  R
AGTTATTATAAACGATGTTAAGCTTAACGTCTCGCCTGGATCTTCGTTTG    1300
  V  I  I  N  D  V  K  L  N  V  S  P  G  S  S  F
AATGTCAAGAGCCAGGGTGGTTCCGAGTTTGTTTTGCAAATATGGATGAT
  E  C  Q  E  P  G  W  F  R  V  C  F  A  N  M  D  D
GGAACGGTTGATATTGCGCTCGCGAGGATTCGGAGGTTCGTAGGTGTTGA    1400
  G  T  V  D  I  A  L  A  R  I  R  R  F  V  G  V  E
GAAAAGTGGAGATAAATCGAGTTCGATGGAAAAGAAGCAACAATGGAAGA
  K  S  G  D  K  S  S  S  M  E  K  K  Q  Q  W  K
AGAATAATTTGAGACTTAGTTTTTCGAAAAGAATGTATGATGAAAGTGTT    1500
  K  N  N  L  R  L  S  F  S  K  R  M  Y  D  E  S  V
TTGTCACCACTTTCGTCACCTATTCCTCCCTCACCATTAGTTCGTTAAga
  L  S  P  L  S  S  P  I  P  P  S  P  L  V  R  *
cttaattaaaaggaagaatttaatttatgttttttatattttgaaaaa     1600
aatttgtaagaataagattataataggaaaagaaaataagtatgtaggat
gaggagtattttcagaaatagttgttagcgtatgtattgacaactggtct    1700
```

FIG. 5B ptACC1 —atgtacttagacatcataatttgtcttagctaattaacgaatgcaaaagt
gaagttatgttatgactcttagaat
ptACC2 —atgtacttagacatcataatttgtcttagctaattaatgaatgcaaaagt
gaagttatgttatgactcttagaatcttttgatttattggactttctcga      1800
ptACC3 —atgtacttagacatcataatttgtcttagctaattaatgaatgcaaaagt
gaagttatgttatg(a)$_{19}$
ptACC4 —atgtacttagacatcataatttgtcttagctaattaatgaatgcaaaagt
gaagttatgtt(a)$_{20}$
ptACC5 —atgtacttagacatcataatttgtcttagctaattaatgaatgcaaaagt
gaagttatgtt(a)$_{19}$
ptACC6 —atgtacttagacatcataatttgtcttagctaatt(a)$_{58}$ ptACC2 —ttatat tgtt(a)$_8$

FIG. 5C

```
              10        20        30        40
              •         •         •         •
              ggatcctcattacttgtctatggctaaagtgtt
aaagaattattcacaatatctaacacatttaatgactattcaactaatag
tgacgatcttttaaaataaaatgaagaacttaaaattttgaccaacttcc
taacgatattaatgagggatacagatttgatttacgcaaaaaaaaagaa
aaaaagaaatgatattactcaattataaatttgattagagaatagctagg
cctataattgttttacattatctattcctaagttatgatattatccttca
atttacctgatagcgtaaaaattacaataatttgtacactaatgatgcac
aaaacttaaattcattatatatacacatacaaggccgagggcttaataga     -2501
atcgatgacctgaaatcatatttctattgtttagcaatagaaattagtta
tggcttcaaatttagcgatgaattccatgggtgtttgcattgacttaaaa
gatgatcaaatctactttgaagtccgttttgaattttgaaagtgtttga
taaatataaaaataactaaaaataagttaggaagtgtttgacaaagttaa
atcttaaaataatttatcaaccaaaagtaggtctcccctattcttttttt
ttttggacttaaaagtcgtttaaacgtaatttgacttataaatttttaa
agttaattaaaccggctttgtaaagaaattaacaattcatttggaatg
ttaattattaaaagatccagatatgtacaaaataaaaataacctacctcc
tatagtaaagattttcaaacaatattaagttaaacaaagtcaaaaagttg
gtatattgaattttactagtcttgtataaaccaatacaattagcttcgaa     -2001
aagtcattgatatatttttctatgtgctgcttgtgggaaacttcctgta
acacaaagaatgaatgaattctcccacattttatttgtagatttaatt
ccctatttgatatcaaaatattctggagaaggaaggaatacgagcctaa
ccaagactaggccaattaagcagcccatgataagcctccattcaaatgaa
atatcaaaatcactgtattattataagatactttgagaatatatattgtt
tggtcaaatagtttattaacatatatatttatatataagtatgtgaaatga
tgaagctagagttttatatgaacatataatttagattttaagttgtatat
tttgctcataaatataaaattctatgaattgtaaaattatcaatatttac
ttaattctttacgcaatcttactaaatatataaaagttaataactacaaa
agtataatcatacgatcacaaacgagctattctaaaaaaagtatcacata     -1501
tttaatataatcctcccacatagtacaaacaatcttctcatgttttgtaa
taataaatgatgtaagggtttaaaggtggtgtgaataataattgcaacta
aaaaatttatttacatctaaaataaataattaatacatataaaatcgtat
gatcaaaaatttaaaatttaaatcatgatatgtaattaatatgtccagac
acctgcttaataaaaactatacactattaatgcagtatgcactttataca
tattttgtaaattagataattaaatggccggctagagtaatgcaatacga
tagaaaagctcgatcaaaattaatcacactcaatgtgcctagtaagatct
tcaaatcaaaatcaattatgattatcatctgcggtccattgttctcgtcc
```

FIG. 9A

```
cttcccaggaaagtaattatccctattatattttttatttatttatataaa
ctacttgaaaaaggtaaaaagaataaataaataaattaccagtagtacca      -1001
ttgtattctaactttttttctttctcacgtgtagcttctagcttgaacat
gaaatttcatataactatttagacgaaggcaattacgactaagggtatgt
tcgataagaaaagaaaatattttcttaaaaaataaataaattttttaattt
attttcatatttgattaataagcagaaaatattttgaggaagtatctt
tttttattttttgagaaaatactttctatgaaaataattattgatgtgaaa
atcaatctcgataattgttgcaggaaacgactctgacaatcgaattagga
taaaacctcgatgacctttaaaatcgaccctaaaatctgatccaaaactc
gatccagacttccgatccaaaacttgattcaagtaaatattttttaaaaat
aaattcttttttgacagggtggcgtaaaaataattttatttttaaaatatga
tatagttttctaaaatatatttttttgtttggttattgggggttggttcg     -501
aggctaggggtaaaaataattaaaacataagaaattttaaaagttttaat
tgcattttttttgtgttggggaggggcggattttgggttggataagaaaa
aatatttaaagataaaatagaattttggaaaatattttttcttaattttg
aaggaaaatcattttttcttaaatttgagaaaaatgaattattcttaaaaa
aaatttccaaaaacatttaagctaccaaatatgaaaaaataaaaaatatt
ttttttcctaccaaatgcaccctaaattagtcaaatatccaacatttaaa
agagctatgaaaaaaaaaagaagtaagaatcgtagatcttcttttaatg
cgtacttttattttccaagatttgaacaataaaatagacttttctatttt
tattttctgatgtaattcttatatacgttagtcgacatgttctcattaca
tacttcagtctttccccttatatatatccctcacattccttaattctctt     -1
ACACCATAACACAACTACAACAAACACATAATACTTTTAATACAATTAGT
TATTTATTAGAAGTATTTAAAGTAAAGCACTTGTGAGTTGTGTACATTTT
ATTAATCTTCATCTTCTTAATTCTCTTCAGTTTTTAATTTCTTCACTTCT      100
AAACTCATTTAGTAAAAAAAAAATGGGATTTGAGATTGCAAAGACCAACT
                       M  G  F  E  I  A  K  T  N
CAATCTTATCAAAATTGGCTACTAATGAAGAGCATGGCGAAAACTCGCCA
 S  I  L  S  K  L  A  T  N  E  E  N  G  E  N  S  P
TATTTTGATGGGTGGAAAGCATACGATAGTGATCCTTTCCACCCTCTAAA
   Y  F  D  G  W  K  A  Y  D  S  D  P  F  N  P  L  K
AAACCCCAACGGAGTTATCCAAATGGGTCTTGCTGAAAATCAGgtaatta
   N  P  N  G  V  I  Q  M  G  L  A  E  N  Q
attatcctttatttatatattttgcagtttgaccaaacagactattataa
ttttttttctgaaacctcgatggtgttaaatttcttttgtagCTTTGTTTA
                                              L  C  L
GACTTGATAGAAGATTGGATTAAGAGAAACCCAAAAGGTTCAATTTGTTC      500
   D  L  I  E  D  W  I  K  R  N  P  K  G  S  I  C  S
```

FIG. 9B

```
TGAAGGAATCAAATCATTCAAGGCCATTGCCAACTTTCAAGATTATCATG
  E  G  I  K  S  F  K  A  I  A  N  F  Q  D  Y  N
GCTTGCCTGAATTCAGAAAAgtacatatcgtactatagtcagttaaatta
 G  L  P  E  F  R  K
tattgatagtataaaaattcgttaatatatttaactaacgagtttatttt
atcagGCGATTGCGAAATTTATGGAGAAAACAAGAGGAGGAAGAGTTAGA
       A  I  A  K  F  N  E  K  T  R  G  G  R  V  R
TTTGATCCAGAAAGAGTTGTTATGGCTGGTGGTGCCACTGGAGCTAATGA
  F  D  P  E  R  V  V  M  A  G  G  A  T  G  A  N  E
GACAATTATATTTTGTTTGGCTGATCCTGGCGATGCATTTTTAGTACCTT
    T  I  I  F  C  L  A  D  P  G  D  A  F  L  V  P
CACCATACTACCCAGCgtaagtatatttaattatatatgtgtaaaaaaaa
 S  P  Y  Y  P  A
ttaaaatcatcaaatcattttttttatttgtattaccaaataaattgtct
aattttcaagattgtaacacattcatcaaagtacctaataatataaacga
ttcagtatattaacgatgtatataatttaattcctttggcggatttgtct  1000
ttttatgttgggccatcagaagaacattctggtgtattaattaattaatt
aattaataatagatgtgttg cattcttttttaagacagcgagagtttaa
ttagtcttaattactggattatcacgcaagctctttcttgaattttatta
ttcttatattaaacacatgatagcataatatctttcttttgtggaatcca
gcttgttcgtgaagctttgtattcacacttataaaacaacaaaaaataaa
atctggtggtaattgattaaagagagaaatataaaaaaataatagtcaaa
tagactaataaggaaagaaataaaaaatacacaaaatactaaaaaaaaag
aattaaggtatagtggtctattattgagaacttttttgaagaattgaacc
ccactttaatttcttgcttgacccgtgaccattgcttatcgaggtaaaat
aaaatttcaaacattgactatgacttgttagagagtaattaccacaagtc  1500
aaaattttgttactctgtctcgttatttcattaggatcgataagataaca
tctaacatatatatctttttttattagtacttgtttatttttagtaaaagc
acgttatacattttacaatagtcaattgttgcatatattagtatatatat
tttgctaagtcctaactaacaatattttttggcaattgactaatgcagATT
                                                  F
TAACAGAGATTTAAGATGGAGAACTGGAGTACAACTTATTCCAATTCACT
   N  R  D  L  R  W  R  T  G  V  Q  L  I  P  I  N
GTGAGAGCTCCAATAATTTCAAAATTACTTCAAAAGCAGTAAAAGAAGCA
   C  E  S  S  N  N  F  K  I  T  S  K  A  V  K  E  A
TATGAAAATGCACAAAAATCAAACATCAAAGTAAAAGGTTTGATTTTGAC
   Y  E  N  A  Q  K  S  N  I  K  V  K  G  L  I  L  T
CAATCCATCAAATCCATTGGGCACCACTTTGGACAAAGACACACTGAAAA
   N  P  S  N  P  L  G  T  T  L  D  K  D  T  L  K
```

FIG. 9C

```
GTGTCTTGAGTTTCACCAACCAACACAACATCCACCTTGTTTGTGACGAA
 S  V  L  S  F  T  N  Q  N  N  I  N  L  V  C  D  E
ATCTACGCAGCCACTGTCTTTGACACGCCTCAATTCGTCAGTATAGCTGA          2000
  I  Y  A  A  T  V  F  D  T  P  Q  F  V  S  I  A  E
AATCCTCGATGAACAGGAAATGACTTACTGCAACAAAGATTTAGTTCACA
   I  L  D  E  Q  E  M  T  Y  C  N  K  D  L  V  N
TCGTCTACAGTCTTTCAAAAGACATGGGGTTACCAGGATTTAGAGTCGGA
  I  V  Y  S  L  S  K  D  N  G  L  P  G  F  R  V  G
ATCATATATTCTTTTAACGACGATGTCGTTAATTGTGCTAGAAAAATGTC
  I  I  Y  S  F  N  D  D  V  V  N  C  A  R  K  M  S
GAGTTTCGGTTTAGTATCTACACAAACGCAATATTTTTAGCGGCAATGC
   S  F  G  L  V  S  T  Q  T  Y  F  L  A  A  N
TATCGGACGAAAAATTCGTCGATAATTTTCTAAGAGAAAGCGCGATGAGG
   L  S  D  E  K  F  V  D  N  F  L  R  E  S  A  N  R
TTAGGTAAAAGGCACAAACATTTTACTAATGGACTTGAAGTAGTGGGAAT
   L  G  K  R  N  K  N  F  T  N  G  L  E  V  V  G  I
TAAATGCTTGAAAAATAATGCGGGGCTTTTTTGTTGGATGGATTTGCGTC
   K  C  L  K  N  N  A  G  L  F  C  W  M  D  L  R
CACTTTTAAGGGAATCGACTTTCGATAGCGAAATGTCGTTATGGAGAGTT
   P  L  L  R  E  S  T  F  D  S  E  M  S  L  W  R  V
ATTATAAACGATGTTAAGCTTAACGTCTCGCCTGGATCTTCGTTTGAATG
   I  I  N  D  V  K  L  N  V  S  P  G  S  S  F  E  C
TCAAGAGCCAGGGTGGTTCCGAGTTTGTTTTGCAAATATGGATGATGGAA          2500
   Q  E  P  G  W  F  R  V  C  F  A  N  N  D  D  G
CGGTTGATATTGCGCTCGCGAGGATTCGGAGGTTCGTAGGTGTTGAGAAA
  T  V  D  I  A  L  A  R  I  R  R  F  V  G  V  E  K
AGTGGAGATAAATCGAGTTCGATGGAAAAGAAGCAACAATGGAAGAAGAA
  S  G  D  K  S  S  S  M  R  K  K  Q  Q  W  K  K  N
TAATTTGAGACTTAGTTTTTCGAAAAGAATGTATGATGAAAGTGTTTTGT
   N  L  R  L  S  F  S  K  R  M  Y  D  E  S  V  L
CACCACTTTCGTCACCTATTCCTCCCTCACCATTAGTTCGTTAAGACTTA
   S  P  L  S  S  P  I  P  P  S  P  L  V  R  *
ATTAAAAGGGAAGAATTTAATTTATGTTTTTTTATATTTTGAAAAAAATT
TGTAAGAATAAGATTATAATAGGAAAAGAAAATAAGTATGTAGGATGAGG
AGTATTTTCAGAAATAGTTGTTAGCGTATGTATTGACAACTGGTCTATGT
ACTTAGACATCATAATTTGTCTTAGCTAATTAATGAATGCAAAAGTGAAG
TTATGTTATGACTCTTAGAATCTTTTGATTTATTGGACTTTCTCGATTAT
ATTGTTAttattaaatttcatatattttatatatttaaaaagtgtcgtaa          3000
```

FIG. 9D

```
gtcataataattgacaagatatatgaaaactttacgatcaaagataaatt
tgtttaaattttaaaatttaaagtgtgtcacataaattgagatggagaga
ttatggtgtttgtgtatattttaatggaaaaatacagtgcgtgtttgtgg
gggattgactccagatgatagagtagaaatggatctcctaattttttat
ttatgttttactttatcgagggtctatcaaaaataatttatctattttt
aaatagagataaagtctgacatactcttttttacttgtatttatatgtcat
gattttgattaggagtttggattttctctacgttcaaatacaaattaaac
tataatgagttattttccctaaatttggagaaattatcatttggagatga
gtacacgataataatgtcctctaatcaattacatcaaacacaaaaacatt
attagaaattcacaatctacatgtttgtctaattaatcacatcttcatag    3500
ttgataagtagtacttatcatactttgtagtttatgatttcgaataactt
gacatatgattaattttgtaatactacattactgtttatcaaacttgttt
ttcgaattcatttctagtagtgtgtggcatgacttggacaagagaaatac
aaatattttgaatttattcctactatacatttattttattttaatctat
atataaaagaatatcgtacatatttattaatataaaattttgatatttac
tttttattatagaatttgatatccagtcaaaccgccacataaattgagcc
aatatgtaaatagaaaatgttgacaaaagaaatggatttattggaagaca
aactgacataggg tccaactgaaaagagttaaattgtcggacgactttat
aatattttagtcaaccccacccaaagcctttta aacttagataaatccaa
aagataataattttgattgatatttta taatgtatctttttatcatattg    4000
acatgtagaaaaattataatttataatattttttatatagttttaaata
tttaaaattttta tttaaaatattaaatgaatatattttaactttagtta
atcaatgacttttaaaaaacgtaatatgacaattaaatgaatagaaaaa
tatcgattaataagacttttgagatgaaaatattgtctcatgtgaacgat
gctaacgatgtctccaacatggattttgcttccttggctttatttcatga
tttaatatttatattgaaatgactaaggtaagtaaaaaaacaaatttcat
attaaagttttgtttgagttgaattcaagttttgattattttctattag
aaatcagatct
```

```
VVRRARQMSSFGLVSSQTQHLLAAMLSDEDFVDKFLAENSKRVGERHARFTKELDKMGITCLNSNAGVFVWMDLRRLLKDQTFKAEMELWRVIINEVKLNV
VVRRARQMSSFGLVSSQTQHLLAAMLSDEDFVDKFLAENSKRLGERHARFTKELDKMGITCLNSNAGVFVWMDLRRLLKDQTFKAEMELWRVIINEVKLNV
VVNIARKMSSFGLVSSQTQHLLASMLSDEVFiDKFIAESSERLGERQGMFTKGLAEVGISTLKSNAGLFFWMDLRRLLKEATFDSELELWRIINEVKLNV
VVNIsRKMSSFGLVSTQTQHmLASMLSDEiFVEKFIAESSERLGKRQGMFTKGLAQVGISTLKSNAGLFFWMDLRRLLKEATFDgELELWRIINEVKLNV
VVNCARKMSSFGLVSTQTQYfLAAMLSDEKFVDnFLrESAmRLGKRHKhFTnGLEVVGIKCLKnNAGLFCWMDLRpLLrEsTFDSEMSLWRVIINDVKLNV
VVsaAtKMSSFGLVSSQTQYLLsCMLSDKKFtkKyIsENqKRLkKRHAMIVKGLksaGInCLESNAGLFCWVDmRhLLssnnFDAEMdLWKkIyyDVgLNI
VVNCARKMSSFGLVSTQTQHLLAfMLSDdeFVEeFLiESAKRLrERyekFTRGLEEiGIKCLESNAGVyCWMDLRsLLKEATIDAEMSLWKIIINEVKLNV SPGSSFHVTEPGWFRVCFANMDDNTVDVALNRIHSFV------ENIDKKEDNTVAMPSKTRHRDNKLRLSFSFSGRRYDEGNVLNSPHTMSPH--SPLViAkn
SPGSSFHVTEPGWFRVCFANMDDNTVDVALNRIHSFV------ENIDKKEDNTVAMPSKTRHRDNKLRLSFSFSGRRYDKGNVLNSPHTMSPH--SPLVrARTy
SPGCSFHCSEPGWFRVCFANMDDETMRIALKRISyFV------LQDKGLNNIAAIKKQCSRRKLQISLSF----RRLDh-eFmNSPAH-SPMN-SPLV--RT
SPGCSFHCSEPGWFRVCFANMDDETMRIALRRIRnFV------LQtKGLNNIAAIKKQCSRKLQISLSF----RRLDd--F-NSPAH-SPMN-SPLV--RT
SPGSSFeCqEPGWFRVCFANMDDgTVDIALARIRrFV------gveKsgDKSssMeKKqqwKKNnLRLSFS--kRmYDEs-VL-SPls-SPiPpSPLV--R
SPGSSCHCTEPGWFRVCFANMsedTIDiAmRRIkdFVestapnaTNhqnqqSNAnsKKKsFsSKwvFRLSFndrqRer
SPGSSFnCSEVGWFRVCFANiDDqTMeiALARIRmFmdaynnvnkNgvmkNKhNgrgttydItpqmgStmkmlla
```

FIG. 10B

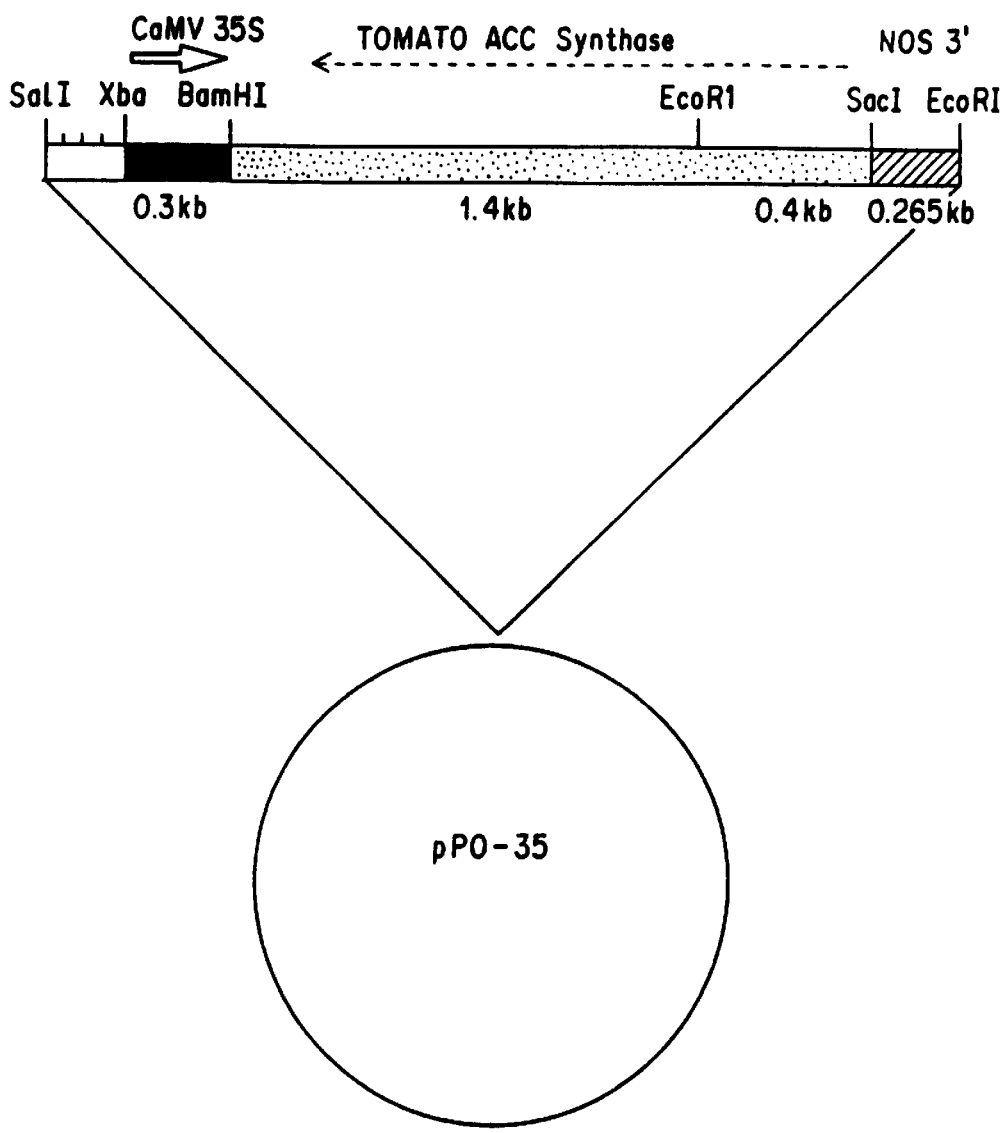
35S PROMOTER DRIVES *ANTISENSE* TOMATO ACC SYNTHASE
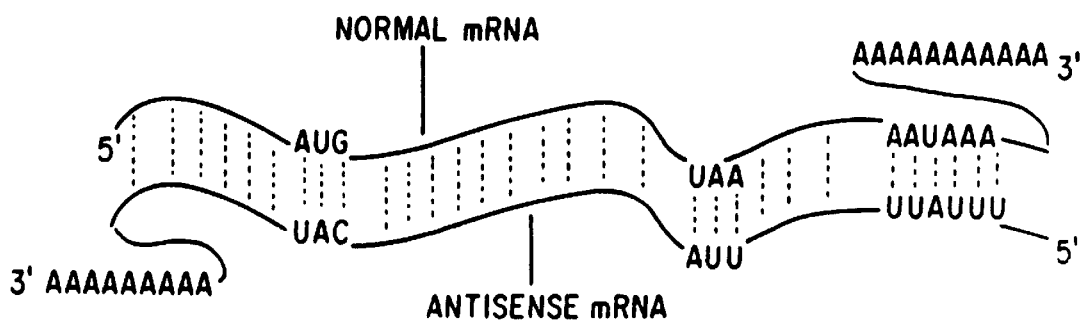
FIG. 14

SEQUENCE LISTING (1) GENERAL INFORMATION:

(iii) NUMBER OF SEQUENCES: 34

(2) INFORMATION FOR SEQ ID NO:1:

```
    (i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:1:

Gln Met Gly Leu Ala Glu Asn Gln Leu
1               5

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:2:

Phe Gln Asp Tyr His Gly Leu
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 5
        (D) OTHER INFORMATION: /note= "This position is V/T."

(xi) SEQUENCE DESCRIPTION: SEQ ID NO:3:

Phe Met Glu Lys Xaa
1               5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "This position is K/A."

(ix) FEATURE:
        (A) NAME/KEY: Modified-site
        (B) LOCATION: 3
        (D) OTHER INFORMATION: /note= "This position is L/V."

(ix) FEATURE:
        (A) NAME/KEY: Modified-site
        (B) LOCATION: 5
        (D) OTHER INFORMATION: /note= "This position is E/I."

(xi) SEQUENCE DESCRIPTION: SEQ ID NO:4:

Xaa Ala Xaa Glu Xaa Ala Tyr
1               5

(2) INFORMATION FOR SEQ ID NO:5:

(i) SEQUENCE CHARACTERISTICS:
        (A) LENGTH: 7 amino acids
```

```
            (B) TYPE: amino acid
            (C) STRANDEDNESS: single
            (D) TOPOLOGY: linear (ix) FEATURE:
            (A) NAME/KEY: Modified-site
            (B) LOCATION: 6
            (D) OTHER INFORMATION: /note= "This position is V/I."

(xi) SEQUENCE DESCRIPTION: SEQ ID NO:5:

Gly Asp Ala Phe Leu Xaa Pro
1               5

(2) INFORMATION FOR SEQ ID NO:6:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:6:

Asn Pro Leu Gly Thr
1               5

(2) INFORMATION FOR SEQ ID NO:7:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:7:

Ser Leu Ser Lys Asp
1               5

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 5
            (D) OTHER INFORMATION: /note= "This position is V/I."

(xi) SEQUENCE DESCRIPTION: SEQ ID NO:8:

Pro Gly Phe Arg Xaa Gly
1               5

(2) INFORMATION FOR SEQ ID NO:9:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:9:

Arg Val Cys Phe Ala Asn Met Asp
1               5

(2) INFORMATION FOR SEQ ID NO:10:

(i) SEQUENCE CHARACTERISTICS:
```

(A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:10:

Met Ser Ser Phe Gly Leu Val Ser
1               5

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /note= "This position is M/I."

(xi) SEQUENCE DESCRIPTION: SEQ ID NO:11:

Gly Trp Phe Arg Val Cys Phe Ala Asn Xaa
1               5                   10

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:12:

Met Gly Leu Ala Glu Asn Gln
1               5

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 5
        (D) OTHER INFORMATION: /note= "This position is V/T."

(xi) SEQUENCE DESCRIPTION: SEQ ID NO:13:

Phe Met Glu Lys Xaa Arg
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /note= "This position is L/V."

(xi) SEQUENCE DESCRIPTION: SEQ ID NO:14:

Lys Ala Xaa Glu Glu Ala Tyr

-continued

```
1               5
```

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:15:

```
Phe Pro Gly Phe Arg Val Gly
1               5
```

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:16:

```
Lys Ala Leu Glu Glu Ala Tyr
1               5
```

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:17:

```
Thr Ala Thr Ala Ala Thr
1               5
```

(2) INFORMATION FOR SEQ ID NO:18:

(i) SEQUENCE CHARACTERISTICS:
        (A) LENGTH: 1703 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 11..1489

(xi) SEQUENCE DESCRIPTION: SEQ ID NO:18:

```
CAACTTTCAA ATG GGG TTT CAT CAA ATC GAC GAA AGG AAC CAA GCT CTT        49
           Met Gly Phe His Gln Ile Asp Glu Arg Asn Gln Ala Leu
             1               5                  10

CTC TCG AAG ATC GCC CTC GAC GAT GGC CAT GGC GAG AAC TCC CCG TAT       97
Leu Ser Lys Ile Ala Leu Asp Asp Gly His Gly Glu Asn Ser Pro Tyr
 15                  20                  25

TTC GAT GGG TGG AAA GCT TAC GAT AAC GAT CCG TTT CAC CCT GAG AAT      145
Phe Asp Gly Trp Lys Ala Tyr Asp Asn Asp Pro Phe His Pro Glu Asn
 30                  35                  40                  45

AAT CCT TTG GGT GTT ATT CAA ATG GGT TTA GCA GAA AAT CAG CTT TCC      193
Asn Pro Leu Gly Val Ile Gln Met Gly Leu Ala Glu Asn Gln Leu Ser
                 50                  55                  60

TTT GAT ATG ATT GTT GAC TGG ATT AGA AAA CAC CCT GAA GCT TCG ATT      241
Phe Asp Met Ile Val Asp Trp Ile Arg Lys His Pro Glu Ala Ser Ile
             65                  70                  75
```

```
TGT ACA CCG GAA GGA CTT GAG AGA TTC AAA AGC ATT GCC AAC TTC CAA       289
Cys Thr Pro Glu Gly Leu Glu Arg Phe Lys Ser Ile Ala Asn Phe Gln
        80                  85                  90

GAT TAC CAC GGC TTA CCA GAG TTT CGA AAT GCA ATT GCA AAT TTT ATG       337
Asp Tyr His Gly Leu Pro Glu Phe Arg Asn Ala Ile Ala Asn Phe Met
    95                 100                 105

GGG AAA GTA AGA GGT GGG AGG GTA AAA TTC GAC CCG AGT CGG ATT GTG       385
Gly Lys Val Arg Gly Gly Arg Val Lys Phe Asp Pro Ser Arg Ile Val
110                 115                 120                 125

ATG GGT GGC GGT GCG ACC GGA GCG AGC GAA ACC GTC ATC TTT TGT TTG       433
Met Gly Gly Gly Ala Thr Gly Ala Ser Glu Thr Val Ile Phe Cys Leu
                130                 135                 140

GCG GAT CCG GGG GAT GCT TTT TTG GTT CCT TCT CCA TAT TAT GCA GGA       481
Ala Asp Pro Gly Asp Ala Phe Leu Val Pro Ser Pro Tyr Tyr Ala Gly
            145                 150                 155

TTT GAT CGA GAC TTG AAA TGG CGA ACA CGA GCA CAA ATA ATT CGG GTC       529
Phe Asp Arg Asp Leu Lys Trp Arg Thr Arg Ala Gln Ile Ile Arg Val
        160                 165                 170

CAT TGC AAC GGC TCG AAT AAC TTC CAA GTC ACA AAG GCA GCC TTA GAA       577
His Cys Asn Gly Ser Asn Asn Phe Gln Val Thr Lys Ala Ala Leu Glu
    175                 180                 185

ATA GCC TAC AAA AAG GCT CAA GAG GCC AAC ATG AAA GTG AAG GGT GTT       625
Ile Ala Tyr Lys Lys Ala Gln Glu Ala Asn Met Lys Val Lys Gly Val
190                 195                 200                 205

ATA ATC ACC AAT CCC TCA AAT CCC TTA GGC ACA ACG TAC GAC CGT GAC       673
Ile Ile Thr Asn Pro Ser Asn Pro Leu Gly Thr Thr Tyr Asp Arg Asp
                210                 215                 220

ACT CTT AAA ACC CTC GTC ACC TTT GTG AAT CAA CAC GAC ATT CAC TTA       721
Thr Leu Lys Thr Leu Val Thr Phe Val Asn Gln His Asp Ile His Leu
            225                 230                 235

ATA TGC GAT GAA ATA TAC TCT GCC ACT GTC TTC AAA GCC CCA ACC TTC       769
Ile Cys Asp Glu Ile Tyr Ser Ala Thr Val Phe Lys Ala Pro Thr Phe
        240                 245                 250

ACC AGC ATC GCT GAG ATT GTT GAA CAA ATG GAG CAT TGC AAG AAG GAG       817
Thr Ser Ile Ala Glu Ile Val Glu Gln Met Glu His Cys Lys Lys Glu
    255                 260                 265

CTC ATC CAT ATT CTT TAT AGC TTG TCC AAA GAC ATG GGC CTC CCT GGT       865
Leu Ile His Ile Leu Tyr Ser Leu Ser Lys Asp Met Gly Leu Pro Gly
270                 275                 280                 285

TTT CGA GTT GGA ATT ATT TAT TCT TAC AAC GAT GTC GTC GTC CGC CGT       913
Phe Arg Val Gly Ile Ile Tyr Ser Tyr Asn Asp Val Val Val Arg Arg
                290                 295                 300

GCT CGG CAG ATG TCG AGC TTC GGC CTC GTC TCG TCC CAG ACT CAA CAT       961
Ala Arg Gln Met Ser Ser Phe Gly Leu Val Ser Ser Gln Thr Gln His
            305                 310                 315

TTG CTC GCC GCC ATG CTT TCC GAC GAG GAC TTT GTC GAC AAA TTT CTT      1009
Leu Leu Ala Ala Met Leu Ser Asp Glu Asp Phe Val Asp Lys Phe Leu
        320                 325                 330

GCC GAG AAC TCG AAG CGT GTG GGC GAG AGG CAT GCA AGG TTC ACA AAA      1057
Ala Glu Asn Ser Lys Arg Val Gly Glu Arg His Ala Arg Phe Thr Lys
    335                 340                 345

GAA TTG GAT AAA ATG GGG ATC ACT TGC TTG AAC AGC AAT GCT GGA GTT      1105
Glu Leu Asp Lys Met Gly Ile Thr Cys Leu Asn Ser Asn Ala Gly Val
350                 355                 360                 365

TTT GTG TGG ATG GAT CTA CGG AGG CTA TTA AAA GAC CAA ACC TTC AAA      1153
Phe Val Trp Met Asp Leu Arg Arg Leu Leu Lys Asp Gln Thr Phe Lys
                370                 375                 380

GCT GAA ATG GAG CTT TGG CGT GTG ATT ATC AAT GAA GTC AAG CTC AAT      1201
Ala Glu Met Glu Leu Trp Arg Val Ile Ile Asn Glu Val Lys Leu Asn
            385                 390                 395
```

```
GTT TCT CCT GGC TCA TCC TTT CAT GTC ACT GAG CCA GGT TGG TTT CGA         1249
Val Ser Pro Gly Ser Ser Phe His Val Thr Glu Pro Gly Trp Phe Arg
            400                 405                 410

GTT TGT TTC GCA AAC ATG GAC GAC AAC ACC GTT GAC GTT GCT CTC AAT         1297
Val Cys Phe Ala Asn Met Asp Asp Asn Thr Val Asp Val Ala Leu Asn
        415                 420                 425

AGA ATC CAT AGC TTT GTC GAA AAC ATC GAC AAG AAG GAA GAC AAT ACC         1345
Arg Ile His Ser Phe Val Glu Asn Ile Asp Lys Lys Glu Asp Asn Thr
430                 435                 440                 445

GTT GCA ATG CCA TCG AAA ACG AGG CAT CGA GAT AAT AAG TTA CGA TTG         1393
Val Ala Met Pro Ser Lys Thr Arg His Arg Asp Asn Lys Leu Arg Leu
                450                 455                 460

AGC TTC TCC TTC TCA GGG AGA AGA TAC GAC GAG GGC AAC GTT CTT AAC         1441
Ser Phe Ser Phe Ser Gly Arg Arg Tyr Asp Glu Gly Asn Val Leu Asn
            465                 470                 475

TCA CCG CAC ACG ATG TCG CCT CAC TCG CCG TTA GTA ATA GCA AAA AAT         1489
Ser Pro His Thr Met Ser Pro His Ser Pro Leu Val Ile Ala Lys Asn
        480                 485                 490

TAATTAAAAA CATTTTTCAA AATATTCATA CCATTCATAT AGTTTTTTTT TTTTTTTTTT       1549

TTGGGTCAAT GTTGACTAAA GTTACGTATA TTTTTTCCAC AGTGGATATG ATGTAAACTT       1609

CATATTTTTT GGTGGGATGG TGATAGATGT AATGTATTTG GTTTTTCCCT TAGGGAACTC       1669

ATACTTATTT ATTAATGAAA TGATTGTGAT TTAT                                   1703

(2) INFORMATION FOR SEQ ID NO:19:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO:19:

Met Gly Phe His Gln Ile Asp Glu Arg Asn Gln Ala Leu Leu Ser Lys
 1               5                  10                  15

Ile Ala Leu Asp Asp Gly His Gly Glu Asn Ser Pro Tyr Phe Asp Gly
            20                  25                  30

Trp Lys Ala Tyr Asp Asn Asp Pro Phe His Pro Glu Asn Asn Pro Leu
        35                  40                  45

Gly Val Ile Gln Met Gly Leu Ala Glu Asn Gln Leu Ser Phe Asp Met
    50                  55                  60

Ile Val Asp Trp Ile Arg Lys His Pro Glu Ala Ser Ile Cys Thr Pro
65                  70                  75                  80

Glu Gly Leu Glu Arg Phe Lys Ser Ile Ala Asn Phe Gln Asp Tyr His
                85                  90                  95

Gly Leu Pro Glu Phe Arg Asn Ala Ile Ala Asn Phe Met Gly Lys Val
            100                 105                 110

Arg Gly Gly Arg Val Lys Phe Asp Pro Ser Arg Ile Val Met Gly Gly
        115                 120                 125

Gly Ala Thr Gly Ala Ser Glu Thr Val Ile Phe Cys Leu Ala Asp Pro
    130                 135                 140

Gly Asp Ala Phe Leu Val Pro Ser Pro Tyr Tyr Ala Gly Phe Asp Arg
145                 150                 155                 160

Asp Leu Lys Trp Arg Thr Arg Ala Gln Ile Ile Arg Val His Cys Asn
                165                 170                 175

Gly Ser Asn Asn Phe Gln Val Thr Lys Ala Ala Leu Glu Ile Ala Tyr
```

```
                    180              185              190
Lys Lys Ala Gln Glu Ala Asn Met Lys Val Lys Gly Val Ile Ile Thr
            195              200              205
Asn Pro Ser Asn Pro Leu Gly Thr Thr Tyr Asp Arg Asp Thr Leu Lys
        210              215              220
Thr Leu Val Thr Phe Val Asn Gln His Asp Ile His Leu Ile Cys Asp
225              230              235              240
Glu Ile Tyr Ser Ala Thr Val Phe Lys Ala Pro Thr Phe Thr Ser Ile
                245              250              255
Ala Glu Ile Val Glu Gln Met Glu His Cys Lys Lys Glu Leu Ile His
            260              265              270
Ile Leu Tyr Ser Leu Ser Lys Asp Met Gly Leu Pro Gly Phe Arg Val
        275              280              285
Gly Ile Ile Tyr Ser Tyr Asn Asp Val Val Arg Arg Ala Arg Gln
290              295              300
Met Ser Ser Phe Gly Leu Val Ser Ser Gln Thr Gln His Leu Leu Ala
305              310              315              320
Ala Met Leu Ser Asp Glu Asp Phe Val Asp Lys Phe Leu Ala Glu Asn
                325              330              335
Ser Lys Arg Val Gly Glu Arg His Ala Arg Phe Thr Lys Glu Leu Asp
            340              345              350
Lys Met Gly Ile Thr Cys Leu Asn Ser Asn Ala Gly Val Phe Val Trp
        355              360              365
Met Asp Leu Arg Arg Leu Leu Lys Asp Gln Thr Phe Lys Ala Glu Met
        370              375              380
Glu Leu Trp Arg Val Ile Ile Asn Glu Val Lys Leu Asn Val Ser Pro
385              390              395              400
Gly Ser Ser Phe His Val Thr Glu Pro Gly Trp Phe Arg Val Cys Phe
                405              410              415
Ala Asn Met Asp Asp Asn Thr Val Asp Val Ala Leu Asn Arg Ile His
                420              425              430
Ser Phe Val Glu Asn Ile Asp Lys Lys Glu Asp Asn Thr Val Ala Met
            435              440              445
Pro Ser Lys Thr Arg His Arg Asp Asn Lys Leu Arg Leu Ser Phe Ser
        450              455              460
Phe Ser Gly Arg Arg Tyr Asp Glu Gly Asn Val Leu Asn Ser Pro His
465              470              475              480
Thr Met Ser Pro His Ser Pro Leu Val Ile Ala Lys Asn
                485              490
```

(2) INFORMATION FOR SEQ ID NO:20:

(i) SEQUENCE CHARACTERISTICS:
        (A) LENGTH: 9060 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(2704..2880, 2968..3099, 3183..3344,
           3810..4376, 4463..4903)

(xi) SEQUENCE DESCRIPTION: SEQ ID NO:20:

```
CACATTGGTT TGGAGAGAGAG GAACGAGTGC AACGAGGATG CTGGGCTCTG AAAAGGGGTG      60

GATTGTGAGA TCCCACGAAC GAAACATTCT TTGTAAGGGT GTGAAAACCT CTCCCTAGCA     120
```

-continued

```
TACTCGTTTT AAAAACCTCA AGGAGAAGTA CAAAAAGAAA AGCCGAGGAA GGATTTCAAA      180

AAGTTAGAAC TTCATTAAAA ATGAAAGCAC AAAGAAGAGA ATTATTAGTA ATGTTCTTGC      240

ACAAGTATAA GTTGAAAAAC TAATTCTATC AAGTGTGAAT CCACACTCAT CTTTCAAAAT      300

TAAGCAAACA AAACGAGTCA TGCTTGCCTT CTCCAAATTT TATCACTAAT AGTGTGACAC      360

TCAATGTCCC ACTTACCATT CTTGGCCCCC ACAACCACCT CCAAGAAACA ATAACTTTTA      420

CTACCCAACC CCCAATTTTG GAACAAAAAT GAGTCAAATA TATGAACAAT AACATCGTGT      480

TTCTTCTTAC CGACTCGGTT GAATATGCAA CGTTTATAAT ATACTTCAAG AAATTTTGAG      540

ACATTACTCA AATAAAGTCT CTCACAAAAA TAGAATATCT TTATACTAGT ATAATGAATT      600

GTCCACTTCG ATTTAAATCC TCTAAAGTTC ACTTTCGTAA ATGGCTTAAT GAACAGATTT      660

ATTAGGATCA AATTCAAAAG TTGAATGAGA CTAAATAGAT ATAATAAAAT CTGATTGTTG      720

CATGAAGTAT GCAGCTCAAA GATGATGTTT TGCGAAAAAA ATGCAAACTA AGCATGAGTG      780

CTTCTGTAAA AAAAAAATGA AAAAGAAAAA TATATATCGT ACTATCAAAA ACATTGTCCT      840

TACTTAGACA GCTCAAAACT TTTCATATTC CTATATTTGT TTATATTGAA ACTTTTTCCA      900

TTTCATTTGT TTAAATCATA TTTGGTTGTT TAAATAAGAA TACTGTAACA GTCCAAGCTC      960

ACTGTTAGTA GATATTGTCT TCTTCGGACT TTTCCGGCTT CTTCTCAAGG TTTTAAAATG     1020

TGTCTACTAG GGAGAGATTT TCACACACTT ATAAAGAATG ATTCGTTCTC CTCTTCAACT     1080

AATGTAAAAT CTCACAAATA CTAAACAATT GGAATTTATT AGGATCAGAA TCAAAAGTTG     1140

AGAGATATAG TGGAAACGAC CGTCGAGATT AAATAGATAC AATCAAGTTT GATCATTGTA     1200

CTAAATAAGT AGCTCGGAGA TGTATACGAG AAAAGAAAGC GCACTATAAA AATGAGGTAA     1260

AAAGTGGTCG GAGTAGTATA CAATGTGAGA GGTATGCAAA TATACGTATT TCCTTTAGGT     1320

GAAAAGTCC GAAACCACAC CAAAAAGCAC TCTTAAAAAT GTGCCAAAAC GGTTCTATCA     1380

CTCAATGTCA AATCTTTCAA TTCAAAAGCA TGTGGGTATT GATTGCTGCT TCCAACGAAG     1440

CTTCATTCTC CTACTTGTTA CACACACACA AACTCGTTGT TCATGACCAA TTCTATCCCC     1500

TTTCCCATGT CATCCTCCAA ACTTTTGACC CTTCAATTTG GTCCCCTAAC CCTTTTTTTC     1560

ATCACATGGG ATGCAACCAT TTTGATTTAG TCTACGACAT TCTTTTCATT TATCTACTTA     1620

CGCCCTCCGA GGGAACAGTT GGATTGAAAG TTCGACTTCT TAGCCTTGGA GATGAGAGAA     1680

CCGGTACACT CCATGAATTA CAAAATTTAA ATCTCTAATC CTAACTTTGG AGCTACGTAT     1740

GACCTTTGTA TCTTTGTAAG AGCTTTTCTC AATGCTAACA AATATTGTCT ATTTCAGCTG     1800

GTTACGCATT GTCGTCTGCT TCCCGATTTT AAAATACGTC TATTAAGGAG AGGTTTTCAC     1860

ACCCTTACTA GAAACGTTTC GTTCTCCCTC TAAATGTGAG ATCTCACCGT AACTAGCTAG     1920

AGATTAAAAT GTTATTATAG CTAGAGATTC AACCAAACAT AACACAAAAA GATAATCATA     1980

GGGATCAACA AAATTCATAA CTAGTTCTTA TAATATGCAA TAAAATTCAA ATTAATTATG     2040

CATTAGAAGA AAATAAAAAA ACAATTAAGA TAACCCAAAA ATTAATTTCC TTCTACCTAT     2100

AAATCTATAA TAAGATTCGA GTATTAGATT AAAATTATCC CAAATCAAGA ACATAAATTA     2160

AGATCATAAA CGTAATATAT TTTAATCGAG AACGTAAATA CAGGACATAC AGATTAAGAA     2220

TTCAAATATT TTGAATTATA ATATGAATTT GATAGAAAAT AAAACAAAAA CTAAAAAATA     2280

AACTTAGTAA TTATGATGAG ATAAAAGAAG ATTTTGTGAC ATGATATTTT TGTTATGTTC     2340

CAAATCTAGA GTATGCCTCC ACACATGCGG GGTCGGGTCG GCTGTGTGTG TGGCTCGTCT     2400

GCTTGCTTGA ATCACAACCC TCCACGCATG CAATTACGCC CTCCTTGACT CAAACCCCAT     2460

TTTAACTCTC TCTTCCATTT TTATTATTTT TTCTTTAATT TTTTTCATCA CTGTTTTTTT     2520
```

```
TTTTTTTTTT TTTCATGGTT TGAACTTTGA AAAGTTGAAT TTTCTACACG TTTGATTTTC    2580

CTGGTAAGAA CTTGATCTTG TTGGATCTTC CTCACTGCTT ATAAATTCAC TCAATTCTCT    2640

TCTTTCTTTC CTATCTTACA ACCCAAAACC TCTCATTTTT AGGCACATCT CAACAACTTT    2700

CAA ATG GGG TTT CAT CAA ATC GAC GAA AGG AAC CAA GCT CTT CTC TCG      2748
    Met Gly Phe His Gln Ile Asp Glu Arg Asn Gln Ala Leu Leu Ser
    1               5                   10                  15

AAG ATC GCC CTC GAC GAT GGC CAT GGC GAG AAC TCC CCG TAT TTC GAT      2796
Lys Ile Ala Leu Asp Asp Gly His Gly Glu Asn Ser Pro Tyr Phe Asp
            20                  25                  30

GGG TGG AAA GCT TAC GAT AAC GAT CCG TTT CAC CCT GAG AAT AAT CCT      2844
Gly Trp Lys Ala Tyr Asp Asn Asp Pro Phe His Pro Glu Asn Asn Pro
                35                  40                  45

TTG GGT GTT ATT CAA ATG GGT TTA GCA GAA AAT CAG GTTTGGTATA           2890
Leu Gly Val Ile Gln Met Gly Leu Ala Glu Asn Gln
            50                  55

TCGTGTTTTC GTGTTTTTCT TATATGACTT CACGTTTGAA AATTTCGCTA ACTTTGTTTT    2950

TTTGTGAATT TCGATAG CTT TCC TTT GAT ATG ATT GTT GAC TGG ATT AGA       3000
                Leu Ser Phe Asp Met Ile Val Asp Trp Ile Arg
                            60                  65                  70

AAA CAC CCT GAA GCT TCG ATT TGT ACA CCG GAA GGA CTT GAG AGA TTC      3048
Lys His Pro Glu Ala Ser Ile Cys Thr Pro Glu Gly Leu Glu Arg Phe
                75                  80                  85

AAA AGC ATT GCC AAC TTC CAA GAT TAC CAC GGC TTA CCA GAG TTT CGA      3096
Lys Ser Ile Ala Asn Phe Gln Asp Tyr His Gly Leu Pro Glu Phe Arg
            90                  95                  100

AAT GTACGAGATA TGATATACTC TTAACTATAT CTGAACTCAA AAGGTTAAGT           3149
Asn

TGATGGGTTA TGATAAAATT TCTTTCTTGT CAG GCA ATT GCA AAT TTT ATG GGG     3203
                                Ala Ile Ala Asn Phe Met Gly
                                            105                 110

AAA GTA AGA GGT GGG AGG GTA AAA TTC GAC CCG AGT CGG ATT GTG ATG      3251
Lys Val Arg Gly Gly Arg Val Lys Phe Asp Pro Ser Arg Ile Val Met
                115                 120                 125

GGT GGC GGT GCG ACC GGA GCG AGC GAA ACC GTC ATC TTT TGT TTG GCG      3299
Gly Gly Gly Ala Thr Gly Ala Ser Glu Thr Val Ile Phe Cys Leu Ala
            130                 135                 140

GAT CCG GGG GAT GCT TTT TTG GTT CCT TCT CCA TAT TAT GCA GGG          3344
Asp Pro Gly Asp Ala Phe Leu Val Pro Ser Pro Tyr Tyr Ala Gly
            145                 150                 155

TGAGTTCTTC TTTCATTTCC TTTTGTTCAC TTTTCTTTAA GTCAATATTC CTTAGTCCAA    3404

CCTGGAAAGA GAAAGAAGAG AGAGAAAGAA ACCATTTGAC AAATTAATAA CTCTACAAAT    3464

TCTCTTTGAA AGTTTGATGT TTTTTTTAAG GTCAAAACTT CAACCATTCT CTTGCAAAGA    3524

AAAAAAAAAG TCATAATTAT AATGAAGAAA AAACTAGGCC ATCCAAGTCA ACCTTTTTAA    3584

ATGCTAATAA AGTCAATATG CTTTGTAGGT TTAAAAAACA ATAAATTGCT TAATCATTTC    3644

TTAAATTTTA ATTAAACCCT TTTGACTTTA TCATTACCCA TTTACATAAA TTAACAATTT    3704

ATTGCTCTTT TTGTAGTAAA ATTAATAAAA AAAAAGTTAG GTGTAAACGT ACAGTATTAT    3764

GTTATTGTAA AAATACTGAG AAGTGTTAGT ATGTTGTTTT TCAGA TTT GAT CGA        3818
                                                Phe Asp Arg
                                                        160

GAC TTG AAA TGG CGA ACA CGA GCA CAA ATA ATT CGG GTC CAT TGC AAC      3866
Asp Leu Lys Trp Arg Thr Arg Ala Gln Ile Ile Arg Val His Cys Asn
                165                 170                 175

CGC TCG AAT AAC TTC CAA GTC ACA AAG GCA GCC TTA GAA ATA GCC TAC      3914
Arg Ser Asn Asn Phe Gln Val Thr Lys Ala Ala Leu Glu Ile Ala Tyr
```

```
                Arg Ser Asn Asn Phe Gln Val Thr Lys Ala Ala Leu Glu Ile Ala Tyr
                            180                 185                 190

AAA AAG GCT CAA GAG GCC AAC ATG AAA GTG AAG GGT GTT ATA ATC ACC              3962
Lys Lys Ala Gln Glu Ala Asn Met Lys Val Lys Gly Val Ile Ile Thr
        195                 200                 205

AAT CCC TCA AAT CCC TTA GGC ACA ACG TAC GAC CGT GAC ACT CTT AAA              4010
Asn Pro Ser Asn Pro Leu Gly Thr Thr Tyr Asp Arg Asp Thr Leu Lys
    210                 215                 220

ACC CTC GTC ACC TTT GTG AAT CAA CAC GAC ATT CAC TTA ATA TGC GAT              4058
Thr Leu Val Thr Phe Val Asn Gln His Asp Ile His Leu Ile Cys Asp
225                 230                 235                 240

GAA ATA TAC TCT GCC ACT GTC TTC AAA GCC CCA ACC TTC ACC AGC ATC              4106
Glu Ile Tyr Ser Ala Thr Val Phe Lys Ala Pro Thr Phe Thr Ser Ile
                245                 250                 255

GCT GAG ATT GTT GAA CAA ATG GAG CAT TGC AAG AAG GAG CTC ATC CAT              4154
Ala Glu Ile Val Glu Gln Met Glu His Cys Lys Lys Glu Leu Ile His
            260                 265                 270

ATT CTT TAT AGC TTG TCC AAA GAC ATG GGC CTC CCT GGT TTT CGA GTT              4202
Ile Leu Tyr Ser Leu Ser Lys Asp Met Gly Leu Pro Gly Phe Arg Val
        275                 280                 285

GGA ATT ATT TAT TCT TAC AAC GAT GTC GTC GTC CGC CGT GCT CGG CAG              4250
Gly Ile Ile Tyr Ser Tyr Asn Asp Val Val Val Arg Arg Ala Arg Gln
    290                 295                 300

ATG TCG AGC TTC GGC CTC GTC TCG TCC CAG ACT CAA CAT TTG CTC GCC              4298
Met Ser Ser Phe Gly Leu Val Ser Ser Gln Thr Gln His Leu Leu Ala
305                 310                 315                 320

GCC ATG CTT TCC GAC GAG GAC TTT GTC GAC AAA TTT CTT GCC GAG AAC              4346
Ala Met Leu Ser Asp Glu Asp Phe Val Asp Lys Phe Leu Ala Glu Asn
                325                 330                 335

TCG AAG CGT GTG GGC GAG AGG CAT GCA AGG TTTGTTAAAC TACACCATTA                4396
Ser Lys Arg Val Gly Glu Arg His Ala Arg
            340                 345

TTATTTGTGG GATTGAAAAG CATTACTTTT TGCAATTAAT TTAAGAATGT ATTAATCAAA            4456

TTCAGG TTC ACA AAA GAA TTG GAT AAA ATG GGG ATC ACT TGC TTG AAC               4504
       Phe Thr Lys Glu Leu Asp Lys Met Gly Ile Thr Cys Leu Asn
               350                 355                 360

AGC AAT GCT GGA GTT TTT GTG TGG ATG GAT CTA CGG AGG CTA TTA AAA              4552
Ser Asn Ala Gly Val Phe Val Trp Met Asp Leu Arg Arg Leu Leu Lys
                365                 370                 375

GAC CAA ACC TTC AAA GCT GAA ATG GAG CTT TGG CGT GTG ATT ATC AAT              4600
Asp Gln Thr Phe Lys Ala Glu Met Glu Leu Trp Arg Val Ile Ile Asn
            380                 385                 390

GAA GTC AAG CTC AAT GTT TCT CCT GGC TCA TCC TTT CAT GTC ACT GAG              4648
Glu Val Lys Leu Asn Val Ser Pro Gly Ser Ser Phe His Val Thr Glu
        395                 400                 405

CCA GGT TGG TTT CGA GTT TGT TTC GCA AAC ATG GAC GAC AAC ACC GTT              4696
Pro Gly Trp Phe Arg Val Cys Phe Ala Asn Met Asp Asp Asn Thr Val
    410                 415                 420

GAC GTT GCT CTC AAT AGA ATC CAT AGC TTT GTC GAA AAC ATC GAC AAG              4744
Asp Val Ala Leu Asn Arg Ile His Ser Phe Val Glu Asn Ile Asp Lys
425                 430                 435                 440

AAG GAA GAC AAT ACC GTT GCA ATG CCA TCG AAA ACG AGG CAT CGA GAT              4792
Lys Glu Asp Asn Thr Val Ala Met Pro Ser Lys Thr Arg His Arg Asp
                445                 450                 455

AAT AAG TTA CGA TTG AGC TTC TCC TTC TCA GGG AGA AGA TAC GAC GAG              4840
Asn Lys Leu Arg Leu Ser Phe Ser Phe Ser Gly Arg Arg Tyr Asp Glu
            460                 465                 470

GGC AAC GTT CTT AAC TCA CCG CAC ACG ATG TCG CCT CAC TCG CCG TTA              4888
Gly Asn Val Leu Asn Ser Pro His Thr Met Ser Pro His Ser Pro Leu
```

```
              475                 480                 485
GTA ATA GCA AAA AAT TAATTAAAAA CATTTTTCAA AATATTCATA CCATTCATAT        4943
Val Ile Ala Lys Asn
    490

AGTTTTTTTT TTTTTTTTTT TTTGGGTCAA TGTTGACTAA AGTTACGTAT ATTTTTTCCA      5003

CAGTGGATAT GATGTAAACT TCATATTTTT TGGTGGGATG GTGATAGATG TAATGTATTT      5063

GGTTTTTCCC TTAGGGAACT CATACTTATT TATTAATGAA ATGATTGTGA TTTATGAATT      5123

ATAATTGTAT ATTTTTCTTT AAAAGTATTT TATTGCAAAA ATAAATAAGT ATTATGAGGA      5183

ATTGTAATTG AATGGAAAAG GTATAGAGTC AAAGGGAATA AACATATATT TTATTTTTTC      5243

TTATGGAAGT TTTGTTCATA CTTAAAATGT ATTATATTTA TGGAAACTTT ATTGACTTTA      5303

AAGATTTGGG ACAAAGGGTA TGATATGTTC AAGTTTATTA CGTTTGTTGG ATTAGTCACT      5363

TCATTGACAT TGATGTTTTT GTTGTCATAT TTTGTCATTA TTACCACACT TTTTTTGTCT      5423

AAAAGCAAGC TTATATTCAA TGAGGATGCA AAAATACTTT ATAAATGGTT TGTCTATGTT      5483

TGGGTCTCAT AGATGCACCT TTATACAAAA CCGTTCATAC AAACAACCAA ATTATATATG      5543

TCGATCCAGA AACGCTATAT ACAAAGTCAA ATACTTTACT GACAAACTAC GATCGTTCAC      5603

CGTCCTATAA CATCTTTTTC GAGTCTAACC ATTCAATGTT ACATCGTTTT TTTTTTTTGT      5663

TTGGTAAATA CTTTTTCTTT TTGCTTTGTT AAATTATAAC TTGGGTTTGT TATGTGCAAT      5723

TTATCTATTT ATATGCAGTT GACTTAGTTA GCTTGTATTG TTCTAGTAGT GAATGACTAG      5783

TATCTTGAGT TGAGGGGCTA CCTCATAAAA TCTAGTAGGA CGACATGATA GCGTGGATCT      5843

GAATATTATT TATGGAAGGT TAATTAACAT ACTCTTCTAC AAGACCATAA AGTCATACTA      5903

AATTTGGGGG AGTGACCTCG TGTACTTGCC AGCTAGTAAG TTACGTGTAT GGTCCCTCAC      5963

CCTCCCTCAC CCTCTAGTCA TTTCGACTAG ATAAAGACAC ATGGTTGCCT TGACGTGATA      6023

TATTATTTGG CCCAGGCCAA ACTTGATGGT ACAACTGTTG TGCTCCTACC ACTAAAATAA      6083

CTGATCTAGG TCACACATGG CTATTAGGTT TGTTAAGCTT TCTTAATCAT CCTTGGATGC      6143

TTCGAGGTTT ATTAGGTTTT CAGGATGTCT AGATTGTTTA AATCTCGAAC TCTCATTTCT      6203

AGGAACTCTG GACTGCACCT CTAGGCTAAT CTAGTTTATA GGAGCACTAT GGTCCTGACC      6263

ACTGATCTTC ACTCACGATC CTAGGGTACT CGTTCTAGAA TGGGTGTTAG AGTTAGAACA      6323

GTTTCACGTT GACCTAGGTC AGAACGTTTT CATTAGACCG AACACGCTAA GATCGTGAGC      6383

GACAATCAAT GGTCAAGATT ATAGTGCTCC TATAAACTAG ATTAGTCCCA AGGTGCAGTC      6443

CATTGTGCAT AGAAATGAGA GTTGGAGATT TAAACAACCT AGATGTCCTA AAACCTAGTA      6503

AACCTCGAAG GCATCCAATG ATGACTAAGA AATCTTAACA AGGCTATTAG CAGTGTGAAC      6563

GGTGTCATGA GAGCATTTGC CTCCTATCTT CTTCGGTACG TCATTAGCTC TATCAATGAC      6623

CTAGGTCAGT TCTTTTAGTG GCGTGTCAAG TGGTAGGAGC ACAAGAGTTG TACCATCAAG      6683

CTTGGCCTAG GCCAAATAGT ATAGCACGTC GAGGAAACCA TGTGTCTTTA TCCAGTCAAA      6743

ATGACTAGGG GACTTCTAAA AAAGGTCTCT GCACCATAAA CTGATCCCGA GAGAGGGTGA      6803

GGGACCATAC AGGTAACTTA GTAGCTGACA AGCACACGAG GTCGCTCCCC CAAATTTAGT      6863

GACTTTATGG TCGTGGAGAA GAGTATGTTA GTTAACCTTC CATAAATAAT GTTCACATCC      6923

ACGATATCAT ACGGTCGTAT TAGATTTTAT CACTATTGTG TTTGTATGCA TGGTTTTGCA      6983

TAAAGGTAGA TCTGTAGCAG ACAGTTTGCG TATTGGAATG GCACCGCCAT TGTTAAGAAG      7043

GTGGACACCG TGTGGCCGAA CTCTGATATG AACAAAATGA AGACAAGACA AGTGGACATA      7103

TATAATCCCA TGAACCAGGT TTGGACGTAA AACAATATAA TGCCTGTCGT TTTCAGCTGC      7163
```

```
CCATTTCGAC AAACACTCAT CTCCATTGTC CAGTGGGTTC TCCTTATATT CAACAAAAAT    7223

TTGTTTGAAT GTTTAAAGAT AAAAATTTGA CTTTTAAACC AAAACCGTGA TAACTTAGGA    7283

TGGTGTGATA ATATTTAAGT CCCAATTTTC ATTTGAATTT TAAAATTGTT TGAAAAAAAC    7343

ATATATATTT TTTATTAAAA TAAAAGATGA AGGTTGACAT CGAAATCTTA CGAGATAATC    7403

CTTATCGGCG TTCTAACGAA ATTAATACTA TCATGGTCTT ATTCTAAAAG TCTATGTCTT    7463

TTATGTATTG TTTAATCAAA TATGAATTAC TTGGAAAATG GGATCTTGTG TGTTTGACTT    7523

GAGTTTGAAC AATTGTCAAA ATGTTAGCTG TAAAGTAGTC GCCCTTCTCA TCCATTTAGT    7583

TTAAAGGATG TTTCGAGTTT AAATTTTCTT CTCTCACTCC AAGGGAGAAT CATCTATGTC    7643

ATTATATATG CAAGGGTGGT TTGATTATGA TAGATAGATG TACATTTAAC CTGTTAAGTA    7703

GGGGTCATGC GGATCAGAGA TCTACTTTAA ATGGCGTAGA AAATCCTGTT TAAACAGGGT    7763

CGGGAATAAG GATTATCATA CTCTACCCTG CTCACTTCTT ATGTATAAAT ATAGATAGAA    7823

TAAATGAGAA ATTTTATGGA AATGAAAATT GAAGTAGGAG GAAGGCGCAG GGACGGGTAA    7883

GACTTCCCCG TTCTCACGCT TCCCCATAAA CATCATACTT CAACTTTGAT GAAGTATGAA    7943

ATTTTGTTTG GTGGATATCC AATAAGTCTC ATTGCACTAA ACAAAGCCAG GGAAGAGTTC    8003

ATAAATAAGA CGTAAAGTTG TGGTCTCCAA CACGTAAAAC ATAGTTACTC CTCTTGATTT    8063

CCCATGTAAT TGAGAATTTA GAGCTTTAGT GTGTTTAGAC GAGGAAGATT GCTTTCACTG    8123

AACACTGAGT TGTTCCCTAA ATCTATTTGT TACAACGAGG TTTATCACTG CTTAAGTGAT    8183

GTAATTTAGG TTTTAATTTC TAGAAAACGT GACTATGTGT AATGTCAGAC TTGTTAGGAC    8243

TTTGAGCATA AGCTCTCATG TCTTTGATTT GAACTTTCTT AAAAAGTTTC ATACCAATGG    8303

AGATGTATTC CTCGTTTATA AACTCAAGAT CATTCGCTAA CGTGGGACTT CCTTCCGATA    8363

ATCCTCAACA AAACTCAGTA TTAACTTCAG TTTGTTTGGT GAAGTGTTAG ACCCTTTCTT    8423

TAATCACATG CAATCATGGT GAGATTTGTC TTTTCATAAA AATATTATGG CCTTATATTC    8483

TATTTCCAGT CTGAACAGAG TTGAATGAGT TGTACTTCTC TACAATCAGC CCATGCACAC    8543

ATACGAGAAC CCACCAGACG GACTCATGTC TAAACAAAAG GGAAGAATCA CATTAGAGGG    8603

TGAAGAAGAA ACATTTTACA CAAGTGCTCG GAGCAACAAT ACGTCATTTA CCAAACATGG    8663

ATATAAAAAT GGTGACAAAG GAAGAAGCTA TCAAGCACAA TCAGGGAGAG CTCAGAAGAA    8723

CGACAACAAT AACTCTCAAG TGAAGAGATT TTGGGGTATT TACTACAACT GCGGAAAAAG    8783

GGCTACATGT CCAGAGATGG TTGGTCTAAG AAAATTTTTG TTGAAAGCAA TGTGGCAACA    8843

TCCAAAAAGG AGATGGAAGA TAAATGGGAT GCAGAGGCAA TATGTGTCGT AGAAGAAGAC    8903

GAGCTAGCAC TTATGGTAAT AAAGAGAGAA CATATTGATT ATGAGGATGA CTGAATCATT    8963

GATTCAGGAT GCTTAAACCA CATGATTAAC AATCAGAGTG GAACAATTGG ATGCGGAGTG    9023

GCCCTCAGAG AATGAAGTAT TTCAAGGCTT GGAATTC                            9060
```

(2) INFORMATION FOR SEQ ID NO:21:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO:21:

```
Met Gly Phe His Gln Ile Asp Glu Arg Asn Gln Ala Leu Leu Ser Lys
 1               5                  10                  15
```

-continued

```
Ile Ala Leu Asp Asp Gly His Gly Glu Asn Ser Pro Tyr Phe Asp Gly
             20                  25                  30
Trp Lys Ala Tyr Asp Asn Asp Pro Phe His Pro Glu Asn Asn Pro Leu
             35                  40                  45
Gly Val Ile Gln Met Gly Leu Ala Glu Asn Gln Leu Ser Phe Asp Met
             50                  55                  60
Ile Val Asp Trp Ile Arg Lys His Pro Glu Ala Ser Ile Cys Thr Pro
 65                  70                  75                  80
Glu Gly Leu Glu Arg Phe Lys Ser Ile Ala Asn Phe Gln Asp Tyr His
             85                  90                  95
Gly Leu Pro Glu Phe Arg Asn Ala Ile Ala Asn Phe Met Gly Lys Val
            100                 105                 110
Arg Gly Gly Arg Val Lys Phe Asp Pro Ser Arg Ile Val Met Gly Gly
            115                 120                 125
Gly Ala Thr Gly Ala Ser Glu Thr Val Ile Phe Cys Leu Ala Asp Pro
            130                 135                 140
Gly Asp Ala Phe Leu Val Pro Ser Pro Tyr Tyr Ala Gly Phe Asp Arg
145                 150                 155                 160
Asp Leu Lys Trp Arg Thr Arg Ala Gln Ile Ile Arg Val His Cys Asn
            165                 170                 175
Arg Ser Asn Asn Phe Gln Val Thr Lys Ala Ala Leu Glu Ile Ala Tyr
            180                 185                 190
Lys Lys Ala Gln Glu Ala Asn Met Lys Val Lys Gly Val Ile Ile Thr
            195                 200                 205
Asn Pro Ser Asn Pro Leu Gly Thr Thr Tyr Asp Arg Asp Thr Leu Lys
            210                 215                 220
Thr Leu Val Thr Phe Val Asn Gln His Asp Ile His Leu Ile Cys Asp
225                 230                 235                 240
Glu Ile Tyr Ser Ala Thr Val Phe Lys Ala Pro Thr Phe Thr Ser Ile
            245                 250                 255
Ala Glu Ile Val Glu Gln Met Glu His Cys Lys Lys Glu Leu Ile His
            260                 265                 270
Ile Leu Tyr Ser Leu Ser Lys Asp Met Gly Leu Pro Gly Phe Arg Val
            275                 280                 285
Gly Ile Ile Tyr Ser Tyr Asn Asp Val Val Val Arg Arg Ala Arg Gln
            290                 295                 300
Met Ser Ser Phe Gly Leu Val Ser Ser Gln Thr Gln His Leu Leu Ala
305                 310                 315                 320
Ala Met Leu Ser Asp Glu Asp Phe Val Asp Lys Phe Leu Ala Glu Asn
            325                 330                 335
Ser Lys Arg Val Gly Glu Arg His Ala Arg Phe Thr Lys Glu Leu Asp
            340                 345                 350
Lys Met Gly Ile Thr Cys Leu Asn Ser Asn Ala Gly Val Phe Val Trp
            355                 360                 365
Met Asp Leu Arg Arg Leu Leu Lys Asp Gln Thr Phe Lys Ala Glu Met
            370                 375                 380
Glu Leu Trp Arg Val Ile Ile Asn Glu Val Lys Leu Asn Val Ser Pro
385                 390                 395                 400
Gly Ser Ser Phe His Val Thr Glu Pro Gly Trp Phe Arg Val Cys Phe
            405                 410                 415
Ala Asn Met Asp Asp Asn Thr Val Asp Val Ala Leu Asn Arg Ile His
            420                 425                 430
```

```
Ser Phe Val Glu Asn Ile Asp Lys Lys Glu Asp Asn Thr Val Ala Met
    435                 440                 445

Pro Ser Lys Thr Arg His Arg Asp Asn Lys Leu Arg Leu Ser Phe Ser
450                 455                 460

Phe Ser Gly Arg Arg Tyr Asp Glu Gly Asn Val Leu Asn Ser Pro His
465                 470                 475                 480

Thr Met Ser Pro His Ser Pro Leu Val Ile Ala Lys Asn
                485                 490
```

(2) INFORMATION FOR SEQ ID NO:22:

(i) SEQUENCE CHARACTERISTICS:
        (A) LENGTH: 7587 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(2637..2813, 2901..3032, 3120..3281,
            4540..5106, 5193..5636)

(xi) SEQUENCE DESCRIPTION: SEQ ID NO:22:

```
AAGCTTAATG ACTACGAATC AAGCTACTTA TCATCCATTA ATCATTTAAT ATACCTCAAT      60

ACGTCTAACT CAATCATGTT CTCATCATAT TTTTGACGTT TAACTGTTCG TGGGTTGGAT     120

TGGGTTGAAT TGAAACGGTT CTTAGATCTA ACTAAATTGT TCGAGTTTCA ACTTTGATTA     180

AATAATGAAC TCAACTCAAC CCAACCGAAT CATAAAGTTT TGGATTGAAC TTGTTTGGGT     240

AACCTAATTC TATACAAGCA AGTTCGTAAT CCAAATGAAA CTATATATAT TGAGTTAAGC     300

TGATCGAATT TTTCGAATTC AAATTTTGTT GATTATCTTC TCATTGTTCT ATCAACCTTT     360

GTATAGTTCT TTGTCACAAA AACAAATCCT CACCGACCAT ACTATTAATT GTGATCTAAC     420

GTAAAAAAAA CGTTTGTTTA TGTAACACTT TAATGATCAT ATTTCTAGAT TCACTAAAAA     480

GATCATGTAC AAACAAAATA GTCGATCACA AAGACTATAT TCAGAAGCCA ATTTTTATTT     540

TAATTCGACT CGTTTTGAAT CTGTGTTTTT TTTTTTTTTT TTTTGAATCT AGACGAAGAA     600

TAACAAAAAT CTCTCCAAAA TTCGATCTCC ATTGACTTTT TGGTACCGAT CCATTAATGA     660

ACGTGGGTTT GATTTTAGAA GCCCTATTGA ATTTTCTTGT TTGAATTTAT TAATCTTCTT     720

TGATTGCGAT TGACCAATTG ATTTGGTTGA GACTCAAAAT CCCAAAACAT ACAAAAGTCT     780

TAATGTAACA ACGAACTCAT GAACATATCG TTAATGCATA CATATCACAA AAGCGTTTCA     840

ACACATTTGA GTAAAAGTGA CGAAAAGCTG AACTTTTTA AAACAAACTT CGAACCTTTT     900

AACTTTTTAT ATGAATTGAA CATAACAACA AAATGTTAAC ATTGTATTGA CATCATTATA     960

TTTAACAATT TTCCACCGAC CATACTACTA ATTGTACTCT TAAATGGAAG TTCTTATTTT    1020

CGTTCTCAAA TATTCTAATC GTTTTTATTC ATTCATCGTT CAACAGCTAC TCTTATGCAT    1080

TATTTTCTTC CGTTTATCAA TTTACATTTC TAGATCCACT AAAAGTTCAT AAACAAACAA    1140

AATAGTCGAT CCCAGTCGAT CCCACCGACC ATCTTCCTAT AGAAGCCAAT TTTTATTTTA    1200

ATTCGACTCA TTTTGAAATT ATGTTATTTC CCCAAAATTC ATCTCCTTCA ACTTTTTGGT    1260

GCCAATCCAT TAATGAACGT GAGGTTGGTT TAGAAGTCCA TTGGGTTTTG TTGTATGATT    1320

TAATTATTTT CTTTGCCAAC TTTTTCGTGG TCAAGCCCAT CGATTTAAAT ATTTATTATT    1380

TGTTTCTTAT CATTTTCTTA TCGGCTAATA CGATAGTTTT CTATTTGAGC GAGAAAAAGC    1440

GTGCTAGGAG ATTCATATTG GTTTGTGGGA TTGTCTAAAC GTGACCATTT GTAGGAGATG    1500

CAAGGGAATA ATGAGACATA CATGTGCTGA ATTCAGATTC AGAATTGTTT CAAATTCCGA    1560
```

```
GCATGGATAC TTCGTAAAAG TTGAAAAACC ATGCACACCT CGAACGAGTG AACAATAATA    1620

TTGCCTTTCT TTCGCCCCCA TACTCAAGAA AGCTTGGGAC GCTACATAAG AAGTTAAATT    1680

AGGTATCATT GAAATAGGAT ATATTTGTAC TTGTATGATG TATTGTCATA CTTCTCGACT    1740

TCATCTAATT ATAGAGTTTC GAAGTTTTCA TACTTTCCCA TTTTTGTTGA AAATGTATTA    1800

TTGCACGAGT GCAGTTGGAT TAAACATCTG AACCCCAACG AGAATTAATT TTCTCGAATT    1860

TTTCATTTAC GATCAAGCTT CCAGAATTTT ATTGAAAACC TTAGAGATCG AATTTAGGAA    1920

TACAGTAGAA GAGAATGATG CTCGGAATGT TTTCTAGAAG CTCGAAAAAA TATAAAATAA    1980

AATCGTAGAA AATAAAAAAA TGTGTGGTCA AAGTCAATAG AATTTTGCCC CTCCTAGTAT    2040

TTTGGAGACC CTCGAAAAAC CCGAGTGAAT GATCATTTTA GGTTTCGGTT TTCCTCAAAA    2100

TCTAAAGTGT ATGAAGAAAT TAGCATATGA AAATTTAGTA TGTTGATCTT GTCATGATTT    2160

CGCACATTTT TCTAAAAGA ACCTGAAGTC AAATCATAAC GGAACTAGGA GATCGAAGAA    2220

GACCCAAGAA CGGTATAAAC ACATAAATAT GAAGGTTTTG AGAGGGACG AAAGACTACA    2280

TAAGTAGTAT ATTGAGGAGC TATTATTGTG TATGGAGGAA GCCCACTCTG AGAGGAGATG    2340

AGAGACTACA AAAGTAGATC AGCTGTGTCT CGAAGCCTAA AAAATTGGGT TGTGACATTG    2400

AAAGTTCGAT TTTTCCTAAG GTGACATAAG GGGATCTATA ACATCGTACT CTTTGTTTTG    2460

TTCCAATTTC CTACACACAC GACTTGGTCG GCTGTTTGTG GCTTGTCTTT TTACATGGTT    2520

TCAACGTGAC CCTGGGCTTA TAAATTCACT CCCATTTTGT TCTTTCTTTC GTATCTTAAC    2580

AACCCAAAAG CTCTCATTTT TAGGGACACA AAAACAAACA CCTCAACAAC TTTCAA        2636

ATG GGG TTT CAT CAA ATT GAC GAA AGG AAC CAA GCT CTT CTC TCT AAG      2684
Met Gly Phe His Gln Ile Asp Glu Arg Asn Gln Ala Leu Leu Ser Lys
 1               5                  10                  15

ATC GCT ATC GAC GAT GGC CAT GGC GAG AAC TCA GCC TAT TTC GAT GGG      2732
Ile Ala Ile Asp Asp Gly His Gly Glu Asn Ser Ala Tyr Phe Asp Gly
                20                  25                  30

TGG AAA GCT TAT GAT AAC AAT CCG TTT CAC CCC GAG AAT AAT CCT TTG      2780
Trp Lys Ala Tyr Asp Asn Asn Pro Phe His Pro Glu Asn Asn Pro Leu
         35                  40                  45

GGT GTT ATT CAA ATG GGT TTA GCA GAA AAT CAA GTTTCGTATA TAGTGTTTTC    2833
Gly Val Ile Gln Met Gly Leu Ala Glu Asn Gln
     50                  55

ATGTTTTTCT TATATCATTT CACGTTTGAA AATTTCGCTA ACTTTGTTTC TGTGTGAATT    2893

TCGATAG CTT TCT TTT GGT ATG ATT GTT GAC TGG ATT AGA AAA CAC CCC      2942
        Leu Ser Phe Gly Met Ile Val Asp Trp Ile Arg Lys His Pro
            60                  65                  70

GAA GCT TCG ATT TGT ACA CCT GAA GGA CTT GAG AAA TTC AAA AGC ATT      2990
Glu Ala Ser Ile Cys Thr Pro Glu Gly Leu Glu Lys Phe Lys Ser Ile
 75                  80                  85

GCC AAC TTT CAA GAT TAT CAT GGC TTA CAA GAG TTT CGA AAA               3032
Ala Asn Phe Gln Asp Tyr His Gly Leu Gln Glu Phe Arg Lys
 90                  95                 100

GTACTAGATA TGATATTCTA ACTATATCTA AACTCAGAAG CTTAAGTCGA TGGATTATGA    3092

TATATATATA TATATTTTAT TTTTCAG GCG ATG GCG AGT TTC ATG GGG AAG        3143
                              Ala Met Ala Ser Phe Met Gly Lys
                                              105                 110

GTA AGG GGT GGG AGG GTG AAA TTC GAC CCG AGT CGG ATT GTG ATG GGT      3191
Val Arg Gly Gly Arg Val Lys Phe Asp Pro Ser Arg Ile Val Met Gly
            115                 120                 125

GGC GGT GCG ACC GGA GCG AGC GAA ACC GTC ATC TTT TGT TTG GCG GAT      3239
Gly Gly Ala Thr Gly Ala Ser Glu Thr Val Ile Phe Cys Leu Ala Asp
```

```
              130                 135                 140
CCG GGG GAT GCT TTT TTG GTT CCT TCT CCA TAC TAT GCA GCG             3281
Pro Gly Asp Ala Phe Leu Val Pro Ser Pro Tyr Tyr Ala Ala
    145                 150                 155

TAAGTTTTTT TTTTTTTTTT TTCTTTTAAA TCTCTCCTTT TCACTTTACA TATAGAGAGA   3341

GAAACCATTT GACAAATTAT TAACTCTACA AATTCTCTTT GAAAGTCGTA TGTTTTGGGA   3401

GGGTCCAAAC TTCAACCATT CTACCAAGTA AACAATCCAC CTCTTTCATG CCTCATTGCT   3461

GGCATACCTC CTCGTCTTCT CCCTATACTT TCTTTCTTTG TATTCTTCTC CCTAACCGAT   3521

GTGTAATTTC ACAATCTACT CCTTCGAGCT CCAGCATTCT TGTTGGCACA CCACTTTGTG   3581

TCCACTCCCC TTCGAGGCTC AGCCTTCTCG CTAGCTCATT GCTCGGTGTC TGGTTCTAAT   3641

ATCATTTGTA ACAGTCCAAG TCCAATGCTA GTAGATATTG TCCTCGCTTT GGGCTTTCCC   3701

TCTCGGACAT TCCATCAAGT TTTTAGAACA CGTCTGCTAA GAAAAAGTTT TCACACCCTT   3761

ATAAATAATG CTTCGTTCTC CTCCCTAACC GATATGGGAT CTCACTGAAT ATTACCCACT   3821

TGAATAAACT AATAACTTGT GCTCTTCGTT CTTGATATGA AAATCAACCC GATGGAAAGA   3881

ACTGATGTCA AATGATAAGA AAATCACTAT AAGGGAAGTA AGATTCGGAT TACCTTGTTG   3941

ATCGAATATC TCAAGGCAAG AACACTTGTT TGAAATTCGA ATCACTCCAC AACCAAGATT   4001

GATCATGTTG AGCTTGAATG ATTCTGCATG CAATCTAAAC TACATAGAAT TACAAAGAAA   4061

CTTAGTCATT GGCTAAAGAA AGCACAAATG TTTCTTTTAC TATATTTTCC AAGTCGGCTT   4121

ACAAATACAA CATACATGAC TTCGTATAAT CTCAAAATGA AACTATTTAA GGCATTATAA   4181

GAGTGGTAAC ATTCATAATT TATGACCATA ATTAACCATT ATGTAAATAT AATCTAAGGT   4241

AAATAAAAAG CCTTAAAACA TATTAATGAA ATACAATAAC TCCAAATTTT CTAGATTGTA   4301

ATCCACCCAA AATTTATAAA AATGAAACTT CATTCTTCTT CAATGTGACA TGTGGCATGA   4361

ACTGAAATAT CTATTTTCTT CCCATGTTCA TCGAAATATA GTGTATGATT GATGTCTCTT   4421

GGTTCATATC AGTTCTTTAC ATATATTAAT AACCTTTTGG TACGAGGTGA ACAATGTCGT   4481

ATTATTGTAA AAATACTCAA AAGTCTTTGT CCTAACAATC AGTACGTTGT TTTTCAGG    4539

TTT GAT CGA GAC CTA AAA TGG CGA ACA CGA GCA CAA ATA ATT CCT GTT   4587
Phe Asp Arg Asp Leu Lys Trp Arg Thr Arg Ala Gln Ile Ile Pro Val
            160                 165                 170

CAT TGC AAC AGC TCG AAC AAC TTC CAA GTC ACA GAG GCA GCC TTA GAA   4635
His Cys Asn Ser Ser Asn Asn Phe Gln Val Thr Glu Ala Ala Leu Glu
    175                 180                 185

ATA GCC TAT AAA AAG GCT CAA GAG GCC AAC ATG AAA GTG AAG GGT GTT   4683
Ile Ala Tyr Lys Lys Ala Gln Glu Ala Asn Met Lys Val Lys Gly Val
190                 195                 200                 205

ATA ATC ACC AAT CCC TCA AAT CCC TTA GGC ACA ACG TAC GAC CGT GAC   4731
Ile Ile Thr Asn Pro Ser Asn Pro Leu Gly Thr Thr Tyr Asp Arg Asp
                210                 215                 220

ACT CTT AAA ACC CTC GTC ACC TTT GTG AAT CAA CAC GAC ATT CAC TTA   4779
Thr Leu Lys Thr Leu Val Thr Phe Val Asn Gln His Asp Ile His Leu
            225                 230                 235

ATA TGC GAT GAA ATA TAC TCT GCC ACT GTC TTC AAA GCC CCA ACC TTC   4827
Ile Cys Asp Glu Ile Tyr Ser Ala Thr Val Phe Lys Ala Pro Thr Phe
    240                 245                 250

ACC AGC ATC GCT GAG ATT GTT GAA CAA ATG GAG CAT TGC AAG AAG GAG   4875
Thr Ser Ile Ala Glu Ile Val Glu Gln Met Glu His Cys Lys Lys Glu
    255                 260                 265

CTC ATC CAT ATT CTT TAT AGC TTG TCC AAA GAC ATG GGC CTC CCT GGT   4923
Leu Ile His Ile Leu Tyr Ser Leu Ser Lys Asp Met Gly Leu Pro Gly
270                 275                 280                 285
```

```
TTT CGA GTT GGA ATT ATT TAT TCT TAC AAC GAT GTC GTC GTC CGC CGT      4971
Phe Arg Val Gly Ile Ile Tyr Ser Tyr Asn Asp Val Val Val Arg Arg
            290                 295                 300

GCT CGG CAG ATG TCG AGC TTC GGC CTC GTC TCG TCC CAG ACT CAA CAT      5019
Ala Arg Gln Met Ser Ser Phe Gly Leu Val Ser Ser Gln Thr Gln His
            305                 310                 315

TTG CTC GCC GCC ATG CTT TCC GAC GAG GAC TTT GTC GAC AAA TTT CTT      5067
Leu Leu Ala Ala Met Leu Ser Asp Glu Asp Phe Val Asp Lys Phe Leu
            320                 325                 330

GCC GAG AAC TCG AAG CGC CTG GGC GAG AGG CAT GCA AGG TTTGTTAAAC       5116
Ala Glu Asn Ser Lys Arg Leu Gly Glu Arg His Ala Arg
            335                 340                 345

TACACCATTA TTATTTGTGG GATTGAAAAG CATTACAAAA TGCAATTAAT TTAAGAATGT    5176

ATTAATCAAA TTCAGG TTC ACA AAA GAA TTG GAT AAA ATG GGG ATC ACT        5225
               Phe Thr Lys Glu Leu Asp Lys Met Gly Ile Thr
                              350                 355

TGC TTG AAC AGC AAT GCT GGA GTT TTT GTG TGG ATG GAT CTA CGG AGG      5273
Cys Leu Asn Ser Asn Ala Gly Val Phe Val Trp Met Asp Leu Arg Arg
            360                 365                 370

CTA TTA AAA GAC CAA ACC TTC AAA GCT GAA ATG GAG CTT TGG CGT GTG      5321
Leu Leu Lys Asp Gln Thr Phe Lys Ala Glu Met Glu Leu Trp Arg Val
375             380                 385

ATT ATC AAT GAA GTC AAG CTC AAT GTT TCT CCT GGC TCA TCC TTT CAT      5369
Ile Ile Asn Glu Val Lys Leu Asn Val Ser Pro Gly Ser Ser Phe His
390             395                 400                 405

GTC ACT GAG CCA GGT TGG TTT CGA GTT TGT TTC GCA AAC ATG GAC GAC      5417
Val Thr Glu Pro Gly Trp Phe Arg Val Cys Phe Ala Asn Met Asp Asp
            410                 415                 420

AAC ACC GTT GAC GTT GCT CTC AAT AGA ATC CAT AGC TTT GTC GAA AAC      5465
Asn Thr Val Asp Val Ala Leu Asn Arg Ile His Ser Phe Val Glu Asn
            425                 430                 435

ATC GAC AAG AAG GAA GAC AAT ACC GTT GCA ATG CCA TCG AAA ACG AGG      5513
Ile Asp Lys Lys Glu Asp Asn Thr Val Ala Met Pro Ser Lys Thr Arg
            440                 445                 450

CAT CGA GAT AAT AAG TTA CGA TTG AGC TTC TCC TTC TCC GGG AGA AGA      5561
His Arg Asp Asn Lys Leu Arg Leu Ser Phe Ser Phe Ser Gly Arg Arg
            455                 460                 465

TAC GAC AAG GGC AAC GTT CTT AAC TCA CCG CAC ACG ATG TCG CCT CAC      5609
Tyr Asp Lys Gly Asn Val Leu Asn Ser Pro His Thr Met Ser Pro His
470             475                 480                 485

TCG CCA TTG GTA AGA GCC AGA ACT TAT TAAAGATGAG TTTGAGAAGA            5656
Ser Pro Leu Val Arg Ala Arg Thr Tyr
            490

TATTATCATA AGTTTTTTTT AGCTCATTAA TGAATGGATG GATATTTAAA ACTATGAAGT    5716

GTAGCACTCA TGCTCCGAAG GAATTAATTT CTTGATTGCT GAATTTTAAG ACGATATAAA    5776

AGAGAAAAAA TGTTTAGAAA AATCTAAAAA ATGGGAGAAA AAAAGAAAA CAATTAAAAT     5836

TTAAAAATCA GTCAAAATCA TTAAAGTAGT ACATATAGCT CATACTAGAA GGTGAGACAA    5896

GACTCTGAAA TGATTTTTAT GATACGTCTT TAACTACGAT TGCATTTCTT GACTGGGGTT    5956

ACTGCATTTC TTGACTGGGG TTACTTACTA AGTATTTCTA GAAATACTCA AGTCACATGC    6016

TACTCTTATT TTCAGGTAAA GGCAATGTAC CTCTTCACGG ACGATGACGT CGCGGTGACG    6076

CCATGAGATT GAAGCTAGGG TAGAAGTATT CATGTTATTT TTGTAGCCCT TAGGTTAGAT    6136

CAAAATATCG TCTTATTTTA TTTTTATTTT ATCAAAATTT TACGTGATTT GTTTTCCATT    6196

TTAATTGTTC AATAATTTTA TTATGAACAT GTAAGTTCAT GGCACTTTTT TAAAATATTT    6256
```

```
TAAAAGTTTT TTTTTTTCGA TTCTTAATTA ATTTATGCAT GTAGTAGCGA GTTTATCATA      6316

GTCAAGGAGG ATGTTTTGTG AAATGTTAAG CTGAATGGTT ATGTGTAAAA CGGAGAGTCT      6376

ACTAATGCTA TTAAGATTTT TATGTAAACA AGTCTTCCAC TTGATTTCTG TCTTGATTTG      6436

CTACATCTCG ATTTCTTCCG TCAAGAATTT CTCTCTAACG AAATGATAAT GCACCTCCAC      6496

ATGTTTTATT CTAGCATGAA ACATCGAATT TTCTGTTAGG CAAATCGCAG ATTGGTTGTT      6556

GTAATGAAGT GGTATTGGAT AGTCAATTTT CTTGTGCCGA TCTTTCATCA AGAGTTTCAG      6616

TCATGTACTT TCCTAAACTG CTCCAACCGC TACTCTGTAC TCTACTTCTC TAGTTGACAA      6676

TGATACTGTT GATTTTCTTT TGCTACACTG AGAAGTTGTT CTCGAACCGA GCTTGAACAC      6736

ATACCTGGTG CTTGATCTTC GGGTATTGTG ATATTCTACA TAGTCAGCAT CACGGTATCT      6796

GGATAACTTG TAGTCTTCGC TTCTTTTATA CAAACGATCA TAATGATTGT GCCTTTGACA      6856

TATCTCAAGG TCCGTCAAGT CGCATCCAAA TGAGGTTTCT TTGCACTTTG TATGTACTGA      6916

CTAATGACTC CAACTCCGTT CTCAAATTTC TTCGGTTGGT TCATGTAGAT CTCTCTATTT      6976

AACTCTCCGT GCAAGAAAGC ATTCTTCATA TCCATCTGTC GTAATTTCCA ATCTTTATTT      7036

ACCACAAGTG CTGGAGGAAC CTATATGATG GTGATCTTTG CCACTGAACT AAATGTTTCA      7096

TCATAGTCCA TATTGTTGAG AGAACCCTGG AGCTACAGTC TGAGTTGTGT ATCTCACTAT      7156

TCATCCATTC GGGATACACT TTATTTTGTA AATCCACTTG CAAAAGATGG ATTTGACATC      7216

TTCTGGTCTT TGTACTAATT CCCAGGTTTG ATTTATCTCG AAGGGTATAA TTTCTTCCTC      7276

CATTGTCTGC TGCCAAGCCG TATTGCGTGA TGCTTCTTTA TACGTCTCTA GCTCTTTACT      7336

TTGTCTTCTA AAATAGTTAT ATTGAACATA CTTTGGATTT GGCTTATGGA TTCTTTCTAA      7396

CCATCTAAGT CGTTGAGGTG TCATTTCCTT TTCACTAGGT TCGCTTGATT GAGTCACTCC      7456

TTGCTCACCA ACATTAGTGT CACTTGGATA TTTAGACACA TCAGCATTTA AGAAAATGTG      7516

TACAGTTTTC TCCCCCGTAT TCTGTGGAAG AATTTCTTCA GTTTGCTCCC CCGTCTTCTG      7576

TGGAAGAATT C                                                         7587
```

(2) INFORMATION FOR SEQ ID NO:23:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO:23:

```
Met Gly Phe His Gln Ile Asp Glu Arg Asn Gln Ala Leu Leu Ser Lys
 1               5                  10                  15

Ile Ala Ile Asp Asp Gly His Gly Glu Asn Ser Ala Tyr Phe Asp Gly
                20                  25                  30

Trp Lys Ala Tyr Asp Asn Asn Pro Phe His Pro Glu Asn Asn Pro Leu
            35                  40                  45

Gly Val Ile Gln Met Gly Leu Ala Glu Asn Gln Leu Ser Phe Gly Met
        50                  55                  60

Ile Val Asp Trp Ile Arg Lys His Pro Glu Ala Ser Ile Cys Thr Pro
65                  70                  75                  80

Glu Gly Leu Glu Lys Phe Lys Ser Ile Ala Asn Phe Gln Asp Tyr His
                85                  90                  95

Gly Leu Gln Glu Phe Arg Lys Ala Met Ala Ser Phe Met Gly Lys Val
               100                 105                 110
```

```
Arg Gly Gly Arg Val Lys Phe Asp Pro Ser Arg Ile Val Met Gly Gly
            115                 120                 125

Gly Ala Thr Gly Ala Ser Glu Thr Val Ile Phe Cys Leu Ala Asp Pro
        130                 135                 140

Gly Asp Ala Phe Leu Val Pro Ser Pro Tyr Tyr Ala Ala Phe Asp Arg
145                 150                 155                 160

Asp Leu Lys Trp Arg Thr Arg Ala Gln Ile Ile Pro Val His Cys Asn
                165                 170                 175

Ser Ser Asn Asn Phe Gln Val Thr Glu Ala Ala Leu Glu Ile Ala Tyr
            180                 185                 190

Lys Lys Ala Gln Glu Ala Asn Met Lys Val Lys Gly Val Ile Ile Thr
        195                 200                 205

Asn Pro Ser Asn Pro Leu Gly Thr Thr Tyr Asp Arg Asp Thr Leu Lys
    210                 215                 220

Thr Leu Val Thr Phe Val Asn Gln His Asp Ile His Leu Ile Cys Asp
225                 230                 235                 240

Glu Ile Tyr Ser Ala Thr Val Phe Lys Ala Pro Thr Phe Thr Ser Ile
                245                 250                 255

Ala Glu Ile Val Glu Gln Met Glu His Cys Lys Lys Glu Leu Ile His
            260                 265                 270

Ile Leu Tyr Ser Leu Ser Lys Asp Met Gly Leu Pro Gly Phe Arg Val
        275                 280                 285

Gly Ile Ile Tyr Ser Tyr Asn Asp Val Val Arg Arg Ala Arg Gln
    290                 295                 300

Met Ser Ser Phe Gly Leu Val Ser Ser Gln Thr Gln His Leu Leu Ala
305                 310                 315                 320

Ala Met Leu Ser Asp Glu Asp Phe Val Asp Lys Phe Leu Ala Glu Asn
                325                 330                 335

Ser Lys Arg Leu Gly Glu Arg His Ala Arg Phe Thr Lys Glu Leu Asp
            340                 345                 350

Lys Met Gly Ile Thr Cys Leu Asn Ser Asn Ala Gly Val Phe Val Trp
        355                 360                 365

Met Asp Leu Arg Arg Leu Leu Lys Asp Gln Thr Phe Lys Ala Glu Met
370                 375                 380

Glu Leu Trp Arg Val Ile Ile Asn Glu Val Lys Leu Asn Val Ser Pro
385                 390                 395                 400

Gly Ser Ser Phe His Val Thr Glu Pro Gly Trp Phe Arg Val Cys Phe
                405                 410                 415

Ala Asn Met Asp Asp Asn Thr Val Asp Val Ala Leu Asn Arg Ile His
            420                 425                 430

Ser Phe Val Glu Asn Ile Asp Lys Lys Glu Asp Asn Thr Val Ala Met
        435                 440                 445

Pro Ser Lys Thr Arg His Arg Asp Asn Lys Leu Arg Leu Ser Phe Ser
    450                 455                 460

Phe Ser Gly Arg Arg Tyr Asp Lys Gly Asn Val Leu Asn Ser Pro His
465                 470                 475                 480

Thr Met Ser Pro His Ser Pro Leu Val Arg Ala Arg Thr Tyr
                485                 490
```

(2) INFORMATION FOR SEQ ID NO:24:

(i) SEQUENCE CHARACTERISTICS:
        (A) LENGTH: 2230 base pairs
        (B) TYPE: nucleic acid
        (C) STRANDEDNESS: single -continued

```
        (D) TOPOLOGY: linear (ix) FEATURE:
        (A) NAME/KEY: CDS
        (B) LOCATION: 91..1545

(xi) SEQUENCE DESCRIPTION: SEQ ID NO:24:

TGTAGTTGTG TACATTTTAT TAATCTTCAT CTTCTTAATT CTCTTCAGTT TTTAATTTCT      60

TCACTTCTAA ACTCATTTAG TAAAAAAAAA ATG GGA TTT GAG ATT GCA AAG ACC     114
                                Met Gly Phe Glu Ile Ala Lys Thr
                                  1               5

AAC TCA ATC TTA TCA AAA TTG GCT ACT AAT GAA GAG CAT GGC GAA AAC      162
Asn Ser Ile Leu Ser Lys Leu Ala Thr Asn Glu Glu His Gly Glu Asn
 10              15                  20

TCG CCA TAT TTT GAT GGG TGG AAA GCA TAC GAT AGT GAT CCT TTC CAC      210
Ser Pro Tyr Phe Asp Gly Trp Lys Ala Tyr Asp Ser Asp Pro Phe His
 25              30                  35                  40

CCT CTA AAA AAC CCC AAC GGA GTT ATC CAA ATG GGT CTT GCT GAA AAT      258
Pro Leu Lys Asn Pro Asn Gly Val Ile Gln Met Gly Leu Ala Glu Asn
                 45                  50                  55

CAG CTT TGT TTA GAC TTG ATA GAA GAT TGG ATT AAG AGA AAC CCA AAA      306
Gln Leu Cys Leu Asp Leu Ile Glu Asp Trp Ile Lys Arg Asn Pro Lys
             60                  65                  70

GGT TCA ATT TGT TCT GAA GGA ATC AAA TCA TTC AAG GCC ATT GCC AAC      354
Gly Ser Ile Cys Ser Glu Gly Ile Lys Ser Phe Lys Ala Ile Ala Asn
         75                  80                  85

TTT CAA GAT TAT CAT GGC TTG CCT GAA TTC AGA AAA GCG ATT GCG AAA      402
Phe Gln Asp Tyr His Gly Leu Pro Glu Phe Arg Lys Ala Ile Ala Lys
     90                  95                 100

TTT ATG GAG AAA ACA AGA GGA GGA AGA GTT AGA TTT GAT CCA GAA AGA      450
Phe Met Glu Lys Thr Arg Gly Gly Arg Val Arg Phe Asp Pro Glu Arg
105                 110                 115                 120

GTT GTT ATG GTT GGT GGT GCC ACT GGA GCT AAT GAG ACA ATT ATA TTT      498
Val Val Met Val Gly Gly Ala Thr Gly Ala Asn Glu Thr Ile Ile Phe
                125                 130                 135

TGT TTG GCT GAT CCT GGC GAT GCA TTT TTA GTA CCT TCA CCA TAC TAC      546
Cys Leu Ala Asp Pro Gly Asp Ala Phe Leu Val Pro Ser Pro Tyr Tyr
            140                 145                 150

CCA GCA TTT AAC AGA GAT TTA AGA TGG AGA ACT GGA GTA CAA CTT ATT      594
Pro Ala Phe Asn Arg Asp Leu Arg Trp Arg Thr Gly Val Gln Leu Ile
        155                 160                 165

CCA ATT CAC TGT GAG AGC TCC AAT AAT TTC AAA ATT ACT TCA AAA GCA      642
Pro Ile His Cys Glu Ser Ser Asn Asn Phe Lys Ile Thr Ser Lys Ala
    170                 175                 180

GTA AAA GAA GCA TAT GAA AAT GCA CAA AAA TCA AAC ATC AAA GTA AAA      690
Val Lys Glu Ala Tyr Glu Asn Ala Gln Lys Ser Asn Ile Lys Val Lys
185                 190                 195                 200

GGT TTG ATT TTG ACC AAT CCA TCA AAT CCA TTG GGC ACC ACT TTG GAC      738
Gly Leu Ile Leu Thr Asn Pro Ser Asn Pro Leu Gly Thr Thr Leu Asp
                205                 210                 215

AAA GAC ACA CTG AAA AGT GTC TTG AGT TTC ACC AAC CAA CAC AAC ATC      786
Lys Asp Thr Leu Lys Ser Val Leu Ser Phe Thr Asn Gln His Asn Ile
            220                 225                 230

CAC CTT GTT TGT GAC GAA ATC TAC GCA GCC ACT GTC TTT GAC ACG CCT      834
His Leu Val Cys Asp Glu Ile Tyr Ala Ala Thr Val Phe Asp Thr Pro
        235                 240                 245

CAA TTC GTC AGT ATA GCT GAA ATC CTC GAT GAA CAG GAA ATG ACT TAC      882
Gln Phe Val Ser Ile Ala Glu Ile Leu Asp Glu Gln Glu Met Thr Tyr
    250                 255                 260

TGC AAC AAA GAT TTA GTT CAC ATC GTC TAC AGT CTT TCA AAA GAC ATG      930
```

```
Cys Asn Lys Asp Leu Val His Ile Val Tyr Ser Leu Ser Lys Asp Met
265                 270                 275                 280

GGG TTA CCA GGA TTT AGA GTC GGA ATC ATA TAT TCT TTT AAC GAC GAT        978
Gly Leu Pro Gly Phe Arg Val Gly Ile Ile Tyr Ser Phe Asn Asp Asp
                285                 290                 295

GTC GTT AAT TGT GCT AGA AAA ATG TCG AGT TTC GGT TTA GTA TCT ACA       1026
Val Val Asn Cys Ala Arg Lys Met Ser Ser Phe Gly Leu Val Ser Thr
            300                 305                 310

CAA ACG CAA TAT TTT TTA GCG GCA ATG CTA TCG GAC GAA AAA TTC GTC       1074
Gln Thr Gln Tyr Phe Leu Ala Ala Met Leu Ser Asp Glu Lys Phe Val
        315                 320                 325

GAT AAT TTT CTA AGA GAA AGC GCG ATG AGG TTA GGT AAA AGG CAC AAA       1122
Asp Asn Phe Leu Arg Glu Ser Ala Met Arg Leu Gly Lys Arg His Lys
    330                 335                 340

CAT TTT ACT AAT GGA CTT GAA GTA GTG GGA ATT AAA TGC TTG AAA AAT       1170
His Phe Thr Asn Gly Leu Glu Val Val Gly Ile Lys Cys Leu Lys Asn
345                 350                 355                 360

AAT GCG GGG CTT TTT TGT TGG ATG GAT TTG CGT CCA CTT TTA AGG GAA       1218
Asn Ala Gly Leu Phe Cys Trp Met Asp Leu Arg Pro Leu Leu Arg Glu
                365                 370                 375

TCG ACT TTC GAT AGC GAA ATG TCG TTA TGG AGA GTT ATT ATA AAC GAT       1266
Ser Thr Phe Asp Ser Glu Met Ser Leu Trp Arg Val Ile Ile Asn Asp
            380                 385                 390

GTT AAG CTT AAC GTC TCG CCT GGA TCT TCG TTT GAA TGT CAA GAG CCA       1314
Val Lys Leu Asn Val Ser Pro Gly Ser Ser Phe Glu Cys Gln Glu Pro
        395                 400                 405

GGG TGG TTC CGA GTT TGT TTT GCA AAT ATG GAT GAT GGA ACG GTT GAT       1362
Gly Trp Phe Arg Val Cys Phe Ala Asn Met Asp Asp Gly Thr Val Asp
    410                 415                 420

ATT GCG CTC GCG AGG ATT CGG AGG TTC GTA GGT GTT GAG AAA AGT GGA       1410
Ile Ala Leu Ala Arg Ile Arg Arg Phe Val Gly Val Glu Lys Ser Gly
425                 430                 435                 440

GAT AAA TCG AGT TCG ATG GAA AAG AAG CAA CAA TGG AAG AAG AAT AAT       1458
Asp Lys Ser Ser Ser Met Glu Lys Lys Gln Gln Trp Lys Lys Asn Asn
                445                 450                 455

TTG AGA CTT AGT TTT TCG AAA AGA ATG TAT GAT GAA AGT GTT TTG TCA       1506
Leu Arg Leu Ser Phe Ser Lys Arg Met Tyr Asp Glu Ser Val Leu Ser
            460                 465                 470

CCA CTT TCG TCA CCT ATT CCT CCC TCA CCA TTA GTT CGT TAAGACTTAA        1555
Pro Leu Ser Ser Pro Ile Pro Pro Ser Pro Leu Val Arg
        475                 480                 485

TTAAAAGGGA AGAATTTAAT TTATGTTTTT TTATATTTTG AAAAAAATTT GTAAGAATAA     1615

GATTATAATA GGAAAAGAAA ATAAGTATGT AGGATGAGGA GTATTTTCAG AAATAGTTGT     1675

TAGCGTATGT ATTGACAACT GGTCTATGTA CTTAGCATC ATAATTTGTC TTAGCTAATT      1735

AACGAATGCA AAAGTGAAGT TATGTTATGA CTCTTAGAAT ATGTACTTAG ACATCATAAT     1795

TTGTCTTAGC TAATTAATGA ATGCAAAAGT GAAGTTATGT TATGACTCTT AGAATCTTTT    1855

GATTTATTGG ACTTTCTCGA ATGTACTTAG ACATCATAAT TTGTCTTAGC TAATTAATGA    1915

ATGCAAAAGT GAAGTTATGT TATGAAAAAA AAAAAAAAA AAAATGTACT TAGACATCAT     1975

AATTTGTCTT AGCTAATTAA TGAATGCAAA AGTGAAGTTA TGTTAAAAAA AAAAAAAAA     2035

AAAAATGTAC TTAGACATCA TAATTTGTCT TAGCTAATTA ATGAATGCAA AGTGAAGTT     2095

ATGTTAAAAA AAAAAAAAAA AAAATGTAC TTAGACATCA TAATTTGTCT TAGCTAATTA     2155

AAAAAAAAAA AAAAAAAAAA AAAAAAAAAA AAAAAAAAA AAAAAAAAAA AAAAAATTA     2215

TATTGTTAAA AAAAA                                                    2230
```

(2) INFORMATION FOR SEQ ID NO:25:

(i) SEQUENCE CHARACTERISTICS:
       (A) LENGTH: 485 amino acids
       (B) TYPE: amino acid
       (D) TOPOLOGY: linear (ii) MOLECULE TYPE: protein (xi) SEQUENCE DESCRIPTION: SEQ ID NO:25:

```
Met Gly Phe Glu Ile Ala Lys Thr Asn Ser Ile Leu Ser Lys Leu Ala
 1               5                  10                  15

Thr Asn Glu Glu His Gly Glu Asn Ser Pro Tyr Phe Asp Gly Trp Lys
             20                  25                  30

Ala Tyr Asp Ser Asp Pro Phe His Pro Leu Lys Asn Pro Asn Gly Val
         35                  40                  45

Ile Gln Met Gly Leu Ala Glu Asn Gln Leu Cys Leu Asp Leu Ile Glu
     50                  55                  60

Asp Trp Ile Lys Arg Asn Pro Lys Gly Ser Ile Cys Ser Glu Gly Ile
 65                  70                  75                  80

Lys Ser Phe Lys Ala Ile Ala Asn Phe Gln Asp Tyr His Gly Leu Pro
                 85                  90                  95

Glu Phe Arg Lys Ala Ile Ala Lys Phe Met Glu Lys Thr Arg Gly Gly
            100                 105                 110

Arg Val Arg Phe Asp Pro Glu Arg Val Val Met Val Gly Gly Ala Thr
        115                 120                 125

Gly Ala Asn Glu Thr Ile Ile Phe Cys Leu Ala Asp Pro Gly Asp Ala
    130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
```

```
                355                 360                 365
Asp Leu Arg Pro Leu Arg Glu Ser Thr Phe Asp Ser Glu Met Ser
            370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
                420                 425                 430

Phe Val Gly Val Glu Lys Ser Gly Asp Lys Ser Ser Met Glu Lys
            435                 440                 445

Lys Gln Gln Trp Lys Lys Asn Asn Leu Arg Leu Ser Phe Ser Lys Arg
450                 455                 460

Met Tyr Asp Glu Ser Val Leu Ser Pro Leu Ser Ser Pro Ile Pro Pro
465                 470                 475                 480

Ser Pro Leu Val Arg
            485

(2) INFORMATION FOR SEQ ID NO:26:

(i) SEQUENCE CHARACTERISTICS:
        (A) LENGTH: 7244 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(3056..3226, 3325..3453, 3539..3700,
            4582..5574)

(xi) SEQUENCE DESCRIPTION: SEQ ID NO:26:

GGATCCTCAT TACTTGTCTA TGGCTAAAGT GTTAAAGAAT TATTCACAAT ATCTAACACA      60

TTTAATGACT ATTCAACTAA TAGTGACGAT CTTTTAAAAT AAAATGAAGA ACTTAAAATT     120

TTGACCAACT TCCTAACGAT ATTAATGAGG GATACAGATT TGATTTACGC AAAAAAAAAA     180

GAAAAAAGA AATGATATTA CTCAATTATA AATTTGATTA GAGAATAGCT AGGCCTATAA      240

TTGTTTTACA TTATCTATTC CTAAGTTATG ATATTATCCT TCAATTTACC TGATAGCGTA     300

AAAATTACAA TAATTTGTAC ACTAATGATG CACAAAACTT AAATTCATTA TATATACACA     360

TACAAGGCCG AGGGCTTAAT AGAATCGATG ACCTGAAATC ATATTTCTAT TGTTTAGCAA     420

TAGAAATTAG TTATGGCTTC AAATTTAGCG ATGAATTCCA TGGGTGTTTG CATTGACTTA     480

AAAGATGATC AAATCTACTT TGAAGTCCGT TTTTGAATTT TGAAAGTGTT TGATAAAATAT    540

AAAAATAACT AAAAATAAGT TAGGAAGTGT TTGACAAAGT TAAATCTTAA ATAATTTAT      600

CAACCAAAAG TAGGTCTCCC CTATTCTTTT TTTTTTTGGA CTTAAAAGTC GTTTAAACGT     660

AATTTGACTT ATAAATTTTT TAAAGTTAAT TTAAACCGGC TTTGTAAAAG AAATTAACAA     720

TTCATTTGGA ATGTTAATTA TTAAAAGATC CAGATATGTA CAAAATAAAA ATAACCTACC     780

TCCTATAGTA AAGATTTTCA AACAATATTA AGTTAAACAA AGTCAAAAAG TTGGTATATT     840

GAATTTTACT AGTCTTGTAT AAACCAATAC AATTAGCTTC GAAAAGTCAT TGATATATTT     900

TTCTATGTGC TGCTTGTTGG GAAACTTCCT GTAACACAAA GAATGAATGA ATTCTCCCAC     960

ATTTTTATTT TGTAGATTTA ATTCCCTATT TGATATCAAA AATATTCTGG AGAAGGAAGG    1020

AATACGAGCC TAACCAAGAC TAGGCCAATT AAGCAGCCCA TGATAAGCCT CCATTCAAAT    1080

GAAATATCAA AATCACTGTA TTATTATAAG ATACTTTGAG AATATATATT GTTTGGTCAA    1140
```

-continued

```
ATAGTTTATT AACATATATA TTATATATAA GTATGTGAAA TGATGAAGCT AGAGTTTTAT    1200

ATGAACATAT AATTTAGATT TTAAGTTGTA TATTTTGCTC ATAAATATAA AATTCTATGA    1260

ATTGTAAAAT TATCAATATT TACTTAATTC TTTACGCAAT CTTACTAAAT ATATAAAAGT    1320

TAATAACTAC AAAAGTATAA TCATACGATC ACAAACGAGC TATTCTAAAA AAAGTATCAC    1380

ATATTTAATA TAATCCTCCC ACATAGTACA AACAATCTTC TCATGTTTTG TAATAATAAA    1440

TGATGTAAGG GTTTAAAGGT GGTGTGAATA ATAATTGCAA CTAAAAAATT TATTTACATC    1500

TAAAATAAAT AATTAATACA TATAAAATCG TATGATCAAA AATTTAAAAT TTAAATCATG    1560

ATATGTAATT AATATGTCCA GACACCTGCT TAATAAAAAC TATACACTAT TAATGCAGTA    1620

TGCACTTTAT ACATATTTTG TAAATTAGAT AATTAAATGG CCGGCTAGAG TAATGCAATA    1680

CGATAGAAAA GCTCGATCAA AATTAATCAC ACTCAATGTG CCTAGTAAGA TCTTCAAATC    1740

AAAATCAATT ATGATTATCA TCTGCGGTCC ATTGTTCTCG TCCCTTCCCA GGAAAGTAAT    1800

TATCCCTATT ATATTTTTAT TTATTTATAT AAACTACTTG AAAAAGGTAA AAAGAATAAA    1860

TAAATAAATT ACCAGTAGTA CCATTGTATT CTCAACTTTT TTCTTTCTCA CGTGTAGCTT    1920

CTAGCTTGAA CATGAAATTT CATATAACTA TTTAGACGAA GGCAATTACG ACTAAGGGTA    1980

TGTTCGATAA GAAAAGAAAA TATTTTCTTA AAAAATAAAT AAATTTTTAA TTTATTTTTC    2040

ATATTTGATT AATAAGCAGA AATATTTTT GAGGAAGTAT CTTTTTTTAT TTTTGAGAAA     2100

ATACTTTCTA TGAAAATAAT TATTGATGTG AAAATCAATC TCGATAATTG TTGCAGGAAA    2160

CGACTCTGAC AATCGAATTA GGATAAAACC TCGATGACCT TTAAAATCGA CCCTAAAATC    2220

TGATCCAAAA CTCGATCCAG ACTTCCGATC CAAAACTTGA TTCAAGTAAA TATTTTTAAA    2280

AATAAATTCT TTTTGACAGG GTGGCGTAAA AATAATTTTA TTTTAAAATA TGATATAGTT    2340

TTCTAAAATA TATTTTTTTG TTTGGTTGTT GGGGGTTGGT TCGAGGCTAG GGGTAAAAAT    2400

AATTAAAACA TAAGAAATTT TAAAAGTTTT AATTGCATTT TTTTTGTGTT GGGGAGGGGC    2460

GGATTTGGG TTGGATAAGA AAAAATATTT AAAGATAAAA TAGAATTTTG GAAAATATTT     2520

TTCTTAATTT TTGAAGGAAA ATCATTTTTC TTAAATTTGA GAAAATGAA TTATTCTTAA     2580

AAAAAATTTC CAAAAACATT TAAGCTACCA AATATGAAAA AATAAAAAAT ATTTTTTTTC    2640

CTACCAAATG CACCCTAAAT TAGTCAAATA TCCAACATTT AAAAGAGCTA TGAAAAAAAA    2700

AAAGAAGTAA GAATCGTAGA TCTTCTTTTA ATGCGTACTT TTATTTTCCA AGATTTGAAC    2760

AATAAAATAG ACTTTTCTAT TTTTATTTTC TGATGTAATT CTTATATACG TTAGTCGACA    2820

TGTTCTCATT ACATACTTCA GTCTTTCCCC TTATATATAT CCCTCACATT CCTTAATTCT    2880

CTTACACCAT AACACAACTA CAACAAACAC ATAATACTTT TAATACAATT AGTTATTTAT    2940

TAGAAGTATT TAAAGTAAAG CACTTGTGAG TTGTGTACAT TTTATTAATC TTCATCTTCT    3000

TAATTCTCTT CAGTTTTTAA TTTCTTCACT TCTAAACTCA TTTAGTAAAA AAAAA ATG     3058
                                                                   Met
                                                                    1

GGA TTT GAG ATT GCA AAG ACC AAC TCA ATC TTA TCA AAA TTG GCT ACT     3106
Gly Phe Glu Ile Ala Lys Thr Asn Ser Ile Leu Ser Lys Leu Ala Thr
              5                  10                  15

AAT GAA GAG CAT GGC GAA AAC TCG CCA TAT TTT GAT GGG TGG AAA GCA     3154
Asn Glu Glu His Gly Glu Asn Ser Pro Tyr Phe Asp Gly Trp Lys Ala
         20                  25                  30

TAC GAT AGT GAT CCT TTC CAC CCT CTA AAA AAC CCC AAC GGA GTT ATC     3202
Tyr Asp Ser Asp Pro Phe His Pro Leu Lys Asn Pro Asn Gly Val Ile
     35                  40                  45
```

-continued

```
CAA ATG GGT CTT GCT GAA AAT CAG GTAATTAATT ATCCTTTATT TATATATTTT    3256
Gln Met Gly Leu Ala Glu Asn Gln
 50                      55

GCAGTTTGAC CAAACAGACT ATTATAATTT TTTTCTGAAA CCTCGATGGT GTTAAATTTC    3316

TTTTGTAG CTT TGT TTA GAC TTG ATA GAA GAT TGG ATT AAG AGA AAC CCA    3366
         Leu Cys Leu Asp Leu Ile Glu Asp Trp Ile Lys Arg Asn Pro
              60                  65                  70

AAA GGT TCA ATT TGT TCT GAA GGA ATC AAA TCA TTC AAG GCC ATT GCC    3414
Lys Gly Ser Ile Cys Ser Glu Gly Ile Lys Ser Phe Lys Ala Ile Ala
             75                  80                  85

AAC TTT CAA GAT TAT CAT GGC TTG CCT GAA TTC AGA AAA GTACATATCG    3463
Asn Phe Gln Asp Tyr His Gly Leu Pro Glu Phe Arg Lys
         90                  95                 100

TACTATAGTC AGTTAAATTA TATTGATAGT ATAAAAATTC GTTAATATAT TTAACTAACG    3523

AGTTTATTTA ATCAG GCG ATT GCG AAA TTT ATG GAG AAA ACA AGA GGA GGA    3574
                Ala Ile Ala Lys Phe Met Glu Lys Thr Arg Gly Gly
                                   105                 110

AGA GTT AGA TTT GAT CCA GAA AGA GTT GTT ATG GCT GGT GGT GCC ACT    3622
Arg Val Arg Phe Asp Pro Glu Arg Val Val Met Ala Gly Gly Ala Thr
            115                 120                 125

GGA GCT AAT GAG ACA ATT ATA TTT TGT TTG GCT GAT CCT GGC GAT GCA    3670
Gly Ala Asn Glu Thr Ile Ile Phe Cys Leu Ala Asp Pro Gly Asp Ala
        130                 135                 140

TTT TTA GTA CCT TCA CCA TAC TAC CCA GCG TAAGTATATT TAATTATATA    3720
Phe Leu Val Pro Ser Pro Tyr Tyr Pro Ala
145                 150

TGTGTAAAAA AAATTAAAAT CATCAAATCA TTTTTTTTAT TTGTATTACC AAATAAATTG    3780

TCTAATTTTC AAGATTGTAA CACATTCATC AAAGTACCTA ATAATATAAA CGATTCAGTA    3840

TATTAACGAT GTATATAATT TAATTCCTTT GGCGGATTTG TCTTTTTATG TTGGGCCATC    3900

AGAAGAACAT TCTGGTGTAT AATTAATTA ATTAATTAAT AATAGATGTG TTGTCATTCT    3960

TTTTTAAGAC AGCGAGAGTT TAATTAGTCT TAATTACTGG ATTATCACGC AAGCTCTTTC    4020

TTGAATTTTA TTATTCTTAT ATTAAACACA TGATAGCATA ATATCTTTCT TTTGTGGAAT    4080

CCAGCTTGTT CGTGAAGCTT TGTATTCACA CTTATAAAAC AACAAAAAAT AAAATCTGGT    4140

GGTAATTGAT TAAAGAGAGA AATATAAAAA AATAATAGTC AAATAGACTA ATAAGGAAAG    4200

AAATAAAAAA TACACAAAAT ACTAAAAAAA AAGAATTAAG GTATAGTGGT CTATTATTGA    4260

GAACTTTTTT GAAGAATTGA ACCCCACTTT AATTTCTTGC TTGACCCGTG ACCATTGCTT    4320

ATCGAGGTAA AATAAAATTT CAAACATTGA CTATGACTTG TTAGAGAGTA ATTACCACAA    4380

GTCAAAATTT TGTTACTCTG TCTCGTTATT TCATTAGGAT CGATAAGATA ACATCTAACA    4440

TATATATCTT TTTTATTAGT ACTTGTTTAT TTTTAGTAAA AGCACGTTAT ACATTTTACA    4500

ATAGTCAATT GTTGCATATA TTAGTATATA TATTTTGCTA AGTCCTAACT AACAATATTT    4560

TTGGCAATTG ACTAATGCAG A TTT AAC AGA GAT TTA AGA TGG AGA ACT GGA    4611
               Phe Asn Arg Asp Leu Arg Trp Arg Thr Gly
                       155                 160

GTA CAA CTT ATT CCA ATT CAC TGT GAG AGC TCC AAT AAT TTC AAA ATT    4659
Val Gln Leu Ile Pro Ile His Cys Glu Ser Ser Asn Asn Phe Lys Ile
165                 170                 175                 180

ACT TCA AAA GCA GTA AAA GAA GCA TAT GAA AAT GCA CAA AAA TCA AAC    4707
Thr Ser Lys Ala Val Lys Glu Ala Tyr Glu Asn Ala Gln Lys Ser Asn
            185                 190                 195

ATC AAA GTA AAA GGT TTG ATT TTG ACC AAT CCA TCA AAT CCA TTG GGC    4755
Ile Lys Val Lys Gly Leu Ile Leu Thr Asn Pro Ser Asn Pro Leu Gly
        200                 205                 210
```

```
ACC ACT TTG GAC AAA GAC ACA CTG AAA AGT GTC TTG AGT TTC ACC AAC       4803
Thr Thr Leu Asp Lys Asp Thr Leu Lys Ser Val Leu Ser Phe Thr Asn
            215                 220                 225

CAA CAC AAC ATC CAC CTT GTT TGT GAC GAA ATC TAC GCA GCC ACT GTC       4851
Gln His Asn Ile His Leu Val Cys Asp Glu Ile Tyr Ala Ala Thr Val
        230                 235                 240

TTT GAC ACG CCT CAA TTC GTC AGT ATA GCT GAA ATC CTC GAT GAA CAG       4899
Phe Asp Thr Pro Gln Phe Val Ser Ile Ala Glu Ile Leu Asp Glu Gln
245                 250                 255                 260

GAA ATG ACT TAC TGC AAC AAA GAT TTA GTT CAC ATC GTC TAC AGT CTT       4947
Glu Met Thr Tyr Cys Asn Lys Asp Leu Val His Ile Val Tyr Ser Leu
                265                 270                 275

TCA AAA GAC ATG GGG TTA CCA GGA TTT AGA GTC GGA ATC ATA TAT TCT       4995
Ser Lys Asp Met Gly Leu Pro Gly Phe Arg Val Gly Ile Ile Tyr Ser
            280                 285                 290

TTT AAC GAC GAT GTC GTT AAT TGT GCT AGA AAA ATG TCG AGT TTC GGT       5043
Phe Asn Asp Asp Val Val Asn Cys Ala Arg Lys Met Ser Ser Phe Gly
        295                 300                 305

TTA GTA TCT ACA CAA ACG CAA TAT TTT TTA GCG GCA ATG CTA TCG GAC       5091
Leu Val Ser Thr Gln Thr Gln Tyr Phe Leu Ala Ala Met Leu Ser Asp
        310                 315                 320

GAA AAA TTC GTC GAT AAT TTT CTA AGA GAA AGC GCG ATG AGG TTA GGT       5139
Glu Lys Phe Val Asp Asn Phe Leu Arg Glu Ser Ala Met Arg Leu Gly
325                 330                 335                 340

AAA AGG CAC AAA CAT TTT ACT AAT GGA CTT GAA GTA GTG GGA ATT AAA       5187
Lys Arg His Lys His Phe Thr Asn Gly Leu Glu Val Val Gly Ile Lys
                345                 350                 355

TGC TTG AAA AAT AAT GCG GGG CTT TTT TGT TGG ATG GAT TTG CGT CCA       5235
Cys Leu Lys Asn Asn Ala Gly Leu Phe Cys Trp Met Asp Leu Arg Pro
            360                 365                 370

CTT TTA AGG GAA TCG ACT TTC GAT AGC GAA ATG TCG TTA TGG AGA GTT       5283
Leu Leu Arg Glu Ser Thr Phe Asp Ser Glu Met Ser Leu Trp Arg Val
        375                 380                 385

ATT ATA AAC GAT GTT AAG CTT AAC GTC TCG CCT GGA TCT TCG TTT GAA       5331
Ile Ile Asn Asp Val Lys Leu Asn Val Ser Pro Gly Ser Ser Phe Glu
        390                 395                 400

TGT CAA GAG CCA GGG TGG TTC CGA GTT TGT TTT GCA AAT ATG GAT GAT       5379
Cys Gln Glu Pro Gly Trp Phe Arg Val Cys Phe Ala Asn Met Asp Asp
405                 410                 415                 420

GGA ACG GTT GAT ATT GCG CTC GCG AGG ATT CGG AGG TTC GTA GGT GTT       5427
Gly Thr Val Asp Ile Ala Leu Ala Arg Ile Arg Arg Phe Val Gly Val
                425                 430                 435

GAG AAA AGT GGA GAT AAA TCG AGT TCG ATG GAA AAG AAG CAA CAA TGG       5475
Glu Lys Ser Gly Asp Lys Ser Ser Met Glu Lys Lys Gln Gln Trp
            440                 445                 450

AAG AAG AAT AAT TTG AGA CTT AGT TTT TCG AAA AGA ATG TAT GAT GAA       5523
Lys Lys Asn Asn Leu Arg Leu Ser Phe Ser Lys Arg Met Tyr Asp Glu
        455                 460                 465

AGT GTT TTG TCA CCA CTT TCG TCA CCT ATT CCT CCC TCA CCA TTA GTT       5571
Ser Val Leu Ser Pro Leu Ser Ser Pro Ile Pro Pro Ser Pro Leu Val
        470                 475                 480

CGT TAAGACTTAA TTAAAAGGGA AGAATTTAAT TTATGTTTTT TTATATTTTG            5624
Arg
485

AAAAAAATTT GTAAGAATAA GATTATAATA GGAAAAGAAA ATAAGTATGT AGGATGAGGA     5684

GTATTTTCAG AAATAGTTGT TAGCGTATGT ATTGACAACT GGTCTATGTA CTTAGACATC     5744

ATAATTTGTC TTAGCTAATT AATGAATGCA AAAGTGAAGT TATGTTATGA CTCTTAGAAT     5804
```

-continued

```
CTTTTGATTT ATTGGACTTT CTCGATTATA TTGTTATTAT TAAATTTCAT ATATTTTATA    5864

TATTTAAAAA GTGTCGTAAG TCATAATAAT TGACAAGATA TATGAAAACT TTACGATCAA    5924

AGATAAATTT GTTAAATTT TAAAATTTAA AGTGTGTCAC ATAAATTGAG ATGGAGAGAT     5984

TATGGTGTTT GTGTATATTT TAATGGAAAA ATACAGTGCG TGTTTGTGGG GGATTGACTC    6044

CAGATGATAG AGTAGAAATG GATCTCCTAA TTTTTTTATT TATGTTTTAC TTTATCGAGG    6104

GTCTATCAAA AATAATTTAT CTATTTTTA AATAGAGATA AAGTCTGACA TACTCTTTTT    6164

ACTTGTATTT ATATGTCATG ATTTTGATTA GGAGTTTGGA TTTTCTCTAC GTTCAAATAC   6224

AAATTAAACT ATAATGAGTT ATTTTCCCTA AATTTGGAGA AATTATCATT TGGAGATGAG   6284

TACACGATAA TAATGTCCTC TAATCAATTA CATCAAACAC AAAAACATTA TTAGAAATTC   6344

ACAATCTACA TGTTTGTCTA ATTAATCACA TCTTCATAGT TGATAAGTAG TACTTATCAT   6404

ACTTTGTAGT TTATGATTTC GAATAACTTG ACATATGATT AATTTTGTAA TACTACATTA   6464

CTGTTTATCA AACTTGTTTT TCGAATTCAT TTCTAGTAGT GTGTGGCATG ACTTGGACAA   6524

GAGAAATACA AATATTTTGA ATTTATTCCT ACTATACATT TTATTTTATT TTAATCTATA   6584

TATAAAAGAA TATCGTACAT ATTTATTAAT ATAAAATTTT GATATTTACT TTTTATTATA   6644

GAATTTGATA TCCAGTCAAA CCGCCACATA AATTGAGCCA ATATGTAAAT AGAAAATGTT   6704

GACAAAAGAA ATGGATTTAT TGGAAGACAA ACTGACATAG GGTCCAACTG AAAAGAGTTA   6764

AATTGTCGGA CGACTTTATA ATATTTTAGT CAACCCCACC CAAAGCCTTT TAAACTTAGA   6824

TAAATCCAAA AGATAATAAT TTTGATTGAT ATTTTATAAT GTATCTTTTT ATCATATTGA   6884

CATGTAGAAA AATTATAATT TATAATATTT TTTATATAGT TTTTAAATAT TTAAAATTTT   6944

TATTTAAAAT ATTAAATGAA TATATTTTAA CTTTAGTTAA TCAATGACTT TTAAAAAACG   7004

TAATATGACA ATTAAATGAA TAGAAAAAAT ATCGATTAAT AAGACTTTTG AGATGAAAAT   7064

ATTGTCTCAT GTGAACGATG CTAACGATGT CTCCAACATG GATTTTGCTT CCTTGGCTTT   7124

ATTTCATGAT TTAATATTTA TATTGAAATG ACTAAGGTAA GTAAAAAAAC AAATTTCATA   7184

TTAAAGTTTT GTTTGAGTTG AATTCAAGTT TTGATTATTT TTCTATTAGA AATCAGATCT   7244
```

(2) INFORMATION FOR SEQ ID NO:27:

(i) SEQUENCE CHARACTERISTICS:
        (A) LENGTH: 485 amino acids
        (B) TYPE: amino acid
        (D) TOPOLOGY: linear (ii) MOLECULE TYPE: protein (xi) SEQUENCE DESCRIPTION: SEQ ID NO:27:

```
Met Gly Phe Glu Ile Ala Lys Thr Asn Ser Ile Leu Ser Lys Leu Ala
 1               5                  10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
```

-continued

```
                    100                 105                 110
Arg Val Arg Phe Asp Pro Glu Arg Val Val Met Ala Gly Gly Ala Thr
            115                 120                 125

Gly Ala Asn Glu Thr Ile Ile Phe Cys Leu Ala Asp Pro Gly Asp Ala
        130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
        355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
            420                 425                 430

Phe Val Gly Val Glu Lys Ser Gly Asp Lys Ser Ser Met Glu Lys
        435                 440                 445

Lys Gln Gln Trp Lys Lys Asn Asn Leu Arg Leu Ser Phe Ser Lys Arg
    450                 455                 460

Met Tyr Asp Glu Ser Val Leu Ser Pro Leu Ser Pro Ile Pro Pro
465                 470                 475                 480

Ser Pro Leu Val Arg
                485
```

(2) INFORMATION FOR SEQ ID NO:28:

(i) SEQUENCE CHARACTERISTICS:
        (A) LENGTH: 493 amino acids (B) TYPE: amino acid
(C) STRANDEDNESS: single
(D) TOPOLOGY: linear (xi) SEQUENCE DESCRIPTION: SEQ ID NO:28:

```
Met Gly Phe His Gln Ile Asp Glu Arg Asn Gln Ala Leu Leu Ser Lys
 1               5                  10                  15

Ile Ala Leu Asp Asp Gly His Gly Glu Asn Ser Pro Tyr Phe Asp Gly
                 20                  25                  30

Trp Lys Ala Tyr Asp Asn Asp Pro Phe His Pro Glu Asn Asn Pro Leu
             35                  40                  45

Gly Val Ile Gln Met Gly Leu Ala Glu Asn Gln Leu Ser Phe Asp Met
         50                  55                  60

Ile Val Asp Trp Ile Arg Lys His Pro Glu Ala Ser Ile Cys Thr Pro
 65                  70                  75                  80

Glu Gly Leu Glu Arg Phe Lys Ser Ile Ala Asn Phe Gln Asp Tyr His
                 85                  90                  95

Gly Leu Pro Glu Phe Arg Asn Ala Ile Ala Asn Phe Met Gly Lys Val
            100                 105                 110

Arg Gly Gly Arg Val Lys Phe Asp Pro Ser Arg Ile Val Met Gly Gly
        115                 120                 125

Gly Ala Thr Gly Ala Ser Glu Thr Val Ile Phe Cys Leu Ala Asp Pro
130                 135                 140

Gly Asp Ala Phe Leu Val Pro Ser Pro Tyr Tyr Ala Gly Phe Asp Arg
145                 150                 155                 160

Asp Leu Lys Trp Arg Thr Arg Ala Gln Ile Ile Arg Val His Cys Asn
                165                 170                 175

Arg Ser Asn Asn Phe Gln Val Thr Lys Ala Ala Leu Glu Ile Ala Tyr
            180                 185                 190

Lys Lys Ala Gln Glu Ala Asn Met Lys Val Lys Gly Val Ile Ile Thr
        195                 200                 205

Asn Pro Ser Asn Pro Leu Gly Thr Thr Tyr Asp Arg Asp Thr Leu Lys
210                 215                 220

Thr Leu Val Thr Phe Val Asn Gln His Asp Ile His Leu Ile Cys Asp
225                 230                 235                 240

Glu Ile Tyr Ser Ala Thr Val Phe Lys Ala Pro Thr Phe Thr Ser Ile
                245                 250                 255

Ala Glu Ile Val Glu Gln Met Glu His Cys Lys Lys Glu Leu Ile His
            260                 265                 270

Ile Leu Tyr Ser Leu Ser Lys Asp Met Gly Leu Pro Gly Phe Arg Val
        275                 280                 285

Gly Ile Ile Tyr Ser Tyr Asn Asp Val Val Val Arg Arg Ala Arg Gln
290                 295                 300

Met Ser Ser Phe Gly Leu Val Ser Ser Gln Thr Gln His Leu Leu Ala
305                 310                 315                 320

Ala Met Leu Ser Asp Glu Asp Phe Val Asp Lys Phe Leu Ala Glu Asn
                325                 330                 335

Ser Lys Arg Val Gly Glu Arg His Ala Arg Phe Thr Lys Glu Leu Asp
            340                 345                 350

Lys Met Gly Ile Thr Cys Leu Asn Ser Asn Ala Gly Val Phe Val Trp
        355                 360                 365

Met Asp Leu Arg Arg Leu Leu Lys Asp Gln Thr Phe Lys Ala Glu Met
370                 375                 380

Glu Leu Trp Arg Val Ile Ile Asn Glu Val Lys Leu Asn Val Ser Pro
```

```
385                 390                 395                 400
Gly Ser Ser Phe His Val Thr Glu Pro Gly Trp Phe Arg Val Cys Phe
                405                 410                 415

Ala Asn Met Asp Asp Asn Thr Val Asp Val Ala Leu Asn Arg Ile His
                420                 425                 430

Ser Phe Val Glu Asn Ile Asp Lys Lys Glu Asp Asn Thr Val Ala Met
                435                 440                 445

Pro Ser Lys Thr Arg His Arg Asp Asn Lys Leu Arg Leu Ser Phe Ser
                450                 455                 460

Phe Ser Gly Arg Arg Tyr Asp Glu Gly Asn Val Leu Asn Ser Pro His
465                 470                 475                 480

Thr Met Ser Pro His Ser Pro Leu Val Ile Ala Lys Asn
                485                 490

(2) INFORMATION FOR SEQ ID NO:29:

(i) SEQUENCE CHARACTERISTICS:
        (A) LENGTH: 494 amino acids
        (B) TYPE: amino acid
        (C) STRANDEDNESS: single
        (D) TOPOLOGY: linear (xi) SEQUENCE DESCRIPTION: SEQ ID NO:29:

Met Gly Phe His Gln Ile Asp Glu Arg Asn Gln Ala Leu Leu Ser Lys
1                   5                   10                  15

Ile Ala Ile Asp Asp Gly His Gly Glu Asn Ser Ala Tyr Phe Asp Gly
                20                  25                  30

Trp Lys Ala Tyr Asp Asn Asn Pro Phe His Pro Glu Asn Asn Pro Leu
                35                  40                  45

Gly Val Ile Gln Met Gly Leu Ala Glu Asn Gln Leu Ser Phe Gly Met
            50                  55                  60

Ile Val Asp Trp Ile Arg Lys His Pro Glu Ala Ser Ile Cys Thr Pro
65                  70                  75                  80

Glu Gly Leu Glu Lys Phe Lys Ser Ile Ala Asn Phe Gln Asp Tyr His
                85                  90                  95

Gly Leu Gln Glu Phe Arg Lys Ala Met Ala Ser Phe Met Gly Lys Val
                100                 105                 110

Arg Gly Gly Arg Val Lys Phe Asp Pro Ser Arg Ile Val Met Gly Gly
            115                 120                 125

Gly Ala Thr Gly Ala Ser Glu Thr Val Ile Phe Cys Leu Ala Asp Pro
            130                 135                 140

Gly Asp Ala Phe Leu Val Pro Ser Pro Tyr Tyr Ala Ala Phe Asp Arg
145                 150                 155                 160

Asp Leu Lys Trp Arg Thr Arg Ala Gln Ile Ile Pro Val His Cys Asn
                165                 170                 175

Ser Ser Asn Asn Phe Gln Val Thr Glu Ala Ala Leu Glu Ile Ala Tyr
                180                 185                 190

Lys Lys Ala Gln Glu Ala Asn Met Lys Val Lys Gly Val Ile Ile Thr
            195                 200                 205

Asn Pro Ser Asn Pro Leu Gly Thr Thr Tyr Asp Arg Asp Thr Leu Lys
            210                 215                 220

Thr Leu Val Thr Phe Val Asn Gln His Asp Ile His Leu Ile Cys Asp
225                 230                 235                 240

Glu Ile Tyr Ser Ala Thr Val Phe Lys Ala Pro Thr Phe Thr Ser Ile
                245                 250                 255
```

```
Ala Glu Ile Val Glu Gln Met Glu His Cys Lys Lys Glu Leu Ile His
            260                 265                 270

Ile Leu Tyr Ser Leu Ser Lys Asp Met Gly Leu Pro Gly Phe Arg Val
            275                 280                 285

Gly Ile Ile Tyr Ser Tyr Asn Asp Val Val Arg Arg Ala Arg Gln
            290                 295                 300

Met Ser Ser Phe Gly Leu Val Ser Ser Gln Thr Gln His Leu Leu Ala
305                 310                 315                 320

Ala Met Leu Ser Asp Glu Asp Phe Val Asp Lys Phe Leu Ala Glu Asn
                325                 330                 335

Ser Lys Arg Leu Gly Glu Arg His Ala Arg Phe Thr Lys Glu Leu Asp
                340                 345                 350

Lys Met Gly Ile Thr Cys Leu Asn Ser Asn Ala Gly Val Phe Val Trp
                355                 360                 365

Met Asp Leu Arg Arg Leu Leu Lys Asp Gln Thr Phe Lys Ala Glu Met
370                 375                 380

Glu Leu Trp Arg Val Ile Ile Asn Glu Val Lys Leu Asn Val Ser Pro
385                 390                 395                 400

Gly Ser Ser Phe His Val Thr Glu Pro Gly Trp Phe Arg Val Cys Phe
                405                 410                 415

Ala Asn Met Asp Asp Asn Thr Val Asp Val Ala Leu Asn Arg Ile His
                420                 425                 430

Ser Phe Val Glu Asn Ile Asp Lys Lys Glu Asp Asn Thr Val Ala Met
                435                 440                 445

Pro Ser Lys Thr Arg His Arg Asp Asn Lys Leu Arg Leu Ser Phe Ser
                450                 455                 460

Phe Ser Gly Arg Arg Tyr Asp Lys Gly Asn Val Leu Asn Ser Pro His
465                 470                 475                 480

Thr Met Ser Pro His Ser Pro Leu Val Arg Ala Arg Thr Tyr
                485                 490

(2) INFORMATION FOR SEQ ID NO:30:

(i) SEQUENCE CHARACTERISTICS:
        (A) LENGTH: 485 amino acids
        (B) TYPE: amino acid
        (C) STRANDEDNESS: single
        (D) TOPOLOGY: linear (xi) SEQUENCE DESCRIPTION: SEQ ID NO:30:

Met Val Ser Ile Ser Lys Asn Gln Lys Gln Leu Leu Ser Lys
1               5                   10                  15

Ile Ala Thr Asn Asp Gly His Gly Glu Asn Ser Pro Tyr Phe Asp Gly
                20                  25                  30

Trp Lys Ala Tyr Ala Asn Asn Pro Phe His Leu Thr Asp Asn Pro Thr
            35                  40                  45

Gly Val Ile Gln Met Gly Leu Ala Glu Asn Gln Leu Cys Phe Asp Leu
50                  55                  60

Ile Gln Glu Trp Val Val Asn Asn Pro Lys Ala Ser Ile Cys Thr Val
65                  70                  75                  80

Glu Gly Ala Glu Asn Phe Gln Asp Ile Ala Ile Phe Gln Asp Tyr His
                85                  90                  95

Gly Leu Pro Glu Phe Arg Gln Ala Val Ala Arg Phe Met Glu Lys Val
                100                 105                 110

Arg Gly Asp Arg Val Thr Phe Asp Pro Asn Arg Ile Val Met Ser Gly
                115                 120                 125
```

```
Gly Ala Thr Gly Ala His Glu Met Leu Ala Phe Cys Leu Ala Asp Pro
    130                 135                 140

Gly Asp Ala Phe Leu Val Pro Thr Pro Tyr Tyr Pro Gly Phe Asp Arg
145                 150                 155                 160

Asp Leu Arg Trp Arg Thr Gly Val Gln Leu Phe Pro Val Val Cys Glu
                165                 170                 175

Ser Cys Asn Asp Phe Lys Val Thr Thr Lys Ala Leu Glu Glu Ala Tyr
            180                 185                 190

Glu Lys Ala Gln Gln Ser Asn Ile Lys Ile Lys Gly Leu Leu Ile Asn
        195                 200                 205

Asn Pro Ser Asn Pro Leu Gly Thr Leu Leu Asp Lys Asp Thr Leu Arg
    210                 215                 220

Asp Ile Val Thr Phe Ile Asn Ser Lys Asn Ile His Leu Val Cys Asp
225                 230                 235                 240

Glu Ile Tyr Ala Ala Thr Val Phe Asp Gln Pro Arg Phe Ile Ser Val
                245                 250                 255

Ser Glu Ile Val Glu Asp Met Ile Glu Cys Asn Lys Asp Leu Ile His
            260                 265                 270

Ile Val Tyr Ser Leu Ser Lys Asp Leu Gly Phe Pro Gly Phe Arg Val
        275                 280                 285

Gly Ile Val Tyr Ser Tyr Asn Asp Thr Val Val Asn Ile Ala Arg Lys
    290                 295                 300

Met Ser Ser Phe Gly Leu Val Ser Thr Gln Thr Gln His Leu Leu Ala
305                 310                 315                 320

Ser Met Leu Ser Asp Glu Val Phe Ile Asp Lys Phe Ile Ala Glu Ser
                325                 330                 335

Ser Glu Arg Leu Gly Glu Arg Gln Gly Met Phe Thr Lys Gly Leu Ala
            340                 345                 350

Glu Val Gly Ile Ser Thr Leu Lys Ser Asn Ala Gly Leu Phe Phe Trp
        355                 360                 365

Met Asp Leu Arg Arg Leu Leu Lys Glu Ala Thr Phe Asp Ser Glu Leu
    370                 375                 380

Glu Leu Trp Arg Ile Ile Ile Asn Glu Val Lys Leu Asn Val Ser Pro
385                 390                 395                 400

Gly Cys Ser Phe His Cys Ser Glu Pro Gly Trp Phe Arg Val Cys Phe
                405                 410                 415

Ala Asn Met Asp Asp Glu Thr Met Arg Ile Ala Leu Lys Arg Ile Ser
            420                 425                 430

Tyr Phe Val Leu Gln Pro Lys Gly Leu Asn Asn Ile Ala Ala Ile Lys
        435                 440                 445

Lys Gln Cys Ser Arg Arg Lys Leu Gln Ile Ser Leu Ser Phe Arg Arg
    450                 455                 460

Leu Asp His Glu Phe Met Asn Ser Pro Ala His Ser Pro Met Asn Ser
465                 470                 475                 480

Pro Leu Val Arg Thr
                485

(2) INFORMATION FOR SEQ ID NO:31:

(i) SEQUENCE CHARACTERISTICS:
        (A) LENGTH: 483 amino acids
        (B) TYPE: amino acid
        (C) STRANDEDNESS: single
        (D) TOPOLOGY: linear
```

(xi) SEQUENCE DESCRIPTION: SEQ ID NO:31:

```
Met Val Ser Ile Ser Lys Asn Asn Gln Lys Gln Gln Leu Leu Ser Lys
  1               5                  10                  15
Ile Ala Thr Asn Asp Gly His Gly Glu Asn Ser Pro Tyr Phe Asp Gly
                 20                  25                  30
Trp Lys Ala Tyr Ala Asn Asn Pro Phe His Leu Thr Asp Asn Pro Thr
             35                  40                  45
Gly Val Ile Gln Met Gly Leu Ala Glu Asn Gln Leu Cys Phe Asp Leu
 50                  55                  60
Ile Gln Glu Trp Met Val Asn Asn Pro Lys Ala Ser Ile Cys Thr Val
 65                  70                  75                  80
Glu Gly Ala Glu Asn Phe Gln Asp Ile Ala Ile Phe Gln Asp Tyr His
                 85                  90                  95
Gly Leu Pro Glu Phe Arg Gln Ala Val Ala Arg Phe Met Glu Lys Val
                100                 105                 110
Arg Gly Asp Arg Val Thr Phe Asp Pro Asn Arg Ile Val Met Ser Gly
            115                 120                 125
Gly Ala Thr Gly Ala His Glu Met Leu Ala Phe Cys Leu Ala Asp Pro
130                 135                 140
Gly Asp Ala Phe Leu Val Pro Thr Pro Tyr Tyr Pro Gly Phe Asp Arg
145                 150                 155                 160
Asp Leu Arg Trp Arg Thr Gly Val Gln Leu Phe Pro Val Val Cys Glu
                165                 170                 175
Ser Cys Asn Asp Phe Lys Val Thr Thr Lys Ala Leu Glu Glu Ala Tyr
            180                 185                 190
Glu Lys Ala Gln Gln Ser Asn Ile Lys Ile Lys Gly Leu Leu Ile Asn
            195                 200                 205
Asn Pro Ser Asn Pro Leu Gly Thr Leu Leu Asp Lys Asp Thr Leu Arg
210                 215                 220
Asp Ile Val Thr Phe Ile Asn Ser Lys Asn Ile His Leu Val Cys Asp
225                 230                 235                 240
Glu Ile Tyr Ala Ala Thr Val Phe Asp Gln Pro Arg Phe Ile Ser Val
                245                 250                 255
Ser Glu Met Val Glu Glu Met Ile Glu Cys Asn Thr Asp Leu Ile His
            260                 265                 270
Ile Val Tyr Ser Leu Ser Lys Asp Leu Gly Phe Pro Gly Phe Arg Val
            275                 280                 285
Gly Ile Val Tyr Ser Tyr Asn Asp Thr Val Val Asn Ile Ser Arg Lys
290                 295                 300
Met Ser Ser Phe Gly Leu Val Ser Thr Gln Thr Gln His Met Leu Ala
305                 310                 315                 320
Ser Met Leu Ser Asp Glu Ile Phe Val Glu Lys Phe Ile Ala Glu Ser
                325                 330                 335
Ser Glu Arg Leu Gly Lys Arg Gln Gly Met Phe Thr Lys Gly Leu Ala
            340                 345                 350
Gln Val Gly Ile Ser Thr Leu Lys Ser Asn Ala Gly Leu Phe Phe Trp
            355                 360                 365
Met Asp Leu Arg Arg Leu Leu Lys Glu Ala Thr Phe Asp Gly Glu Leu
370                 375                 380
Glu Leu Trp Arg Ile Ile Asn Glu Val Lys Leu Asn Val Ser Pro
385                 390                 395                 400
Gly Cys Ser Phe His Cys Ser Glu Pro Gly Trp Phe Arg Val Cys Phe
                405                 410                 415
```

```
Ala Asn Met Asp Asp Glu Thr Met Arg Ile Ala Leu Arg Arg Ile Arg
            420                 425                 430

Asn Phe Val Leu Gln Thr Lys Gly Leu Asn Asn Ile Ala Ala Ile Lys
            435                 440                 445

Lys Gln Cys Ser Arg Ser Lys Leu Gln Ile Ser Leu Ser Phe Arg Arg
            450                 455                 460

Leu Asp Asp Phe Asn Ser Pro Ala His Ser Pro Met Asn Ser Pro Leu
465                 470                 475                 480

Val Arg Thr (2) INFORMATION FOR SEQ ID NO:32:

(i) SEQUENCE CHARACTERISTICS:
        (A) LENGTH: 485 amino acids
        (B) TYPE: amino acid
        (C) STRANDEDNESS: single
        (D) TOPOLOGY: linear (xi) SEQUENCE DESCRIPTION: SEQ ID NO:32:

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
            35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
            100                 105                 110

Arg Val Arg Phe Asp Pro Glu Arg Val Val Met Ala Gly Gly Ala Thr
            115                 120                 125

Gly Ala Asn Glu Thr Ile Ile Phe Cys Leu Ala Asp Pro Gly Asp Ala
        130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285
```

```
Ile Ile Tyr Ser Phe Asn Asp Asp Val Val Asn Cys Ala Arg Lys Met
    290                 295                 300
Ser Ser Phe Gly Leu Val Ser Thr Gln Thr Gln Tyr Phe Leu Ala Ala
305                 310                 315                 320
Met Leu Ser Asp Glu Lys Phe Val Asp Asn Phe Leu Arg Glu Ser Ala
                325                 330                 335
Met Arg Leu Gly Lys Arg His Lys His Phe Thr Asn Gly Leu Glu Val
                340                 345                 350
Val Gly Ile Lys Cys Leu Lys Asn Asn Ala Gly Leu Phe Cys Trp Met
                355                 360                 365
Asp Leu Arg Pro Leu Leu Arg Glu Ser Thr Phe Asp Ser Glu Met Ser
370                 375                 380
Leu Trp Arg Val Ile Ile Asn Asp Val Lys Leu Asn Val Ser Pro Gly
385                 390                 395                 400
Ser Ser Phe Glu Cys Gln Glu Pro Gly Trp Phe Arg Val Cys Phe Ala
                405                 410                 415
Asn Met Asp Asp Gly Thr Val Asp Ile Ala Leu Ala Arg Ile Arg Arg
                420                 425                 430
Phe Val Gly Val Glu Lys Ser Gly Asp Lys Ser Ser Ser Met Glu Lys
                435                 440                 445
Lys Gln Gln Trp Lys Lys Asn Asn Leu Arg Leu Ser Phe Ser Lys Arg
    450                 455                 460
Met Tyr Asp Glu Ser Val Leu Ser Pro Leu Ser Ser Pro Ile Pro Pro
465                 470                 475                 480
Ser Pro Leu Val Arg
                485

(2) INFORMATION FOR SEQ ID NO:33:

(i) SEQUENCE CHARACTERISTICS:
        (A) LENGTH: 469 amino acids
        (B) TYPE: amino acid
        (C) STRANDEDNESS: single
        (D) TOPOLOGY: linear (xi) SEQUENCE DESCRIPTION: SEQ ID NO:33:

Met Lys Leu Leu Ser Glu Lys Ala Thr Cys Asn Ser His Gly Gln Asp
1               5                   10                  15
Ser Ser Tyr Phe Leu Gly Trp Gln Glu Tyr Glu Lys Asn Pro Tyr Asp
                20                  25                  30
Glu Ile Gln Asn Pro Lys Gly Ile Ile Gln Met Gly Leu Ala Glu Asn
                35                  40                  45
Gln Leu Ser Phe Asp Leu Leu Glu Ser Trp Leu Ala Gln Asn Pro Asp
    50                  55                  60
Ala Ala Gly Phe Lys Arg Asn Gly Glu Ser Ile Phe Arg Glu Leu Ala
65                  70                  75                  80
Leu Phe Gln Asp Tyr His Gly Leu Pro Ala Phe Lys Asn Ala Met Thr
                85                  90                  95
Lys Phe Met Ser Glu Ile Arg Gly Asn Arg Val Ser Phe Asp Ser Asn
                100                 105                 110
Asn Leu Val Leu Thr Ala Gly Ala Thr Ser Ala Asn Glu Thr Leu Met
                115                 120                 125
Phe Cys Leu Ala Asn Gln Gly Asp Ala Phe Leu Leu Pro Thr Pro Tyr
    130                 135                 140
Tyr Pro Gly Phe Asp Arg Asp Leu Lys Trp Arg Thr Gly Ala Glu Ile
```

```
                145                 150                 155                 160
Val Pro Ile His Cys Ser Ser Asn Gly Phe Arg Ile Thr Glu Ser
                165                 170                 175
Ala Leu Glu Glu Ala Tyr Leu Asp Ala Lys Lys Arg Asn Leu Lys Val
                180                 185                 190
Lys Gly Val Leu Val Thr Asn Pro Ser Asn Pro Leu Gly Thr Thr Leu
                195                 200                 205
Asn Arg Asn Glu Leu Glu Leu Leu Thr Phe Ile Asp Glu Lys Gly
                210                 215                 220
Ile His Leu Ile Ser Asp Glu Ile Tyr Ser Gly Thr Val Phe Asn Ser
225                 230                 235                 240
Pro Gly Phe Val Ser Val Met Glu Val Leu Ile Glu Lys Asn Tyr Met
                245                 250                 255
Lys Thr Arg Val Trp Glu Arg Val His Ile Val Tyr Ser Leu Ser Lys
                260                 265                 270
Asp Leu Gly Leu Pro Gly Phe Arg Ile Gly Ala Ile Tyr Ser Asn Asp
                275                 280                 285
Glu Met Val Val Ser Ala Ala Thr Lys Met Ser Ser Phe Gly Leu Val
                290                 295                 300
Ser Ser Gln Thr Gln Tyr Leu Leu Ser Cys Met Leu Ser Asp Lys Lys
305                 310                 315                 320
Phe Thr Lys Lys Tyr Ile Ser Glu Asn Gln Lys Arg Leu Lys Lys Arg
                325                 330                 335
His Ala Met Leu Val Lys Gly Leu Lys Ser Ala Gly Ile Asn Cys Leu
                340                 345                 350
Glu Ser Asn Ala Gly Leu Phe Cys Trp Val Asp Met Arg His Leu Leu
                355                 360                 365
Ser Ser Asn Asn Phe Asp Ala Glu Met Asp Leu Trp Lys Lys Ile Val
370                 375                 380
Tyr Asp Val Gly Leu Asn Ile Ser Pro Gly Ser Ser Cys His Cys Thr
385                 390                 395                 400
Glu Pro Gly Trp Phe Arg Val Cys Phe Ala Asn Met Ser Glu Asp Thr
                405                 410                 415
Leu Asp Leu Ala Met Arg Arg Ile Lys Asp Phe Val Glu Ser Thr Ala
                420                 425                 430
Pro Asn Ala Thr Asn His Gln Asn Gln Gln Gln Ser Asn Ala Asn Ser
                435                 440                 445
Lys Lys Lys Ser Phe Ser Lys Trp Val Phe Arg Leu Ser Phe Asn Asp
                450                 455                 460
Arg Gln Arg Glu Arg
465

(2) INFORMATION FOR SEQ ID NO:34:

(i) SEQUENCE CHARACTERISTICS:
        (A) LENGTH: 476 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 281
        (D) OTHER INFORMATION: /note= "This position is S or A."

(ix) FEATURE:
        (A) NAME/KEY: Modified-site
        (B) LOCATION: 284
```

(D) OTHER INFORMATION: /note= "This position is M or r."

(ix) FEATURE:
    (A) NAME/KEY: Modified-site
    (B) LOCATION: 286
    (D) OTHER INFORMATION: /note= "This position is F or L."

(ix) FEATURE:
    (A) NAME/KEY: Modified-site
    (B) LOCATION: 288
    (D) OTHER INFORMATION: /note= "This position is G or N."

(xi) SEQUENCE DESCRIPTION: SEQ ID NO:34:

```
Met Asp Leu Glu Thr Ser Glu Ile Ser Asn Tyr Lys Ser Ser Ala Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
            35                  40                  45

Asn Leu Asn Gly Val Ile Gln Met Gly Leu Ala Glu Asn Gln Leu Ser
        50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
                100                 105                 110

Glu Lys Thr Arg Gly Gly Lys Val Lys Phe Asp Ala Lys Arg Val Val
            115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
                180                 185                 190

Glu Ala Tyr Glu Lys Gly Gln Gln Ala Asn Val Lys Ile Lys Gly Leu
            195                 200                 205

Ile Leu Thr Asn Pro Cys Asn Pro Leu Gly Thr Ile Leu Asp Arg Asp
210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
                245                 250                 255

Val Ser Ile Ala Glu Ile Ile Asn Glu Asp Asn Cys Ile Asn Lys Asp
                260                 265                 270

Leu Val His Ile Val Ser Ser Leu Xaa Lys Asp Xaa Gly Xaa Pro Xaa
            275                 280                 285

Phe Arg Val Gly Ile Val Tyr Ser Phe Asn Asp Asp Val Val Asn Cys
290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
                340                 345                 350
```

-continued

```
Gly Leu Glu Glu Ile Gly Ile Lys Cys Leu Glu Ser Asn Ala Gly Val
        355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
            405                 410                 415

Val Cys Phe Ala Asn Ile Asp Asp Gln Thr Met Glu Ile Ala Leu Ala
            420                 425                 430

Arg Ile Arg Met Phe Met Asp Ala Tyr Asn Asn Val Asn Lys Asn Gly
        435                 440                 445

Val Met Lys Asn Lys His Asn Gly Arg Gly Thr Thr Tyr Asp Leu Thr
    450                 455                 460

Pro Gln Met Gly Ser Thr Met Lys Met Leu Leu Ala
465                 470                 475
```

CONTROL OF FRUIT RIPENING THROUGH GENETIC CONTROL OF ACC SYNTHASE SYNTHESIS

This application is a continuation of application Ser. No. 07/862,493, filed Apr. 2, 1992, now abandoned, which is a continuation-in-part of U.S. Ser. No. 07/579,896, filed Sep. 10, 1990 ABN.

FIELD OF THE INVENTION

The invention relates to the use of genetic materials related to the plant enzyme ACC synthase to control plant development, and in particular, senescence and ripening of fruit. ACC synthase is essential for the production of ethylene in higher plants; ethylene is a determinant of fruit ripening.

BACKGROUND ART

The enzyme ACC synthase is essential to the production of ethylene in higher plants. It is well known that ethylene is related to various events in plant growth and development including fruit ripening, seed germination, abscission, and leaf and flower senescence. Ethylene production is strictly regulated by the plant and is induced by a variety of external factors, including the application of auxins, wounding, anaerobic conditions, viral infection, elicitor treatment, chilling, drought, and ions such as cadmium and lithium ions. A review of ethylene production and effects in plants may be found, for example, in Abeles, F. B., "Ethylene in Plant Biology" (1983) Academic Press, New York.

It is also known that the synthesis of ethylene in higher plants includes a rate limiting step which is the conversion of S-adenosyl methionine (AdoMet) to 1-aminocyclopropane-1-carboxylic acid (ACC). This conversion is catalyzed by the enzyme ACC synthase (EC4.4.1.14). This enzyme has been partially purified from several sources by Nakajima, N., et al., *Plant Cell Physiol* (1986) 27:969–980; Mehta, A. M., et al., *Proc Natl Acad Sci USA* (1988) 85:8810–8814; Nakajima, N., et al., *Plant Cell Physiol* (1988) 29:989–990; Tsai, D. S., et al., *Arch Biochem Biophys* (1988) 264:632–640; Bleecker, A. B., et al., *Proc Natl Acad Sci USA* (1986) 83:7755–7759; Privale, L. S., et al., *Arch Biochem Biophys* (1987) 253:333–340; Sato, S., et al., *Plant Physiol* (1988) 88:109–114; Van Der Straeten, D., et al., *Eur J Biochem* (1989) 182:639–647.

As the level of ACC synthase controls the production of ethylene, control of the level of this enzyme permits control of ethylene levels and thus regulation of the plant growth and development aspects that are controlled by ethylene. The availability of the relevant ACC synthase expression system and coding sequences permits control of ACC synthase expression and activity, as provided by the invention herein.

In an abstract published in connection with the UCLA Symposia on Molecular and Cellular Biology, held Mar. 27–Apr. 7, 1989, as published in *J Cell Biochem* (1989) Supp. 13D, page 241, Theologis, A., et al. disclosed that a cDNA sequence designated pACC1 from Cucurbita (zucchini) fruits had been isolated by screening a cDNA library in λgt11 with antiserum prepared by subtraction purification using proteins obtained from tissues that were induced and uninduced for ACC synthase. The pACC1 clone was reported to hybridize to a 1900 nucleotide mRNA that was induced by auxin and lithium ions. The abstract further reports that using the Cucurbita cDNA as a probe, cDNA and genomic clones encoding tomato ACC synthase were isolated, and that the authenticity of these clones had been confirmed by recovery of enzyme activity after expression in *E. coli*. An expanded version of the work described in this abstract was published by Sato, T. et al., *Proc Natl Acad Sci USA* (1989) 86:6621–6625. However, neither the abstract nor the paper disclosed the details of the purification of the native ACC synthase. An additional abstract further reporting this work and indicating that the ACC synthase in tomatoes was encoded by a single-copy gene was published in connection with the succeeding UCLA Symposium on Molecular and Cellular Biology in *J Cell Biochem* (1990) Supp. 14E, page 358. This symposium was held Mar. 31–Apr. 22, 1990.

Two additional accounts of the recovery of cDNA encoding the ACC synthase of Cucurbita fruit, and further indicating that the Cucurbita genome contains two linked ACC synthase genes which are transcribed in opposing directions were published in *Horticultural Biotechnol* (1990) Wiley-Liss, Inc., pp. 237–246 and in *Plant Gene Transfer* (1990) Alan R. Liss, Inc., pp. 289–299. A further summary was presented in an abstract published in connection with Plant Molecular Biology Meeting conducted by the NATO Advanced Study Institute held in Bavaria on May 14–23, 1990 and at the Third International Symposium of the Society of Chinese Bioscientists in America, held Jun. 24–30, 1990. None of these publications disclosed the nucleotide sequences of either the coding or control regions for any of the ACC synthase genes.

Sato, T. et al., *J Biol Chem* (1991) 266:3752–3759 described the isolation, properties, and expression in *E. coli* of the 50 kd ACC synthase of Cucurbita as encoded by the cDNA prepared from messenger RNA present in fruits induced with auxin and lithium ion. The preparation of this cDNA and the complete deduced amino acid sequence thereof are described hereinbelow in Example 1 and FIG. 1.

Van der Straeten, D., et al. reported the cloning and sequences of cDNAs purportedly encoding ACC synthase from tomato (*Proc Natl Acad Sci USA* (1990) 87:4859–4863). Although the cDNA, which corresponded to an open reading frame of approximately 55 kd, produced a 55 kd peptide in *E. coli*, the authors were unable to show ACC synthase activity in the extracts of *E. coli* producing this protein. Comparison with the sequences described in the present invention shows that two amino acid residues that are invariant among the polypeptides found herein are miscoded in the vector reported by van der Straeten; specifically, Leu322 was changed to Pro322 and Pro399 was changed to Leu399. It is believed that these changes in the highly conserved regions lead to inactivated forms of this protein.

SUMMARY OF THE INVENTION

The invention provides recombinant materials and techniques which permit control of the level of ACC synthase in plants and portions thereof. The invention herein demonstrates that although ACC synthases in zucchini and tomato are encoded by a multigene family, only certain members of this family are expressed to produce the ACC synthase associated with ripening fruit. Thus, it is the expression of these specific members of the multigene family which must be controlled in order to influence the level of production of the relevant ACC synthase. Further, the provision of the sequences encoding ACC synthases of a large family of these enzymes permits designation of conserved regions so that primers suitable for polymerase chain reaction-based recovery of the corresponding genomic regions in other plants can be accomplished. This permits the control of plant development and activity in a wide variety of plant materials of commercial interest.

Accordingly, in one aspect, the invention is directed to methods to control ACC synthase production using the expression control and coding sequences for the relevant ACC synthase in either a sense or an antisense construct or by replacing the ACC synthase gene by a mutated form thereof.

The invention further includes materials useful in producing transgenic plants which are overproducers of or are deficient in ACC synthase and to the plants thus obtained. In another aspect, the invention is directed to methods to retrieve ACC synthase genes, including their control sequences, from higher plants using primers representing conserved regions of the ACC synthase genes in tomato and Cucurbita. The invention is also directed to primers useful in this technique. Finally, the invention is directed to recombinant materials related to ACC synthase and to isolated and purified ACC synthase per se.

BRIEF DESCRIPTION OF THE DRAWINGS

FIGS. 1B(i)–1B(ii) (SEQ ID NO:18 and SEQ ID NO:19) shows the nucleotide and deduced amino acid sequence of one of these clones, pACC1.

FIG. 2A shows the alignment of the retrieved clones with the position of the coding sequences on the genome;

FIG. 2B shows a restriction map of the sequences on the genome;

FIG. 2C shows the functional portions of the two zucchini ACC synthase genes CP-ACC 1A and CP-ACC 1B.

FIGS. 3A–3F show the complete nucleotide sequence and deduced amino acid sequence of the genomic clone representing CP-ACC 1A. Both control regions and coding regions are shown.

FIGS. 4A–4E show the complete nucleotide sequence and deduced amino acid sequence of the genomic clone representing CP-ACC 1B. Both control regions and coding regions are shown.

FIGS. 5A–5C show the nucleotide and deduced amino acid sequence of a cDNA encoding the tomato ACC synthase.

FIGS. 9A–9E show the complete genomic sequence and deduced amino acid sequence of LE-ACC 2, including the control sequences.

FIGS. 10A–10B show a comparison of the deduced amino acid sequence from the two genomic zucchini clones and the four genomic tomato clones for ACC synthase (SEQ ID NO:28, SEQ ID NO:29, SEQ ID NO:30, SEQ ID NO:31, SEQ ID NO:32, SEQ ID NO:33, and SEQ ID NO:34).

FIG. 14 shows the construction of an expression vector for the tomato ACC-synthase gene oriented in the antisense direction.

DETAILED DESCRIPTION OF THE INVENTION

Figure 1A:
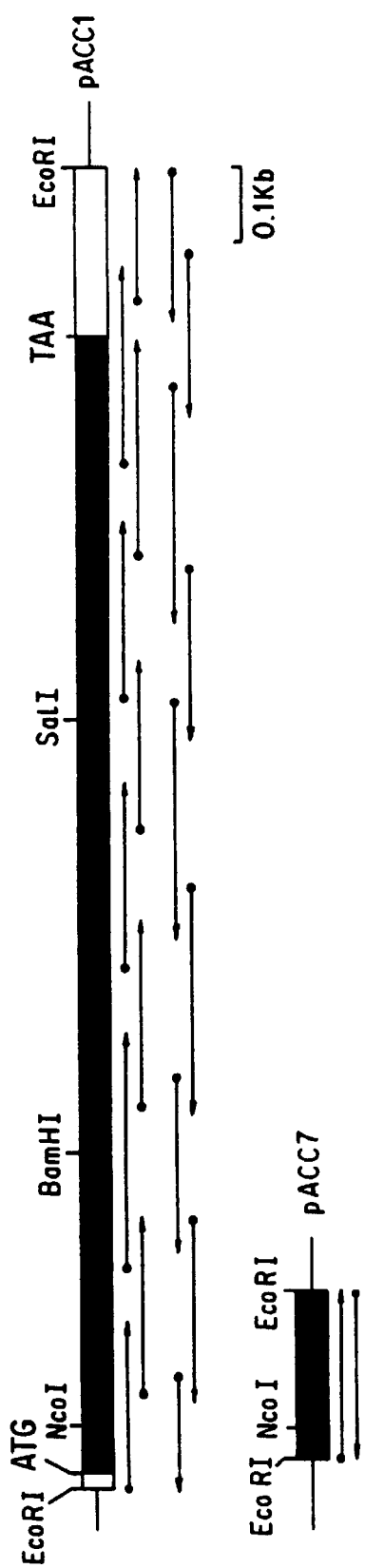
FIG. 1A shows a restriction map of two clones encoding the zucchini ACC synthase enzyme.

As shown herein, the genetic control of ACC synthase activity in higher plants is complex. The Cucurbita system contains at least two genomic regions encoding ACC synthases, ACC-1A and ACC-1B. The situation in tomato is even more complex wherein five independent ACC synthase regions are found in the genome, only one or two of which appear to be relevant to ripening of the fruit. While the coding regions of these various ACC synthases are highly homologous, the control regions responsible for their expression evidently are not.

The ripening of fruit is known to involve a complex series of reactions and interactions that is incompletely understood. A number of enzymes are known to be involved in the ripening process, including ACC synthase, the protein encoded by the TOM13 gene, and polygalactouronase. It is not clear to what extent the control of only one or a few of these enzymatic and other interactions would be successful in controlling ripening. Thus, it is not expected that the control of ACC synthase production, taken alone, would be adequate to control the ripening of fruit. However, as illustrated by the invention below, this is in fact the case.

While the various ACC synthases are generally active in a variety of plant tissues, the DNAs are not completely homologous, and therefore the use of the genetic materials for control of synthesis, for example, using an antisense strategy, does not translate across species.

The availability of a multiplicity of ACC synthases as provided by the invention permits comparison of their sequences to find conserved regions. These conserved regions are useful in the design of primers to mediate the recovery of ACC synthases in higher plants using the polymerase chain reaction.

Definitions and Abbreviations

The following abbreviations are used in the specification:

ACC=1-aminocyclopropane-1-carboxylic acid; AdoMet= S-adenosyl methionine; CaMV=cauliflower mosaic virus;

IPTG=the inducer isophosphothiogalactose; MTA=mehyl thioadenosine; CP=*Cucurbita pepo;* and LE=*Lycopersicon esculentum.*

As used herein, "recombinant" refers to a nucleic acid sequence which has been obtained by manipulation of genetic material using restriction enzymes, ligases, and similar recombinant techniques as described by, for example, Maniatis et al. "Recombinant," as used in the present application, does not refer to naturally-occurring genetic recombinations.

As defined herein, "ACC synthase" includes all enzymes which are capable of catalyzing the conversion of AdoMet to ACC and methyl thioadenosine (MTA). The amino acid sequence of the synthase may or may not be identical with the amino acid sequence which occurs natively in higher plants. An example of such native sequence is shown in FIG. 1 which occurs in the zucchini fruit (*Cucurbita pepo*). Naturally occurring allelic variants undoubtedly occur as well. Similar proteins are present in a wide variety of higher plants. In addition, artificially induced mutations are also included so long as they do not destroy activity. In general, conservative amino acid substitutions can be made for most of the amino acids in the primary structure as shown without affecting destruction of activity. Thus, the definition of ACC synthase used herein includes these variants which are derived by direct or indirect manipulation of the disclosed sequences.

It is also understood that the primary structure may be altered by post-translational processing or by subsequent chemical manipulation to result in a derivatized protein which contains, for example, glycosylation substituents, oxidized forms of, for example, cysteine or proline, conjugation to additional moieties, such as carriers, solid supports, and the like. These alterations do not remove the protein from the definition of ACC synthase so long as its capacity to convert AdoMet to ACC and MTA is maintained.

Thus, the identity of an enzyme as "ACC synthase" can be confirmed by its ability to effect the production of ethylene in an assay performed as follows: the enzyme to be tested is incubated with 200 μM AdoMet, 10 μM pyridoxal phosphate, 40 μg BSA in 200 mM Hepes buffer, pH 8.5 in a total volume of 600 μl at 30° C. for 30 minutes, and the amount of ACC formed is assayed by conversion to ethylene using hypochlorite as described, for example, by Lizada, C. C., et al., *Anal Biochem* (1979) 100:140–145. While alternative forms of assessment of ACC synthase can be devised, and variations on the above protocol are certainly permissible, the foregoing provides a definite criterion for the presence of ACC synthase activity and classification of a test protein as ACC synthase.

Figure 10A:
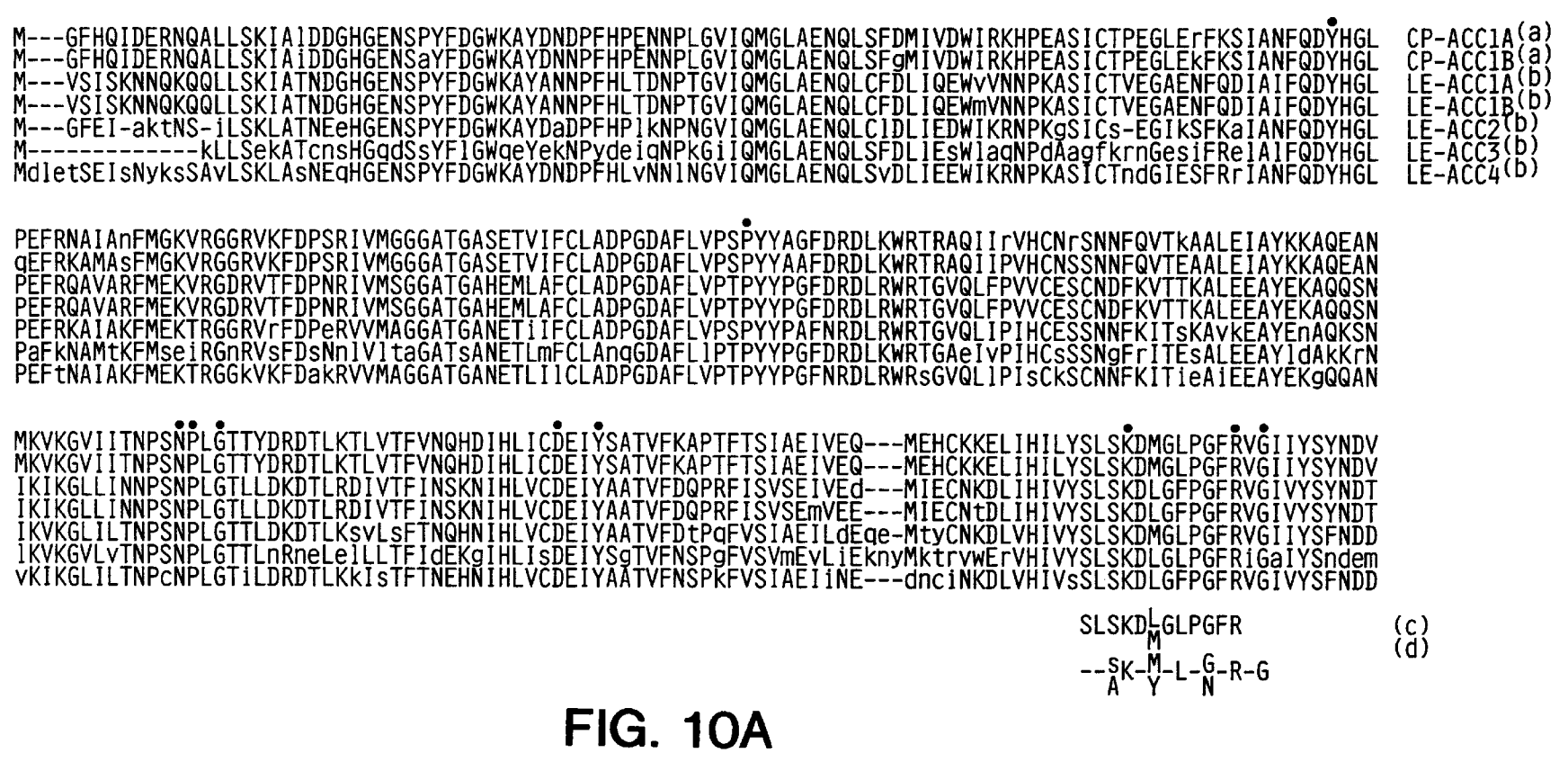

The amino acid sequences for several ACC synthases in tomato and zucchini are shown in FIG. 10 as published in Rottmann, W. H., et al., *J Mol Biol* (1991) 222:937–961. Preferred forms of the ACC synthases of the invention include those thus illustrated herein, and those derivable therefrom by systematic mutation of the genes. Such systematic mutation may be desirable to enhance the ACC synthase properties of the enzyme, to enhance the characteristics of the enzyme which are ancillary to its activity, such as stability, or shelf life, or may be desirable to provide inactive forms useful in the control of ACC activity in vivo, as further described below.

As described above, "ACC synthase" refers to a protein having the activity assessed by the assay set forth above; a "mutated ACC synthase" refers to a protein which does not necessarily have this activity, but which is derived by mutation of a DNA encoding an ACC synthase. By "derived from mutation" is meant both direct physical derivation from a DNA encoding the starting material ACC synthase using, for example, site specific mutagenesis or indirect derivation by synthesis of DNA having a sequence related to, but deliberately different from, that of the ACC synthase. As means for constructing oligonucleotides of the required length are available, such DNAs can be constructed wholly or partially from their individual constituent nucleotides.

As used herein, "higher plant" refers to those plants whose development and activity are controlled by ethylene. These include all common agricultural plants and various flowering species.

Derivation of Primers

FIG. 10 hereinbelow provides the comparative amino acid sequences of five ACC synthases encoded by the tomato genome and two encoded by the zucchini genome. The amino acid sequences are shown in a single-letter code in the order: CP-ACC 1A, CP-ACC 1B, LE-ACC 1A, LE-ACC 1B, LE-ACC2, LE-ACC3 and LE-ACC4. Completely conserved residues are indicated by shaded boxes; partially conserved residues are shown in capital letters; and residues not found in more than 1 polypeptide are shown as small letters. Gaps have been introduced to maximize matching. The sources of the sequences are : (a) zucchini (*Cucurbita pepo*); (b) tomato (*Lycopersicon esculentum*); (c) AdoMet- and pyridoxal phosphate-binding site in tomato ACC synthase, *Proc Natl Acad Sci USA* (1990) 87:7930–7934; and (d) consensus of the pyridoxal phosphate-binding site in aminotransferases (Mehta et al., *Eur J Biochem* (1989) 186:249–253). The filled circles indicate the 11 invariant amino acids conserved among ACC synthase and various aminotransferases.

As shown in FIG. 10, there are a number of conserved sequences in these proteins. Among these sequences are:

QMGLAENQ (L); (SEQ ID NO:1)
FQDYHG (L); (SEQ ID NO:2)
FMEK (V/T); (SEQ ID NO:3)
(K/A) A (L/V) E (E/I) AY; (SEQ ID NO:4)
GDAFL (V/I) P; (SEQ ID NO:5)
NPLGT; (SEQ ID NO:6)
SLSKD; (SEQ ID NO:7)
PGFR (V/I) G; (SEQ ID NO:8)
RVCFANMD; (SEQ ID NO:9)
MSSFGLVS; and (SEQ ID NO:10)
GWFRVCFAN (M/I). (SEQ ID NO:11)

These conserved amino acid sequences can be used to design degenerate consensus primers for amplification of the relevant genes in other higher plants. It has been shown by the inventors herein that these same regions are conserved in rice and in arabidopsis. Methods to design such degenerate primers using information related to codon preference and the like are well known in the art. The primers can then be used to conduct amplification by the polymerase chain reaction of the desired regions of the gene or cDNA extracted from other higher plants in order to isolate relevant ACC synthase encoding DNA.

Particularly useful are combinations of primers wherein the 5'→3' primer encodes MGLAENQ (SEQ ID NO:12)and the 3'→5' encodes FQDYHGL (SEQ ID NO2); or wherein the 5'→3' primer encodes FQDYHG (positions 1–6 of SEQ ID NO:2) and the 3'→5' primer encodes FMEK (V/T)R (SEQ ID NO:13); or wherein the 5'→3' primer encodes KA (L/V) EEAY (SEQ ID NO:14) and the 3'→5' primer encodes FPGFRVG (SEQ ID NO:15); or wherein the 5'→3' primer encodes KALEEAY (SEQ ID NO:16) and the 3'→5' primer encodes RVCFANMD (SEQ ID NO:9). In the foregoing, the amino acid sequences encoded are given in the N→C direction, regardless of whether the primer complements the 5'→3' region of the coding strand or is the complement in the corresponding 3'→1' region of the noncoding strand. Reference can be had to the gene sequences shown, for example, in FIGS. 3–5 and 9, which provide the complete coding sequence for various ACC genes to select the appropriate codons for the construction of primers.

Expression Systems

The coding sequence for ACC synthase and the DNA which represents the reverse transcript of the mRNA that is subsequently translated into ACC synthase can be included in expression systems suitable for higher plants. In at least three such expression systems, the changes in fruit associated with ethylene production can be retarded.

In one approach, a mutated form of the ACC synthase is supplied in an expression system to provide an alternative inactive monomer for coupling to the natively produced ACC synthase to effect dimer formation. As the ACC synthase is active as a dimer, inclusion of a mutated, inactivated form in the dimer destroys the effectiveness of the protein.

In a second approach, transformation of plants with a recombinant expression system for the relevant ACC synthase or a truncated form thereof may result, through an unknown mechanism, in suppression of the native production of ACC synthase, and may thus provide a means to inhibit, for example, the ripening of fruit in such plants. It has been shown previously that attempts to overexpress chalcone synthase in pigmented petunia petals by introducing the recombinant gene resulted in a suppression of the homologous native genes, thus resulting in a block in anthocyanine biosynthesis (Napoli, C., et al., *The Plant Cell* (1990) 2:279–289). These results were confirmed and extended to transformation with genes encoding dihydroflavonol-4-reductase genes in petunias by van der Krol, A. R., et al., *The Plant Cell* (1990) 2:291–299. It has also been found that transformation of a partial nopaline synthase gene into tobacco suppresses the expression of the endogenous corresponding gene, as reported by Goring, D. R., et al., *Proc Natl Acad Sci USA* (1991) 88:1770–1774. Similar results were described for the expression of a truncated tomato polygalactonuronase gene in transgenic tomatoes by Smith, C. J. S., et al., *Mol Gen Genet* (1990) 224:477–481. Elkind, Y., et al., *Proc Natl Acad Sci USA* (1990) 87:9057–9061, reported similar results in tobacco containing a heterologous phenylalanine ammonia-lyase gene. In general, it appears that supplying a truncated form of the relevant gene in the "sense" orientation suppresses the endogenous expression of the native gene, thus lowering the level of the gene product, despite the presence of the additional transformation system.

Alternatively, a DNA which is transcribed into the complement of mRNA that is translated by the host plant into ACC synthase can be provided to effect an antisense retardation of expression of the native gene. The following discussion describes control sequences and procedures which are useful in effecting expression in higher plants.

Especially useful in connection with the ACC synthase genes of the present invention are expression systems which are operable in plants. These include systems which are under control of a tissue-specific promoter, as well as those which involve promoters that are operable in all plant tissues.

Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, seed-specific promoters, etc. can also be used.

The cauliflower mosaic virus (CaMV) 35S promoter has been shown to be highly active in many plant organs and during many stages of development when integrated into the genome of transgenic plants including tobacco and petunia, and has been shown to confer expression in protoplasts of both dicots and monocots.

The CaMV 35S promoter has been demonstrated to be active in at least the following monocot and dicot plants with edible parts: blackberry, Rubus; blackberry/raspberry hybrid, Rubus, and red raspberry; carrot, *Daucus carota*; maize; potato, *Solanum tuberosum*; rice, *Oryza sativa*; strawberry, *Fragaria x ananassa*; and tomato, *Lycopersicon esculentum*.

The nopaline synthase (Nos) promoter has been shown to be active in at least the following monocot and dicot plants with edible parts: apple, *Malus pumila*; cauliflower, *Brassica oleracea*; celery, *Apium graveolens*; cucumber, *Cucumis sativus*; eggplant, *Solanum melongena*; lettuce, *Lactuca sativa*; potato, *Solanum tuberosum*; rye, *Secale cereale*; strawberry, *Fragaria x ananassa*; tomato, *Lycopersicon esculentum*; and walnut, *Juglans regia*.

Organ-specific promoters are also well known. For example, the E8 promoter is only transcriptionally activated during tomato fruit ripening, and can be used to target gene expression in ripening tomato fruit (Deikman and Fischer, *EMBO J* (1988) 7:3315; Giovannoni et al., *The Plant Cell* (1989) 1:53). The activity of the E8 promoter is not limited to tomato fruit, but is thought to be compatible with any system wherein ethylene activates biological processes.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans R Soc London* (1986) B314:343.

These mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

A somewhat more sophisticated procedure was described in *Molecular Biology of the Cell*, Second Edition (1989) pages 261–262, edited by Alberts et al., Garland Publishing Incorporated, New York. In this procedure, mRNAs enriched for organ-specific nucleic acid sequences were used to construct the cDNA library. This method was also applied to tomato by Lincoln et al., *Proc Natl Acad Sci* (1987) 84:2793, and resulted in the production of an E8 cDNA clone.

The gene that encodes the organ-specific mRNA is then isolated by constructing a library of DNA genomic sequences from the plant. The genome library is screened with the organ-specific cDNA clone, and the sequence is determined. The promoter is then isolated. These procedures are now considered to be routine and are described in detail in Sambrook et al., *Molecular Cloning: A Laboratory Manual,* Second Edition (1989) Cold Spring Harbor Laboratory Press, Cold Spring Harbor.

Either a constitutive promoter or a desired organ-specific promoter is then ligated to the gene encoding ACC synthase or a mutated form thereof using standard techniques now common in the art. The expression system may be further optimized by employing supplemental elements such as transcription terminators and/or enhancer elements.

Thus, for expression in plants, the recombinant expression cassette will contain in addition to the ACC synthase-encoding sequence, a plant promoter region, a transcription initiation site (if the coding sequence to be transcribed lacks one), and a transcription termination sequence. Unique restriction enzyme sites at the 5' and 3' ends of the cassette are typically included to allow for easy insertion into a pre-existing vector.

Sequences controlling eucaryotic gene expression have been extensively studied. Promoter sequence elements include the TATA box consensus sequence (TATAAT) (SEQ ID NO:17), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions -80 to -100, there is typically a promoter element with a series of adenines surrounding the trinucleotide G (or T) NG (Messing, J. et al., in *Genetic Engineering in Plants,* Kosage, Meredith and Hollaender, eds. (1983) pp. 221–227). Other sequences conferring tissue specificity, response to environmental signals, or maximum efficiency of transcription may also be found in the promoter region. Such sequences are often found within 400 bp of the transcription initiation site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

As stated above, any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids (Herrera-Estrella et al., *Nature* (1983) 303:209–213). Viral promoters include the 35S and 19S RNA promoters of cauliflower mosaic virus (O'Dell et al., *Nature* (1985) 313:810–812). Plant promoters include the ribulose-1,3-disphosphate carboxylase small subunit promoter and the phaseolin promoter. The promoter sequence from the E8 gene and other genes in which expression is induced by ethylene may also be used. The isolation and sequence of the E8 promoter is described in detail in Deikman and Fischer, *EMBO J* (1988) 7:3315–3320 which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently processed, DNA sequences which direct polyadenylation of the RNA are also commonly added to the vector construct (Alber and Kawasaki, *Mol and Appl Genet,* (1982) 1:419–434). Polyadenylation is of importance for expression of the ACC synthase-encoding RNA in plant cells. Polyadenylation sequences include, but are not limited to the Agrobacterium octopine synthase signal (Gielen et al., *EMBO J,* (1984) 3:835–846) or the nopaline synthase signal (Depicker et al., *Mol and Appl Genet* (1982) 1:561–573).

For in situ production of the antisense mRNA of ACC synthase, those regions of the ACC synthase gene which are transcribed into ACC synthase mRNA, including the untranslated regions thereof, are inserted into the expression vector under control of the promoter system in a reverse orientation. The resulting transcribed mRNA is then complementary to that normally produced by the plant. The presence of the antisense mRNA, as shown hereinbelow, effectively retards the activity of the native ACC synthase and, thus, the ripening of the fruit.

The resulting expression system or cassette is ligated into or otherwise constructed to be included in a recombinant vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range procaryotic origin of replication is included. A selectable marker for bacteria should also be included to allow selection of bacterial cells bearing the desired construct. Suitable procaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

In addition, vectors can also be constructed that contain in-frame ligations between the sequence encoding the ACC synthase protein and sequences encoding other molecules of interest resulting in fusion proteins, by techniques well known in the art.

When an appropriate vector is obtained, transgenic plants are prepared which contain the desired expression system. A number of techniques are available for transformation of plants or plant cells. All types of plants are appropriate subjects for "direct" transformation; in general, only dicots can be transformed using Agrobacterium-mediated infection.

In one form of direct transformation, the vector is microinjected directly into plant cells by use of micropipettes to mechanically transfer the recombinant DNA (Crossway, *Mol Gen Genetics* (1985) 202:179–185). In another form, the genetic material is transferred into the plant cell using polyethylene glycol (Krens, et al., *Nature* (1982) 296:72–74), or high velocity ballistic penetration by small particles with the nucleic acid either within the matrix of small beads or particles, or on the surface, is used (Klein, et al., *Nature* (1987) 327:70–73). In still another method protoplasts are fused with other entities which contain the DNA whose introduction is desired. These entities are minicells, cells, lysosomes or other fusible lipid-surfaced bodies (Fraley, et al., *Proc Natl Acad Sci USA* (1982) 79:1859–1863).

DNA may also be introduced into the plant cells by electroporation (Fromm et al., *Proc Natl Acad Sci USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another approach for DNA introduction into plant cells is by electroporation of pollen grains and subsequent in vivo fertilization, ultimately yielding transformed seed. This technique is described by Matthews et al., *Sex Plant Reprod* (1990) 3:147–151; and by Abdul-Baki et al., *Plant Science* (1990) 70:181–190.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303:179–189). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel, *Nature* (1981) 299:85–88), promoters (Lawton et al., *Plant Mol Biol* (1987) 9:315–324) and structural genes for antibiotic resistance as a selection factor (Fraley et al., *Proc Natl Acad Sci* (1983) 80:4803–4807).

There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* (1984) 3:1681–1689 and the non-oncogenic Ti plasmid pGV3850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721 and the non-oncogenic Ti plasmid PAL4404 described by Hoekema, et al., *Nature* (1983) 303:179–180. Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al., *Nature* (1984) 311:763–764). However, there is growing evidence now that certain monocots can be transformed by Agrobacterium. Using novel experimental approaches cereal species such as rye (de la Pena et al., *Nature* (1987) 325:274–276), maize (Rhodes et al., *Science* (1988) 240:204–207), and rice (Shimamoto et al., *Nature* (1989) 338:274–276) may now be transformed.

Identification of transformed cells or plants is generally accomplished by including a selectable marker in the transforming vector, or by obtaining evidence of successful bacterial infection.

Plant cells which have been transformed can also be regenerated using known techniques.

Plant regeneration from cultured protoplasts is described in Evans et al., *Handbook of Plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. For example, regeneration has been shown for dicots as follows: apple, *Malus pumila*; blackberry, Rubus, Blackberry/raspberry hybrid, Rubus, red raspberry, Rubus; carrot, *Daucus carota*; cauliflower, *Brassica oleracea*; celery, *Apium graveolens*; cucumber, *Cucumis sativus*; eggplant, *Solanum melongena*; lettuce, *Lactuca sativa*; potato, *Solanum tuberosum*; rape, *Brassica napus*; soybean (wild), *Glycine canescens;* strawberry, *Fragaria x ananassa*; tomato, *Lycopersicon esculentum*; walnut, *Juglans regia;* melon, *Cucumis melo;* grape, *Vitis vinifera;* mango, *Mangifera indica;* and for the following monocots: rice, *Oryza sativa*; rye, *Secale cereale*; and maize.

In addition, regeneration of whole plants from cells (not necessarily transformed) has been observed in: apricot, *Prunus armeniaca;* asparagus, *Asparagus officinalis;* banana, hybrid Musa; bean, *Phaseolus vulgaris;* cherry, hybrid Prunus; grape, *Vitis vinifera;* mango, *Mangifera indica;* melon, *Cucumis melo;* ochra, *Abelmoschus esculentus;* onion, hybrid Allium; orange, *Citrus sinensis;* papaya, *Carrica papaya;* peach, *Prunus persica* and plum, *Prunus domestica;* pear, *Pyrus communis;* pineapple, *Ananas comosus;* watermelon, *Citrullus vulgaris;* and wheat, *Triticum aestivum*.

The regenerated plants are transferred to standard soil conditions and cultivated in a conventional manner.

After the expression cassette is stably incorporated into regenerated transgenic plants, it can be transferred to other plants by sexual crossing. Any of a number of standard breeding techniques can be used, depending upon the species to be crossed.

The plants are grown and harvested using conventional procedures.

Antisense Expression

When the ACC synthase coding sequence is placed in correct orientation in the expression systems described above, the ACC synthase protein is produced. However, when the portion of the ACC synthase gene that is transcribed into mRNA is placed in the expression vector in the opposite orientation, the expression vector produces an antisense mRNA which can interfere with the indigenous production of this enzyme. Antisense technology can work at a variety of levels including hybridization to a messenger RNA encoding the ACC synthase, hybridization to single-stranded intermediates in the production of this mRNA, or triplex formation with the DNA duplex which contains the ACC synthase genes. All of these modalities can be employed in effecting antisense control of ACC synthase production.

As shown in Example 7 below, ripening of tomato fruit can be controlled and inhibited by suitable antisense expression of the ACC synthase coding sequence supplied in a vector under the control of the cauliflower 35S promoter. Other properties which are controlled by ethylene can also be influenced by appropriate choice of control systems and/or the particular ACC synthase encoded.

It is further shown below that the active form of ACC synthase in higher plants is a dimer. By supplying a mutated form of ACC synthase monomer, a decoy can be produced to obtain inactive monomer and thereby regulate the levels of ACC synthase in the plant. An additional embodiment of the invention involves the mutated ACC synthase and expression systems therefor.

The following examples are intended to illustrate but not to limit the invention.

EXAMPLE 1

Recovery of Zucchini ACC Synthase cDNA

A cDNA encoding ACC synthase in zucchini fruit was recovered as follows:

Slices 1 mm thick were prepared from zucchini fruits of the species *Cucurbita pepo*. To induce production of ACC synthase, slices were incubated for 18–24 hours in induction medium (50 $\mu$M potassium phosphate buffer, pH 6.8; 0.5 mM indole acetic acid (IAA); 0.1 mM benzyl adenine (BA); 50 mM LiCl; 0.6 mM aminooxyacetic acid (AOA); and 50 $\mu$g/ml chloramphenicol. (Uninduced tissue was prepared in a similar manner in 50 mM phosphate buffer, pH 6.8.)

Poly(A$^+$) RNA (mRNA) was isolated from 18-hr tissue prepared as described above, and in vitro translated in a wheat germ lysate as described by Theologis, A., et al., *J Mol Biol* (1985) 183:53–68, in the presence of labeled methionine (greater than 1,000 Ci/$\mu$mol) to verify the presence of ACC synthase encoding mRNA. A cDNA library was prepared in $\lambda$gt11 as described by Huynh, T. V., et al., in "DNA Cloning Techniques," Glover, E., ed. (1985) IRL Press, Oxford, 1:49–88. The insert sizes were 200–500 bp. The library was screened with purified ACC synthase antiserum prepared as follows:

The antisera were prepared to 1500-fold purified ACC synthase preparations. Purified ACC synthase can be prepared from tissue homogenates sequentially bound to and eluted from Butyl Toyopearl (Toyo Soda Tokyo), SP-Sephadex, and QAE-Sephadex. (Higher purification can be obtained by subsequent chromatography sequentially through columns containing Butyl Toyopearl, Sephacryl S-300, Bio Gel-HT, and finally FPLC mono-Q. The application of all of the foregoing steps results in approximately a 6000-fold purification.) The antibodies are prepared in New Zealand white rabbits by immunization protocols involving four immunizations at three-week intervals with 5000 nmol of ACC synthase activity/hr (specific activity 1500 nmol of ACC/hr/mg protein obtained from the Bio Gel-HT column). Crude antiserum (2 ml) was purified by incubation with 10 ml Sepharose 4B coupled with soluble proteins from intact noninduced Cucurbita fruit. This step removed antibodies immunoreactive with protein other than ACC synthase.)

Sixty-six immunoreactive clones were isolated by screening 1.4×10$^5$ $\lambda$gt11 recombinant clones with the purified antiserum. Upon rescreening, only 30 were, in fact, positive. Southern analysis showed that 19 clones represented the ACC synthase mRNA. One selected clone, pACC1, has an open reading frame encoding a 55.8 kd polypeptide. Another intensely immunoreactive clone, pACC7, was much shorter. FIG. 1A shows a restriction map of pACC1 and pACC7;

FIG. 1B shows the complete nucleotide sequence and deduced amino acid sequence for pACC1.

As shown in FIG. 1, pACC7 is identical to a portion of the sequence of pACC1. The open reading frame encodes a protein of 493 amino acids, corresponding to a 55.779 kd polypeptide.

The positive clones from the λgt11 library could also be used to prepare further purified antiserum for immunoblotting as follows:

The positive clones from the expression library were plated on *E. coli* strain Y1090 to obtain $10^5$ plaque-forming units per 90-mm plate. Dry nitrocellulose filters presoaked in 10 mM isopropyl β-D-thiogalactopyranoside (IPTG) were laid on the lawn after incubation for two hours at 42° C. and then incubated for an additional four hours at 37° C.

The filters were then soaked for 30 minutes in TBST (50 mM Tris HCl, pH 8.0; 0.14M NaCl; 0.05% Tween 20); 2% milk protein and then tested for ACC synthase expression by treating with 5 ml of diluted (1:500) purified ACC synthase antiserum (see below) per filter for two hours.

After washing five times at 10 minutes each with TBST, bound antibody was eluted by shaking for three minutes at room temperature with 0.2M glycine hydrochloride buffer, pH 2.3, containing 1% milk protein. The antibody solution was neutralized and used for immunoblotting.

EXAMPLE 2

Isolation of Zucchini Genomic Clones Encoding ACC Synthase

Four-day-old etiolated frozen zucchini seedlings were homogenized in 15% sucrose, 50 mM Tris-HCl, pH 8.5, 50 M EDTA-Na$_3$, 0.25M NaCl. The nuclei were pelleted by centrifugation at 4,000 rpm for 10 min at 4° C. and nuclear DNA was isolated by CsCl ethidium bromide equilibrium density gradient centrifugation. The recovered DNA was partially digested with Sau3A and electrophoretically separated on 0.5% low melting agarose.

DNA corresponding to 20 kb in size was ligated into EcoRI/BamHI cut EMBL 3λ (Frischauf, A. M., et al., *J Mol Biol* (1983) 170:827–842; Raleigh, E. A., et al., *Proc Natl Acad Sci USA* (1986) 83:9070–9074; Maniatis, T., et al., *Molecular Cloning* (1982) Cold Spring Harbor Laboratory, Cold Spring Harbor, N.Y.). The ligation mixture was packaged and the library was screened without amplification by plating on *E. coli* strain K802 and screening with nick translated ACC1 cDNA (the full length zucchini cDNA clone) as described by Benton, D., et al, *Science* (1977) 196:179–183. The isolated genomic sequences were mapped with restriction endonucleases and the appropriate DNA fragments which hybridize to the ACC1 cDNA were subcloned into the pUC18 and pUC19 plasmids.

Figure 2A:
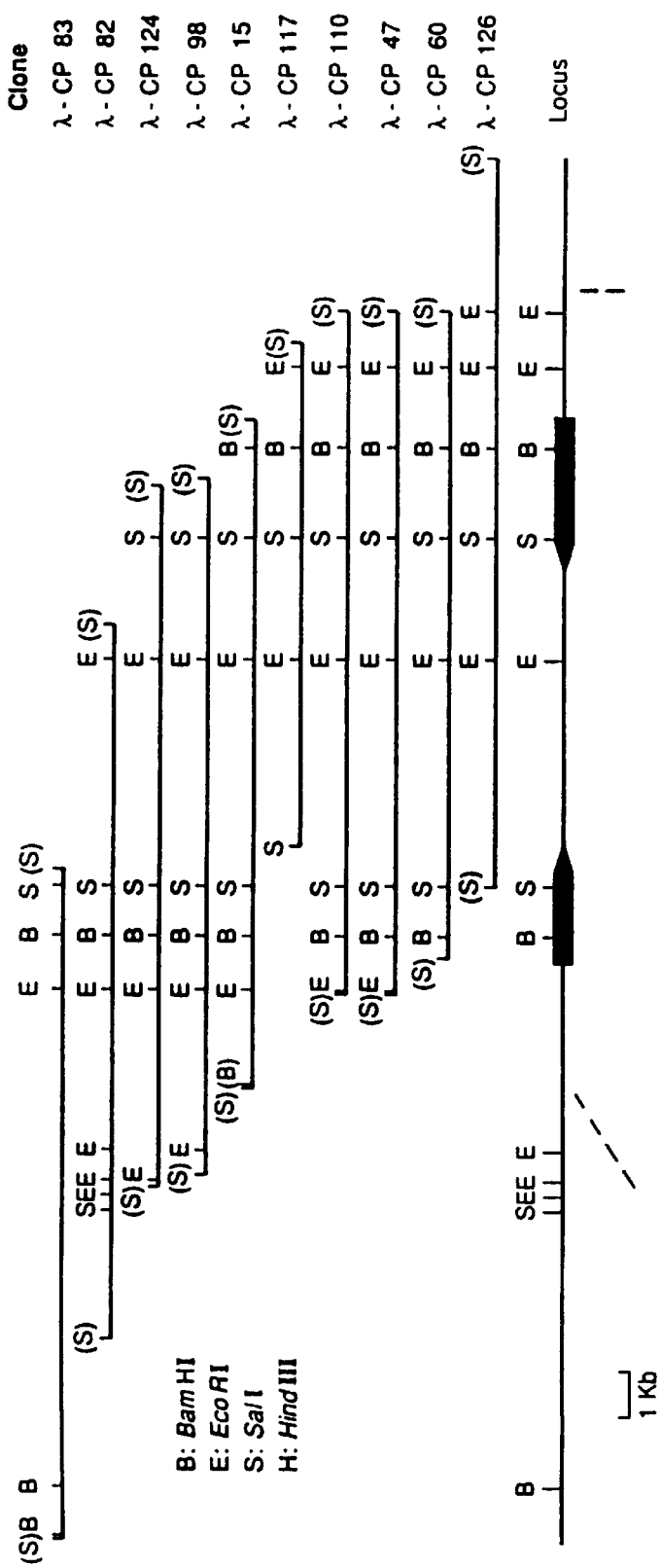
FIGS. 2A–2C show a restriction map of genomic clones obtained by hybridization to the cDNA encoding zucchini ACC synthase.
Figure 2B:
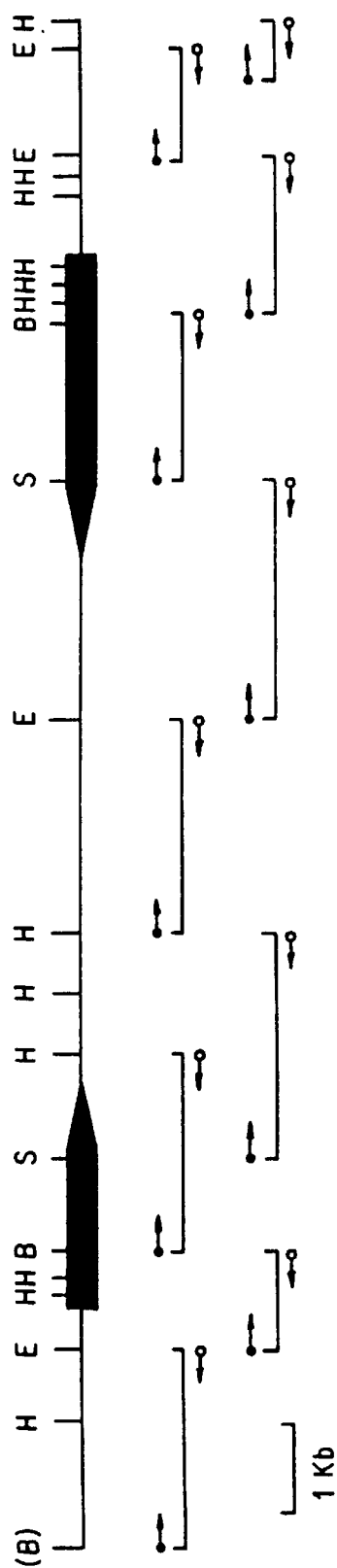
Figure 2C:
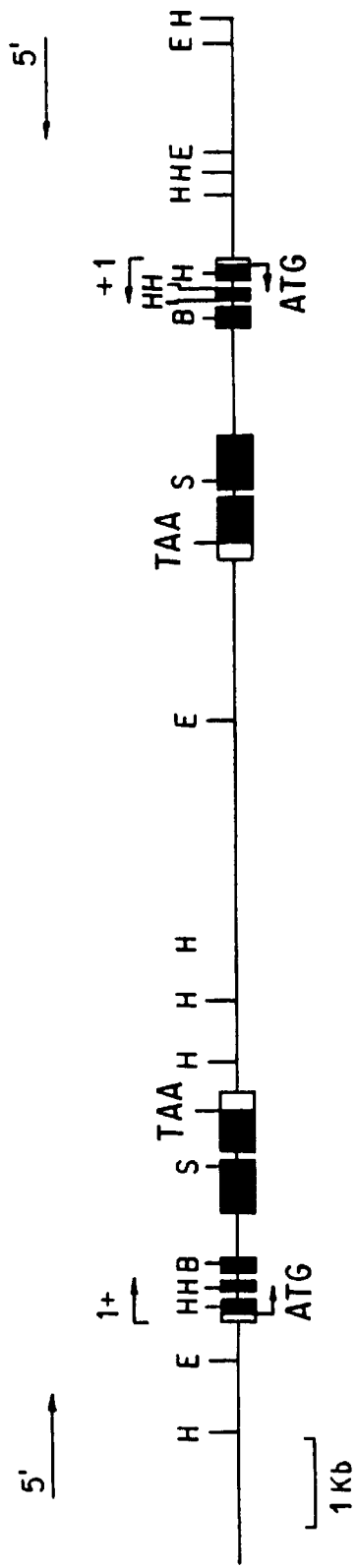

The results after restriction analysis of the various genomic clones recovered is shown in FIGS. 2A–C. As shown in the figure, two genomic clones reside on the same DNA strand, but are oriented in opposite directions. CP-ACC 1A and CP-ACC 1B each contain four introns. The complete genomic sequences of these clones are shown in FIGS. 3 and 4 respectively. As shown, the entire upstream regulatory sequences are included in the clones.

An alternative description for the isolation of the genomic sequences encoding ACC synthase in zucchini is set forth in Huang, P. L. et al., *Proc Natl Acad Sci USA* (1991) 88:7021–7025.

EXAMPLE 3

Retrieval of Tomato cDNA Encoding ACC Synthase

*Lycopersicon esculentum* c.v. Rutgers was grown from seeds throughout the year in a greenhouse using protocols to ensure freedom from tobacco mosaic virus. The fruit was frozen and total RNA was isolated from a ripe, wounded tomato fruit using the procedure of Chomczynski, P., et al. *Anal Biochem* (1987) 162:156–159. Approximately 5 gm of powdered frozen fruit tissue were used. Poly (A)$^+$ RNA was isolated using oligo (dT) cellulose chromatography as described by Theologis, A., et al. *J Mol Biol* (1985) 183:53–58, and a cDNA library was constructed into λgt10 as described by Huynh, T. V., et al. *cDNA Cloning Techniques: A Practical Approach* (1985) (Glover, D. M. ed.), IRL Press, London, 49–78. cDNAs greater than 500 bp were inserted into the EcoRI site of the C1 repressor gene. The packaged DNA was plated on C600 HFL, a derivative of C600, to select for phage-containing inserts.

Approximately $10^6$ plaque forming units of the λgt10 recombinant phage were plated to a density of $1 \times 10^4$ per 85 mm petri dish using C600. After transferring to nitrocellulose filters as described above, prehybridization and hybridization were performed at 37° C. with gentle agitation in 30% formamide, 5× SSPE (1× SSPE is 0.18M NaCl, 10 mM sodium phosphate, pH 7.0, 1 mM sodium EDTA), 5× BFP (1× BFP is 0.02% w/v bovine serum albumin, 0.02% polyvinyl pyrrolidone ($M_r$=360 kd), 0.02% Ficoll ($M_r$=400 kd), 100 mg/ml heat denatured salmon sperm DNA, and 0.1% SDS).

The gel purified 1.7 kb EcoRI fragment of the zucchini pACC1 prepared in Preparation A was labeled to a specific activity of $2 \times 10^8$ cpm/mg using random hexamer priming and α-32P dCTP as described by Feinberg, A. P., et al., *Anal Biochem* (1983) 132:6–13. The labeled probe was separated from starting material and used to probe the λgt10 library.

The probe was denatured with 0.25 volumes 1M NaOH for 10 minutes at room temperature and neutralized with 0.25 volume 2M Tris HCl, pH 7.2 and then added to the hybridization mixture at $1 \times 10^6$ cpm/ml.

After 24 hr hybridization, the filters were washed once in 30% formamide, 5× SSPE, 0.1% SDS at 37° C. for 20 min and then four times in 2× SSPE, 0.1% SDS at 37° C. for 20 min. The final wash was in 2× SSPE at 50° C. for 10 min.

After washing, the filters were air dried, covered with Saran wrap and exposed at −70° C. to X-ray film.

Using this hybridization, a full length cDNA encoding an ACC synthase from tomato was recovered and subcloned into the EcoRI site of pUC18 and was designated ptACC2. The complete cDNA sequence of the LE-ACC2 of tomato is shown in FIG. 5.

Figure 6:
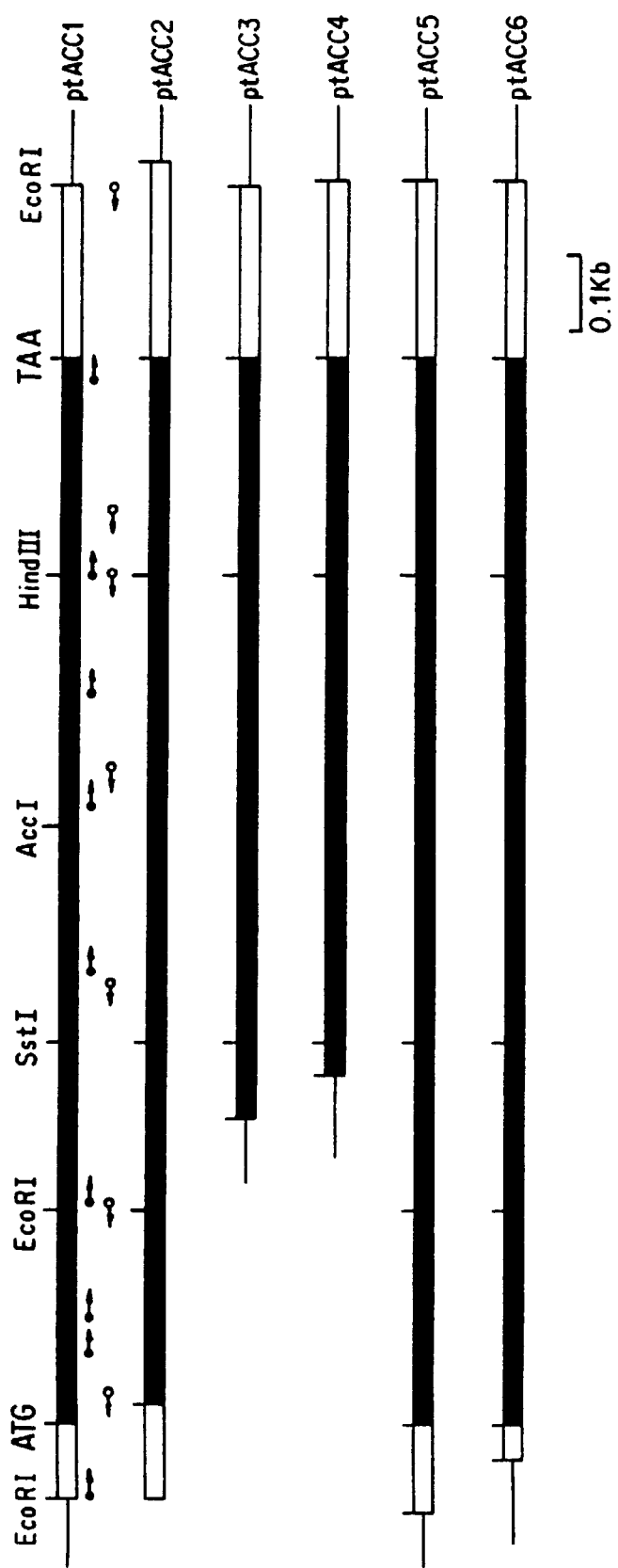
FIG. 6 shows a diagram and restriction map of several clones of the cDNA encoding tomato ACC synthase.

An additional clone was recovered using $2 \times 10^6$ cpm of the labeled 0.55 kb HindIII/EcoRI fragment at the 3' end of ptACC2. Hybridization conditions were employed using $2 \times 10^5$ pfu of the λgt10 library on C600 wherein nitrocellulose platelets were prehybridized at 42° C. and 50% formamide, 5× SSPE, 5× BFP, 500 mg/ml heat denatured salmon sperm DNA for 12 h. The filters were then hybridized for 18 hr at 42° C. with probe in 50% formamide, 5× SSPE, 1× BFP, 100 mg/ml heat denatured salmon sperm DNA with this probe. The filters were washed at 42° C. twice for 30 min in 50% formamide, 5× SSPE, 0.2% SDS, and then twice for 30 min in 0.1× SSPE at 42° C. Additional clones were retrieved using the above-referenced portion of ptACC2 as shown in FIG. 6.

A comparison of the amino acid sequences of the zucchini and tomato cDNA-encoded ACC synthases is shown in FIG. 10. As shown, considerable homology exists between these sequences, but they are not identical.

An alternative description of the retrieval of the insert of pt ACC2 and an additional clone designated ACC4 which is

EXAMPLE 4

Recovery of Tomato Genomic DNA Encoding ACC Synthase

Genomic DNA was isolated from etiolated *Lycopersicon esculentum* c.v. Rutgers seedlings using a modification of the method described by Davis, R. W., et al. *Meth Enzymol* (1980) 65:404–411. Briefly, seedlings were grown on moist filter paper in the dark for 5 days at 22° C. Fifty g frozen hypocotyl and cotyledon tissue, seed coat removed, was ground in a coffee grinder. The powdered tissue was added to 200 ml of ice cold extraction buffer (50 mM Tris-HCl, pH 8.0, 50 mM NaEDTA, 0.25 M NaCl, 15% sucrose (w/v)) and homogenized on ice using a hand held glass-glass homogenizer. The nuclei were pelleted at 2000×g for 10 min at 4° C. The crude nuclei were resuspended in 100 ml of cold extraction buffer without the salt. To lyse the nuclei, 10 ml of 10% "Nasarcosine" was added, the suspension was gently inverted and incubated on ice for 10 min, then 120 g of CsCl was added and dissolved by gently shaking. To remove debris the solution was centrifuged at 26,000×g for 20 min at 4° C. and the supernatant was decanted through "Miracloth".

Ethidium bromide (10 mg/ml) was added to a final concentration of 0.4 mg/ml and the density of the solution was adjusted to 1.55 g/ml. Equilibrium centrifugation was carried out in a Beckman Ti70 rotor at 40,000 rpm for 48 hr at 20° C. The DNA was further purified by a second round of equilibrium centrifugation in a VTi65 rotor at 50,000 rpm for 16 hr at 20° C. Ethidium bromide was extracted from the DNA with isopropanol saturated with water containing 5 M NaCl and the DNA was dialyzed twice against 5000 volumes of TE (pH 7.5) to remove the CsCl. The typical yield was 15 µg/g fresh weight tissue.

Two genomic libraries were constructed, one with 15–23 kb Sau3A partially digested DNA in λEMBL3 and another with 6–8 kb DNA after complete HindIII digestion into λ2001. For the library constructed in λEMBL3, 100 µg of genomic DNA was digested with 1.5 units of Sau3A at 37° C. in 300 µl of medium salt buffer (MSB) plus 2 mM dithiothreitol (DTT) (1× MSB is 10 mM Tris-HCl, pH 7.5, 50 mM NaCl, 10 mM MgSO$_4$). One third of the reaction was removed at 7.5 min, at 10 min and at 12.5 min. At each time point digestion was stopped by adding 0.1 volume 0.5 M NaEDTA, pH 8.0 and storing on ice. The DNA was size fractionated in a 0.5% low melting temperature agarose gel by electrophoresis at 0.8 volts/cm for 24 h. The agarose gel electrophoresis buffer was 1× TAE, 40 mM Tris-HOAc, pH 8.0, 2 mM NaEDTA. The gel was soaked at room temperature for 3 hr in 1× TAE buffer containing 0.3 M NaCl. DNA was visualized with 365 nm ultraviolet light and the 15–23 kb size range was excised. The agarose was melted at 65° C. for 15 min and extracted twice with TE (pH 7.5)-saturated phenol, prewarmed to 37° C. The aqueous phase was extracted three times with ether and two volumes of EtOH were added. After overnight at −20° C. the DNA was collected by centrifugation and dissolved in TE, pH 7.5. Two µg of EMBL3 arms and 2 µg size selected DNA were combined in a final volume of 6 µl, 1 µl of 10× ligase buffer (1× ligase buffer is 66 mM Tris-HCl, pH 7.5, 5 mM MgCl$_2$) was added and the cohesive ends annealed at 42° C. for 15 min. The mixture was quickly cooled on ice and 1 µl each of 10 mM ATP and 50 mM DTT was added. The reaction was initiated with 1 µl (8 units) of T4 DNA ligase and incubated overnight at 14° C. One third of the ligation mix was packaged with Gigapak Gold (Stratagene) according to the manufacturer. Approximately 1×10$^6$ pfu were obtained when titered on C600.

For the HindIII library, 200 µg of genomic DNA was digested in 3.6 ml 1× MSB with 400 units of enzyme for 4 hr at 37° C. The DNA was separated on a 0.8% low melting temperature agarose gel and DNA in the 6–8 kb size range was isolated as described above. One µg of this DNA was ligated to 0.5 µg of λ2001 arms as described above in a final volume of 10 µl. One third of this ligation was packaged with Gigapak Gold and 5×10$^4$ pfu were obtained when plated on K802.

A BglII complete digest library and an MboI partial digest library of genomic DNA from tomato cultivar VF36, both in EMBL4, were provided by C. Corr and B. Baker. These libraries and the HindIII complete digest library in λ2001 were plated on the host K802 and probed at high stringency with the ptACC1 cDNA as described above to obtain clones corresponding to the cDNA. Clones corresponding to other genes were obtained by probing the Sau3A partial digest library in EMBL3 with the cDNA at low stringency. In two separate screenings, phage were plated on the hosts C600 or TC410, lifted and fixed to nitrocellulose filters as described above. Low stringency prehybridization and hybridization were done in 30% formamide, 5× SSPE, 5× BFP, 100 µg/ml denatured salmon sperm DNA, 0.2% SDS at 37° C. for 18 h each. Probe was used at a concentration of 10$^6$ cpm/ml. Washing was done twice for 20 min in 30% formamide, 5× SSPE, 0.2% SDS at 37° C., and twice for 20 min in 2× SSPE, 0.2% SDS at 42° C. The filters were exposed to X-ray film as above for 48 h.

For restriction enzyme digestions of λ clones, 2.5 µg of phage DNA was digested in 50 µl of high salt buffer (HSB) (1× HSB is 100 mM NaCl, 50 mM Tris-HCl (pH 7.5), 10 mM MgSO$_4$) with the appropriate enzyme(s). For genomic DNA gel blots, 7.15 µg of genomic DNA was digested in 100 µl of 1× HSB with 80 units of EcoRI and HindIII or 40 units of BglII, at 37° C. for 6 h. Digested DNAs were loaded on 1 cm thick, 0.8% agarose gels and electrophoresed at 3 V/cm in 1× TAE buffer containing 0.5 µg/ml ethidium bromide. After electrophoresis the gel was photographed, the DNA was nicked with two 15 min treatments of 0.25 M HCl, denatured with two 20 min treatments of 0.5 M Tris-HCl (pH 7.5), 1.5 M NaCl and neutralized with two 20 min treatments of 0.5 M Tris-HCl (pH 7.5), 1.5 M NaCl. The nucleic acids were transferred in 20× SSPE to a Nytran nylon membrane.

After transfer was complete the nucleic acids were fixed with 1.2 joules of 254 nm ultraviolet radiation. The membranes were prehybridized in 50 ml of 50% formamide, 5× SSPE, 5× BFP, 1.0% SDS and 100 µg/ml heat denatured salmon sperm DNA at 42° C. for 12 h. Hybridizations were carried out in 30 ml of 50% formamide, 5× SSPE, 1× BFP, 10% dextran sulfate ($M_r$=400 kd), 0.2% SDS, and 50 µg/ml heat-denatured salmon sperm DNA at 42° C. for 18 h. Filters with genomic DNA were hybridized with 2.0×10$^6$ cpm/ml, whereas filters with λ DNA were hybridized with 5×10$^5$ cpm/ml of random hexamer labeled 1.8 kb ptACC1 cDNA. After hybridization the membranes were washed two times for 20 min at 55° C. in 0.1× SSPE and 0.2% SDS, dried, wrapped in plastic warp and placed under Kodak XR-5 X-ray film. λ DNA gel blots were exposed for 12–24 hr at −70° C. with an intensifier screen.

Figures 7A, 7B:
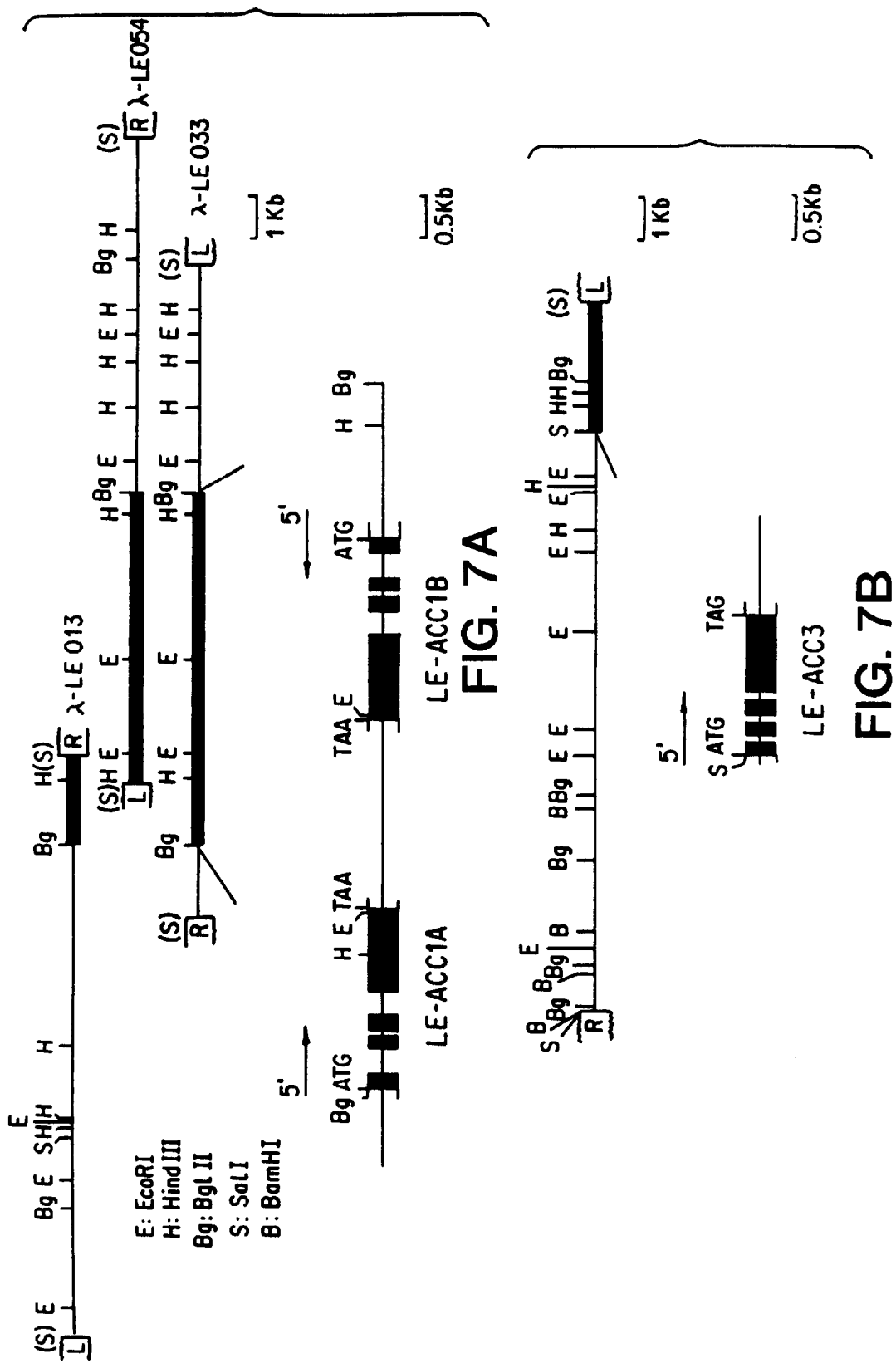
FIGS. 7A–7C show the restriction enzyme pattern of genomic clones and functional diagrams thereof for the tomato genome containing coding and control sequences for LE-ACC 1A, LE-ACC 1B, and LE-ACC 3.
Figure 7C:
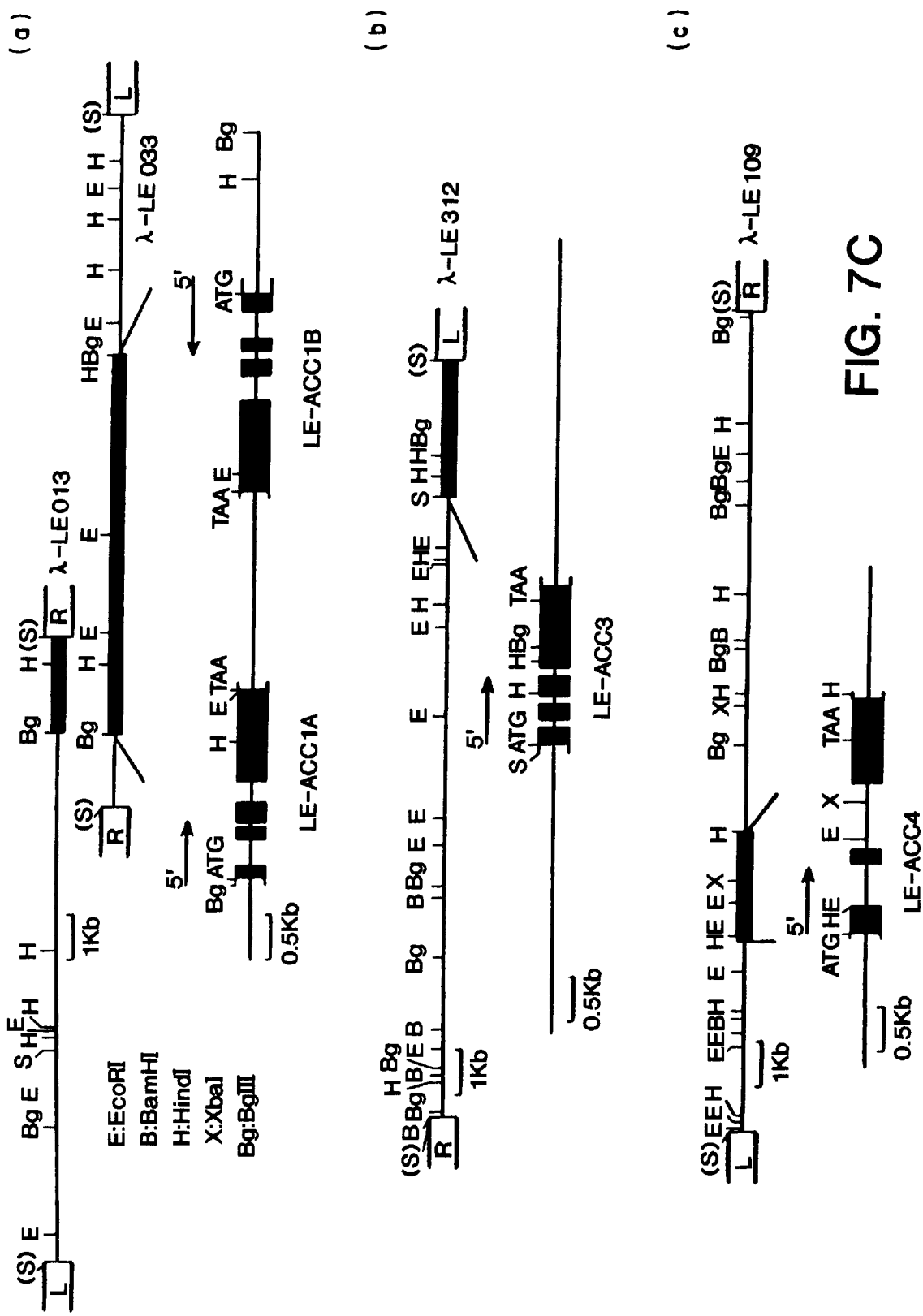
Figure 8:
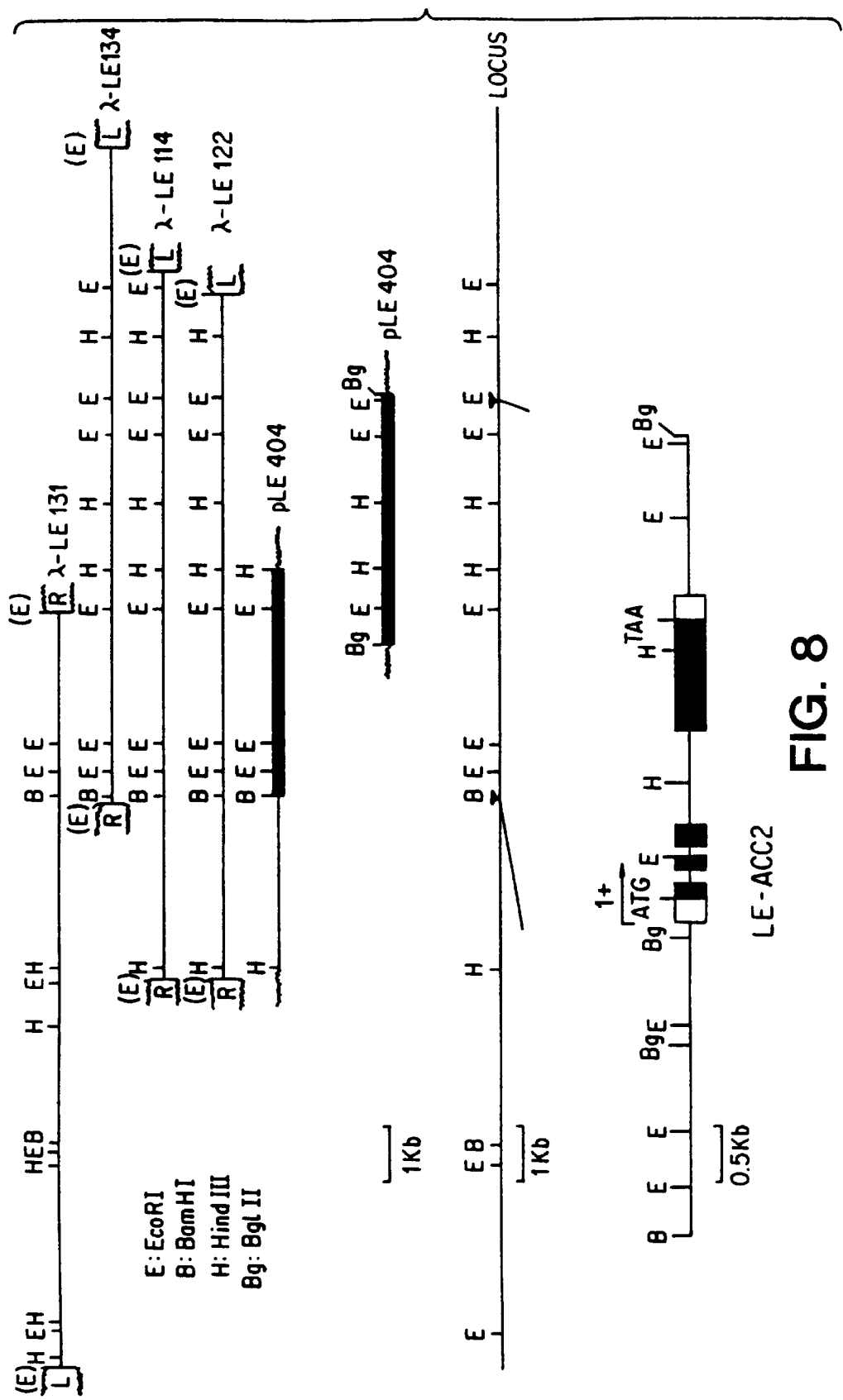
FIG. 8 shows the restriction enzyme pattern of genomic clones and the organization of the gene for LE-ACC 2.

The clones corresponding to five different genomic clones were recovered from tomato. A diagram of four of these is shown FIG. 7. FIG. 7A shows a series of two genomic clones which were identified to LE-ACC 1A and LE-ACC 1B; these genes are transcribed convergently. FIG. 7B shows a map of LE-ACC 3; FIG. 7C shows a map of Le-ACC 4. FIG. 8 shows a map of LE-ACC 2. FIG. 9 shows the complete nucleotide sequence of LE-ACC 2.

Table 1 shows a comparison of the properties of the ACC synthase peptides encoded by the genes known to encode this peptide in tomato and zucchini; FIG. 10 compares the amino acid sequences encoded by the seven genomic clones recovered—two from zucchini and five from tomato.

TABLE 1

| Gene | Amino acid no. | Predicted molecular mass (Da) | Isoelectric Point |
|---|---|---|---|
| CP-ACCIA | 493 | 55,779 | 6.84 |
| CP-ACCIB | 494 | 55,922 | 7.68 |
| LE-ACCIA | 485 | 54,809 | 5.94 |
| LE-ACCIB | 483 | 54,563 | 6.16 |
| LE-ACC2 | 485 | 54,662 | 7.71 |
| LE-ACC3 | 469 | 53,094 | 8.01 |
| LE-ACC4 | 476 | 53,509 | 5.40 |

Again, conserved sequences are found and there is considerable homology; however, there are numerous differences in sequence. This work is also described in Rottmann, W. H. et al., *J Mol Biol* (supra).

EXAMPLE 5

Expression of Zucchini and Tomato cDNA in *E. coli*

The pACC1 from zucchini was subcloned into the EcoRI site of the expression vector pKK223-3 (DeBoer, H. A., et al, *Proc Natl Acad Sci USA* (1983) 80:21–25) and introduced into *E. coli* strain JM107. Transformants were grown in LB medium in the presence of ampicillin (50 mg/ml) at 37° C. for 4 h. IPTG was added to 1 mM and the cultures were incubated for 2 hr at 37° C. ACC synthase activity and ACC formation were assayed. When the 1.7 kb EcoRI cDNA fragment was inserted into pKK2233-3 in the correct orientation and the transformed *E. coli* incubated as described above, ACC synthase activity was produced in the absence of IPTG at 20 nmol/h/mg protein and in presence of IPTG at 42 nmol/h/mg. ACC formation per 100 ml of culture was 2280 nmol without IPTG and 4070 nmol in the presence of IPTG. No ACC synthase activity or ACC production were observed when the 1–7 kb fragment was inserted in the opposite orientation.

Figure 11:
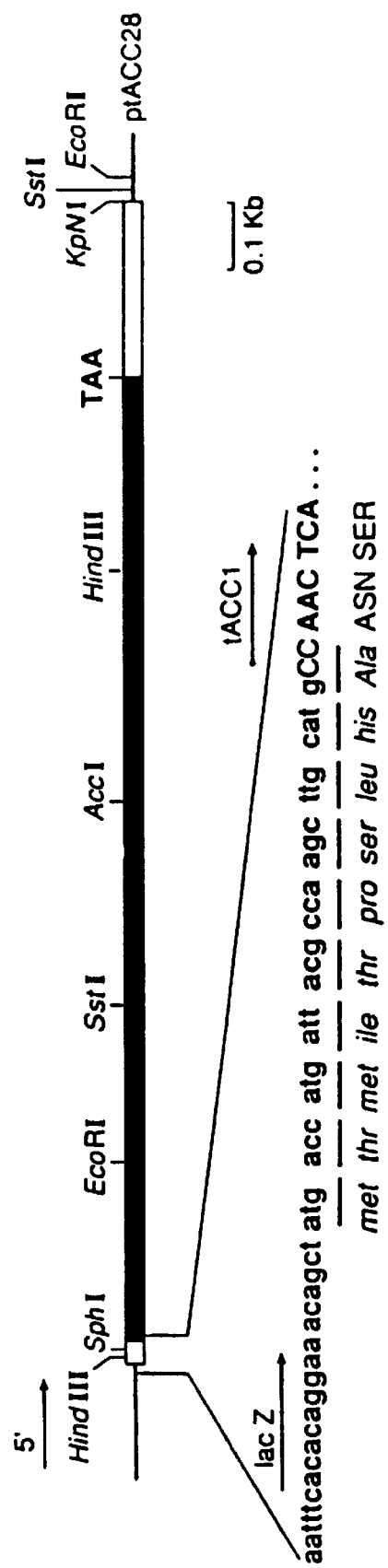
FIG. 11 shows the junction region and a restriction map of a bacterial expression vector for the production of tomato ACC synthase in bacteria.

A similar construct for tomato ACC synthase was used to test expression of the tomato cDNA in *E. coli*. The protein is synthesized as a fusion with a portion of the LacZ gene. The sequence at the junction is shown in FIG. 11.

For construction of the vector containing this junction, pETC3C (Rosenberg, A. H., et al. *Gene* (1987) 56:125–155) was modified by cutting with EcoRI and EcoRV and filling in with Klenow to remove a 375 bp fragment downstream of the T7 promoter. The resulting religated plasmid was named pPO7. pPO7 was cut with BamHI and NdeI and the large DNA segment was purified and ligated to a BamHI/NdeI polylinker containing an EcoRI site to obtain the intermediate plasmid pPO9.

Figure 15:
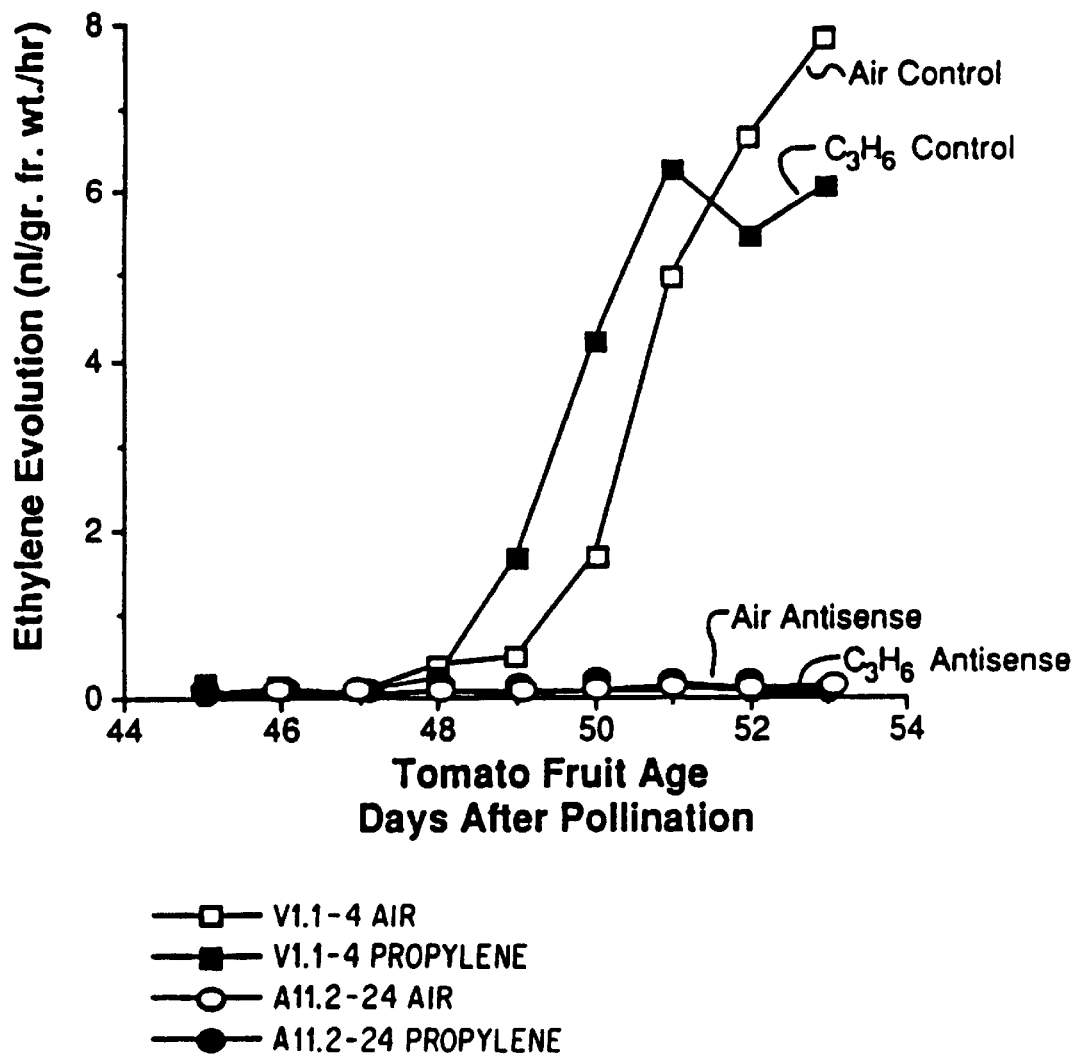
FIGS. 15 and 16 show the ethylene production by tomato plants regenerated from tomato cotyledons transformed with the vector of FIG. 14 as a function of days from pollination.

The 1.4 kb EcoRI fragment from ptACC2 was then ligated into the EcoRI site of pPO9 to obtain the junction shown in FIG. 15 and designated pPO46.

This plasmid was then used to transform *E. coli* BL21 (DE3) (Rosenberg et al. (supra)). The cultures were induced by diluting fresh overnight cultures into 2×TY (Maniatis et al. (supra)) and grown at 37° C. to an absorption at 600 nm of 0.7–0.8. IPTG was added to a final concentration of 2 mM and growth was continued for another two hours. The cells were harvested and the recombinant polypeptide was purified as described by Nagai, K. and Thogersen, A. C., *Meth Enzymol* (1987) 153:461–481.

Figure 12:
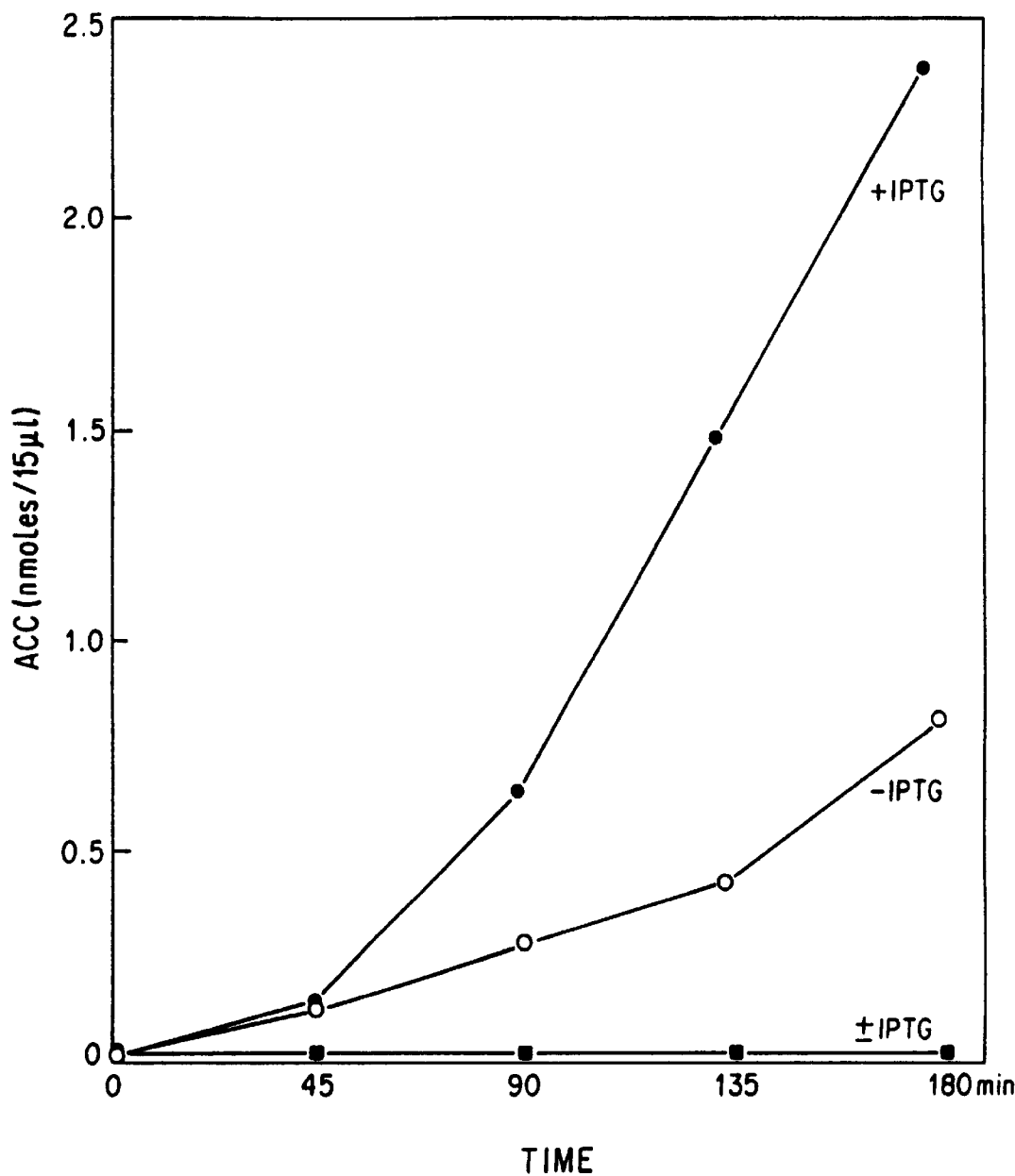
FIG. 12 shows the production of ACC by bacterial cultures transformed with the vector of FIG. 11 in the presence and absence of the inducer IPTG.

FIG. 12 shows the synthesis of ACC synthase in nmol/15 μl of culture transformed with the tomato ACC-containing vector in the presence and absence of IPTG. As shown in the figure, when the cDNA is ligated in the antisense direction, no ACC synthase is produced either in the presence or absence of IPTG (solid squares). When the cDNA is oriented in the correct orientation, after 180 min, over 2 nmol ACC synthase are produced per 15 μl in the presence of IPTG (solid circles), and between 0.5 and 1.0 nmol in the absence of IPTG (open circles).

Figures 13A, 13B, 13C:
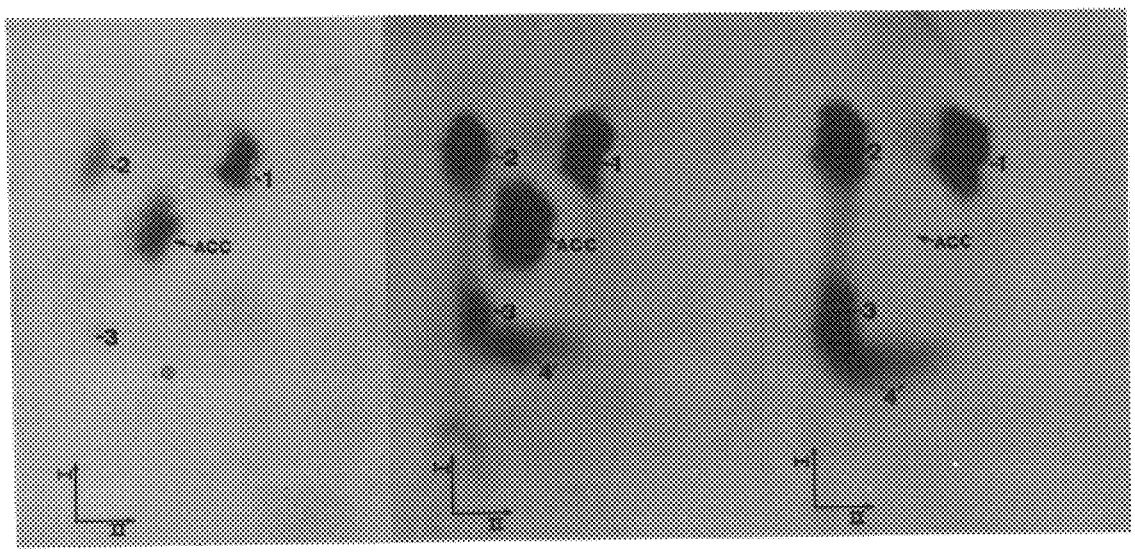
FIGS. 13A–13C are half-tone photographs of two-dimensional chromatographic gels of bacterial extracts wherein the bacterial culture is transformed with an expression vector for tomato ACC synthase having the coding sequence in the correct and incorrect orientations.

The production of ACC using labeled $C^{14}$-carboxyl-labeled S-adenosyl-methionine is shown in FIGS. 13A–13C. In these figures, #1 is methionine, #2 is methionyl sulfite, #3 is methionyl sulfoxide, and #4 is unidentified. ACC is clearly labeled. FIG. 13A shows the results in the absence of IPTG; a little ACC is formed. FIG. 13C shows the results when the cDNA is ligated in the wrong orientation; no ACC is formed. FIG. 13B shows the production of labeled ACC when the correct orientation of the cDNA is used. A large quantity of ACC is produced.

EXAMPLE 6

Expression of Zucchini ACC Synthase in Yeast

The EcoRI fragment representing cDNA clone ACC1 was subcloned into the EcoRI site of the yeast expression vector pBM258 (Johnston, M., et al. *Mol Cell Biol* (1984) 4:1440–1448) and introduced into yeast strain YM2061. The yeast cells were grown on YP medium (Sherman, F., et al., *Methods in Yeast Genetics* (1979) Cold Spring Harbor Laboratory, Cold Spring Harbor, N.Y.) at 37° C. for 24 hr. The medium either contained 2% galactose or 2% glucose. After this culture, the cells were harvested and the supernatant was assayed for ACC released into the medium. The pelleted cells were resuspended in buffer containing 5 gm glass beads and vortex-mixed 10 times for 30 sec and centrifuged at 2000×g for 3 min. This supernatant was also collected. Solid ammonium sulfate was added to achieve 80% saturation and the precipitate was collected and dissolved in 2 ml of 20 mM Tris-HCl, pH 8.0, 10 μM pyridoxal phosphate, 10 mM EDTA, 0.5 mM dithiothreitol; and dialyzed against the same buffer. No ACC was produced in medium containing 2% glucose regardless of the construction of the vector. Control host vector and control vector with the ACC1 cDNA inserted in the antisense direction also gave no production of ACC in the cellular extract. However, when the medium contained 2% galactose, the pBM-ACC1 vectors containing the cDNA in the correct orientation did show the production of ACC in the crude extract as well as ACC activity in the extracted protein. ACC synthase activity was 2.6 nmol/hr/mg protein in the crude extract; 354 nmol of ACC were formed per 100 ml of culture.

EXAMPLE 7

Antisense Inhibition of Ethylene Production in Tomato Plants

The ripening of tomatoes was shown to be preventable by the transformation of tomato plants with an antisense construction of the tomato ACC synthase gene which, therefore, putatively inhibited the synthesis of indigenous ACC synthase. The cDNA clone was inserted in the opposite sense direction under the control of the cauliflower CaMV 35S promoter and used to transform tomato plantlets using the *A. tumefaciens* mediated method. The regenerated plants produced tomatoes which failed to ripen, and which produced no ethylene at the times after pollination wherein ethylene was produced in control plants.

A detailed description of these results is set forth in Oeller, P. W. et al., *Science* (1991) 254:437–439, incorporated herein by reference.

The antisense vector was constructed as follows: the 35S promoter was obtained as a 302 bp fragment from pJO24D (Ow, D. W., *Proc Natl Acad Sci USA* (1987) 84:4870–4874). The plasmid pJO24D was digested with HindIII, treated with Klenow, and then cut with BamHI to isolate the 302 bp fragment using gel electrophoresis. This was ligated to 3.5 kb of tomato ACC synthase cDNA by excising the transcribed sequence from ptACC2, which includes cDNA of the LE-ACC2 gene, by digestion with XbaI, filling with Klenow, and then cutting with BamHI. The two BamHI fragments were ligated and the resulting ligation transformed into *E. coli* strain DH5A for cloning. The recovered plasmid was named pPO32.

The plasmid pPO32 was partially digested with SacI and SalI and the digest was ligated into SalI/SacI digested pBI101 binary Ti vector (Clonetech). pBI101 further contains the NOS 3' terminating sequences. The construct is shown in FIG. 14. The resultant vector, designated pPO35 was transformed into *E. coli* DH5A for cloning. The sequences at the junctions were verified by sequence analysis.

pPO35 or a control vector without the ACC-synthase gene was purified and introduced into Agrobacterium strain LBA4404 by a standard procedure described briefly as follows: *A. tumefaciens* LBA-4404 (2 ml) was grown overnight at 28° C. in LB broth, and this used to inoculate 50 ml of LB broth to obtain the desired culture. The inoculated medium was grown at 28° C. until the $OD_{600}$ was 0.5–1.0. The cells were collected by centrifugation and the pellet was resuspended in 1 ml, 20 mM ice cold $CaCl_2$. To 100 µl of the cell suspension, 1 µm of pPO35 DNA was added, and the mixture was incubated on ice for 30 min before snap-freezing in liquid nitrogen. The cells were then thawed at 37° C. for 5 min and used to inoculate 1 ml LB. After 2 h growth at 28° C. with agitation, 100 µl of the culture were plated on LB+Kan$_{50}$ medium; colonies appeared in 2–3 days at 28° C. The cells were recultured by picking several colonies and streaking on LB+Kan$_{50}$ medium; again, 3–4 colonies were picked from independent streaks and 5 ml cultures in LB+Kan$_{50}$ medium were grown. Stationary phase of these cultures were used for transfection of tomato plants. The cells can be frozen using 15% glycerol at −80° C. to store for later use.

Preparation of Host Plants

Tomato seeds were sterilized using a protocol which consisted of treatment with 70% ethanol for 2 min with mixing; followed by treatment with 10% sodium hypochlorite and 0.1% SDS for 10 min with mixing, followed by treatment with 1% sodium hypochlorite, 0.1% SDS for 30 min with mixing, and washing with sterile water 3× for 2 min each wash.

For germination, 0.8 g of the sterilized seeds were placed in a Seed Germination Medium in a filled magenta box and grown for 2 weeks at low light in a growth room. The magenta box contained 30 ml of the medium.[1]

[1] Seed Germination Medium contains, per liter, 2.16 g of Murashige-Skoog salts; 2 ml of 500× B5 vitamins which had been stored at 20° C., 30 g sucrose and 980 ml water, brought to 1 N KOH and containing 8 g agar. The medium is autoclaved in 500 ml portions before filling the magenta boxes.

After two weeks, when the seeds had germinated, cotyledons were dissected from the seedlings by cutting off the cotyledon tips and then cutting off the stem. This process was conducted in a large petri dish containing 5–10 ml of MSO.[2]

[2] MSO contains per liter 4.3 g of Murashige-Skoog salts, 2 ml of 500× B5 vitamins; 30 g of sucrose and 980 ml of water made 1 N in KOH to a final pH of 5.8.

The harvested cotyledons were placed abaxial side up in tobacco feeder plates and grown for 48 h.

The feeder plates were prepared from a tobacco cell suspension in liquid medium[3] at 25° C. prepared with shaking at 130–150 rpm. The suspension was transferred to fresh medium at 1:10 dilution per every 3–5 days. 1 ml of rapidly dividing culture was placed on the feeder plate, overlaid with filter paper and placed in low light in a growth room. The feeder plates were supplemented with 10 ml Feeder Medium.[4] The Agrobacterium containing the pPO35 vector was inoculated into 50 ml LB containing kanamycin with a single colony of the strain. The culture was grown shaking vigorously at 30° C. to saturation (OD>2.0 at 600 nm). The strain was chosen to come to full growth in less than 24 h. The culture was then diluted to $5 \times 10^8$ cell/ml with MSO and split into 50 ml portions in plastic tubes.

[3] Tobacco Suspension Medium contains in 1 liter 4.3 g Murashige-Skoog salts, 2 ml of 500× B5 vitamins, 30 g 3% sucrose, 10 µl of a 0.5 mg/ml solution of kinetin stored at −20° C., 2 ml of a 2 mg/ml solution of pCPA, and 980 ml of water made 1 N in KOH for a pH of 5.8 and autoclaved in 50 ml portions per 250 ml flask.

[4] Feeder Medium contains 0.43 g Murashige-Skoog salts, 2 ml 500× B5 vitamins, 30 g of sucrose and 980 ml water made 1 N in KOH to a pH of 5.8, including 0.8% agar. The foregoing components are autoclaved in two 500 ml portions and hormones are added when pouring plates to obtain 1 µg/ml benzyl adenine (BA) and 0.2 µg/ml of indole acetic acid (IAA).

Cotyledons from two of the feeder plates were scraped into each tube and rocked gently for 10–30 min. The cotyledons were then removed from the bacterial culture into sterile filter paper abaxial side up on a tobacco feeder plate and incubated for 48 h in low light in a growth room.

The cotyledons were then transferred axial side up to Callus Inducing Medium.[5]

[5] Callus Inducing Medium contains per liter 4.3 g of Murashige-Skoog salts, 2 ml of 500× B5 vitamins, 30 g of sucrose and 980 ml of water brought to 1 N KOH at a pH of 5.8. The medium contains 0.8% agar and is autoclaved in two 500 ml portions. When poured into the plates, the following hormones are added to the following concentrations: 1 µm/ml BA, 0.2 µg/ml IAA, 100 µg/ml kanamycin, 500 µg/ml carbenicillin (Geopen).

In the Callus Inducing Medium, approximately four plates were used per magenta box, and the explants were crowded. The box was placed in a growth room for three weeks, and small masses of callus formed at the surface of the cotyledons. The explants were transferred to fresh plates containing the callus inducing medium every three weeks.

When the calli exceeded 2 ml, they were transferred to plates containing shoot inducing medium.[6]

[6] Shoot Inducing Medium contains, per liter, 4.3 g of Murashige-Skoog salts, 2 ml of 500× B5 vitamins, 0.6 g of MES and 900 ml of water made 1 N in KOH for a pH of 5.8, and 0.8% agar. The medium is autoclaved in two 450 ml portions and then is added 100 ml of a 30% filtered, sterilized glucose solution. When the plates are poured, additional components are added as follows: 0.1 mg/ml zeatin, 100 μg/ml kanamycin, 500 μg/ml carbenicillin.

When the stem structure was evident, the shoots were dissected from the calli and the shoots were transferred to root inducing medium-containing plates.[7]

[7] Root Inducing Medium contains, per liter, 4.3 g Murashige-Skoog salts, 2 ml 500× B5 vitamins, 30 g of sucrose and 980 ml of water, 1 N in KOH to a pH of 5.8 in 0/8% agar. The medium is autoclaved in two 500 ml portions and when pouring plates, hormones are added to a concentration of 100 μg/ml kanamycin and 500 μg/ml or carbenicillin.

After a vigorous root system was formed on the plants, the plantlets were transferred to soil. To do this, they were taken from the plates, removing as much agar as possible and placed in a high peat content soil in a small peat pot which fits into a magenta box with cover. When the seedling leaves reached the top of the box, the lid was loosened and continued to be uncovered slowly over a period of 4–5 days. The plants were then transferred to a light cart and larger pots, and kept moist.

Figure 16:
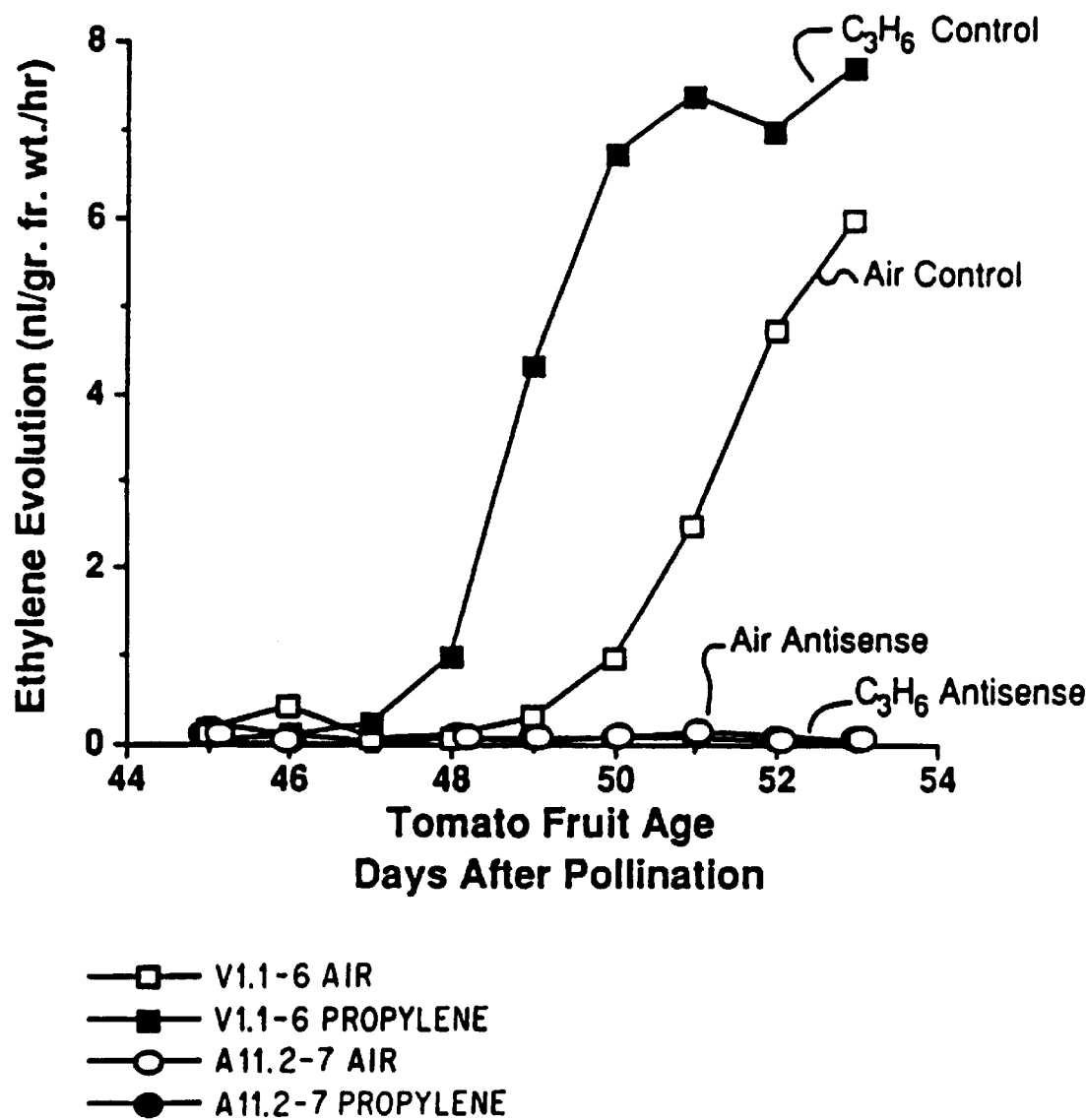

Flowers of these regenerated plants were pollinated and tomatoes were developed and ethylene measured by gas chromatography at specified days after pollination. FIGS. 15 and 16 show the results for two sets of individual plants V1.1–4 (which contains the control vector) and A11.2–24 (which contains the antisense vector) in FIG. 15 and V1.1–6 (which contains the control vector) and A11.2–7 (which contains the antisense vector) in FIG. 16. As shown in these figures, in both cases, the control plants which had been transformed with control vector produced high levels of ethylene up to 8 ng/g fruit/h after approximately 50 days after pollination either in the presence of propylene or in the presence of air. However, in both cases, there was no production of ethylene in those regenerated plants which had been transformed with the antisense pPO35 vector. In addition, the tomatoes which failed to produce ethylene also failed to ripen, whereas the control plants did ripen at this time.

Of 34 of the regenerated independent transgenic tomato plants obtained, three showed a marked inhibition of ethylene production and a delay in the onset of fruit ripening. The strongest phenotype was that of A11.1 which was chosen for further analysis with homozygous fruits from the second or third generation of the transgenic plants.

Southern Blot analysis showed that A11.1 plants obtained from seeds of the regerated plants contained an additional 1.7 kb DNA fragment that segregated as a single locus (3:1 ratio). A comparison of the hybridization intensities between the endogenous single copy LE-ACC2 synthase gene and the antisense gene indicates the presence of 10 antisense insertions per plant.

While control fruits kept in air begin to produce ethylene 48–50 days after pollination and then undergo a respiratory burst and fully ripen after 10 more days, ethylene production was inhibited by 99.5% in the fruits of A11.1 and these fruits failed to ripen. The antisense A11.1 fruits have a basal level of ethylene evolution of less than 0.31 nanoliters per gram of fruit; the red coloration resulting from chlorophyll degradation and lycopine biosynthesis is also inhibited and a progressive loss of chlorophyll from antisense fruits is seen 10–20 days later than the losses seen in control fruits, resulting in a yellow color. The antisense fruits kept in air or on the plants for 90–120 days eventually develop an orange color but never turn red and soft or develop an aroma. Antisense fruits in air do not show the respiratory burst even when they are 95 days old. Treatment with propylene or ethylene, however, induced ripening in the antisense plants but did not induce endogenous ethylene production. This treatment did induce the respiratory rise. Propylene or ethylene-ripened antisense fruits are indistinguishable from the naturally ripened fruits with respect to texture, color, aroma and compressibility.

Mature 57-day old green antisense fruits express ACC2 antisense RNA, whereas control fruits do not. Treatment with air or propylene for 14 days does not alter the amount of antisense RNA. The expression of mRNAs from both ripening induced ACC synthase genes LE-ACC2 and LE-ACC4 is inhibited in antisense fruits treated with air or propylene.

The expression of two other genes, TOM13 and polygalacturonase (PG) (Hamilton, A. J., *Nature* (1990) 346:284; de la Pena, D. et al., *Proc Natl Acad Sci USA* (1986) 83:6420) was also analyzed.

U.S. Pat. No. 4,801,540 describes and claims the isolated PG-encoding gene. Giovannoni, J. J., et al., *The Plant Cell* (1989) 1:53–63, describes the expression of a chimeric PG gene in rin tomato fruits which results in polyuronide degradation but not fruit softening.

TOM13 mRNA is first detected in control fruits at about 48 days before ACC synthase mRNA is detectable and expression remains the same in air or propylene-treated control fruits. In antisense fruits, TOM13 and PG mRNA expression is similar to that in control fruits, demonstrating that expression of both genes during ripening is ethylene-independent.

It has been shown by others that antisense RNA to PG does not prevent tomato fruit ripening and expression of PG polypeptide in the tomato ripening mutant rin does not result in fruit softening.

To induce ripening in the antisense fruits, mature green fruits 49 days old from control and antisense plants were treated with ethylene for 1, 2, or 15 days. While antisense fruits treated for 1–2 days with ethylene did not develop a fully ripe phenotype, antisense fruits treated for 15 days with ethylene ripen normally. After 7 days of treatment, the fruits become fully red and soft. It was found that the ripening process requires continuous transcription of the necessary genes since ethylene treatment for one or two days was not sufficient. This may reflect a short half-life of the induced mRNAs or polypeptides. It is known that the half-life of the ACC synthase polypeptide is about 25 minutes (Kende, H. et al., *Plata* (1981) 151:476; Yoshi, H. et al., *Plant Cell Physiol* (1982) 23:639).

It should be noted that two other enzymes associated with tomato ripening have been used to construct antisense RNA-generating vectors which are unsuccessful in retarding the ripening of fruit (Hamilton, A. J. et al., *Nature* (1990) 346:284, cited above, and Smith, C. J. S., *Nature* (1988) 334:724). Thus, the association of the product of a gene with a ripening process does not lead to an expectation that the repression of the expression of that gene will impair ripening.

EXAMPLE 8

Purification of Native ACC Synthase from Cucurbita

ACC synthase was purified 6000-fold from induced Cucurbita homogenates according to a multistep protocol as shown below. Various buffers used in the purification are as follows:

Buffer A: Tris-HCl 100 mM, pH 8.0, EDTA 20 mM, pyridoxal phosphate 10 $\mu$M, PMSF 0.5 mM, β-mercaptoethanol 20 mM; Buffer B: Tris-HCl 20 mM, pH 8.0, EDTA 10 mM, pyridoxal phosphate 10 $\mu$M, DTT 0.5 mM; Buffer C: Na-acetate 20 mM, pH 6.0, pyridoxal phosphate 10 $\mu$M, EDTA 10 mM, DTT 0.5 mM; Buffer D: K-phosphate 10 mM, pH 8.0, pyridoxal phosphate 10 $\mu$M, EDTA 1 mM, DTT 0.5 mm; Buffer E: Tris-HCl 20 mM, pH 8.0, pyridoxal phosphate 5 $\mu$M, EDTA 1 mM, DTT 0.5 mM; Buffer F: Hepes-KOH 500 mM, pH 8.5, pyridoxal phosphate 40 $\mu$M, BSA 400 $\mu$g/ml.

All operations were performed at 4° C. Chromatographic elutions were assayed for ACC synthase activity and by absorption at 280 nm.

Ten kg of Cucurbita slices incubated for 24 hr in induction medium were chilled with liquid $N_2$ and homogenized in batches of 2 kg with 2 liters of buffer A plus 200 g of polyvinylpolypyrrolidone in a one gallon Waring® blender for 1 min at medium speed. The homogenate was centrifuged at 17,000×g for 30 min. The supernatant was filtered through one layer of Miracloth® and one layer of nylon cloth (30 $\mu$m mesh).

Butyl Toyopearl Fractionation-1

Solid ammonium sulfate was added slowly to the stirred supernatant above to achieve 40% saturation. The supernatant solution was stirred for 15 min and 300 ml of packed Butyl Toyopearl 650 M hydrophobic affinity matrix, previously equilibrated with buffer B saturated to 40% with ammonium sulfate, were added. The suspension was occasionally stirred for an additional 30 min. The matrix was recovered by filtration through one layer of nitex nylon cloth (30 $\mu$m mesh) and the solution was squeezed out by hand. Subsequently, the matrix was placed in a vacuum filter with two sheets of Whatman® filter paper #1 and washed with 500 ml of buffer B containing 40% ammonium sulfate. The adsorbed proteins were eluted from the matrix by washing (twice) with 750 ml of buffer B, batchwise. The combined eluates were dialyzed three times against 10 liters of buffer B for 36 hr.

SP-Sephadex® Fractionation

The dialyzed fraction above was clarified by centrifugation at 17,000×g for 30 min. The volume was adjusted to 4 liters with buffer B and the pH was brought to pH 6.0 with 5% acetic acid. Two liters of packed SP-Sephadex® C-50 equilibrated with buffer C were added and the suspension was stirred for 60 min. The matrix was recovered by filtration through two sheets of Whatman® filter paper #1 and washed with 2 liters of buffer C. The adsorbed proteins were eluted twice with 1 liter of buffer B containing 1M KCl, batchwise. The eluant was recovered by suction through #1 Whatman® filter paper and solid ammonium sulfate was added to achieve 40% saturation. Subsequently 100 ml of Butyl Toyopearl-packed matrix equilibrated with buffer B/40% ammonium sulfate was added to the eluate. The suspension was stirred for 30 min and the matrix was collected by filtration through a layer of Nitrex® nylon cloth (30 $\mu$m mesh). The matrix was resuspended in a small volume of buffer B/40% ammonium sulfate and poured in a column (2.5×20 cm). The adsorbed proteins were eluted with buffer B, and the flow rate of the column was under gravity. Fractions with high $A_{280}$ were pooled and dialyzed overnight against 4 liters buffer B with three buffer changes during the course of dialysis.

QAE-Sephadex® Fractionation

Four hundred ml of packed QAE-Sephadex® equilibrated with buffer B were added to the dialyzate from the SP-Sephadex® fractionation and the suspension was stirred gently for 60 min. The matrix was recovered by filtration through a layer of Miracloth® in a filtration apparatus and washed with 500 ml of buffer B to remove unadsorbed proteins. The matrix was resuspended in a small volume of buffer B and poured into a column (4×30 cm). The proteins were eluted with buffer B containing 0.2M KCl.

Butyl Toyopearl Chromatography-2

Solid ammonium sulfate was added to the eluate (~100 ml) to achieve 40% saturation and the solution was kept at 4° C. for at least 4 hr. The suspension was centrifuged at 30,000×g for 30 min and the supernatant was applied on a Butyl Toyopearl column (1.5×14 cm) equilibrated with buffer B/40% ammonium sulfate. After all the protein solution was passed through the column, it was eluted with a 400 ml linear gradient: 40 to 0% ammonium sulfate in buffer B with a flow rate of 1 ml/min.

Figure 17A:
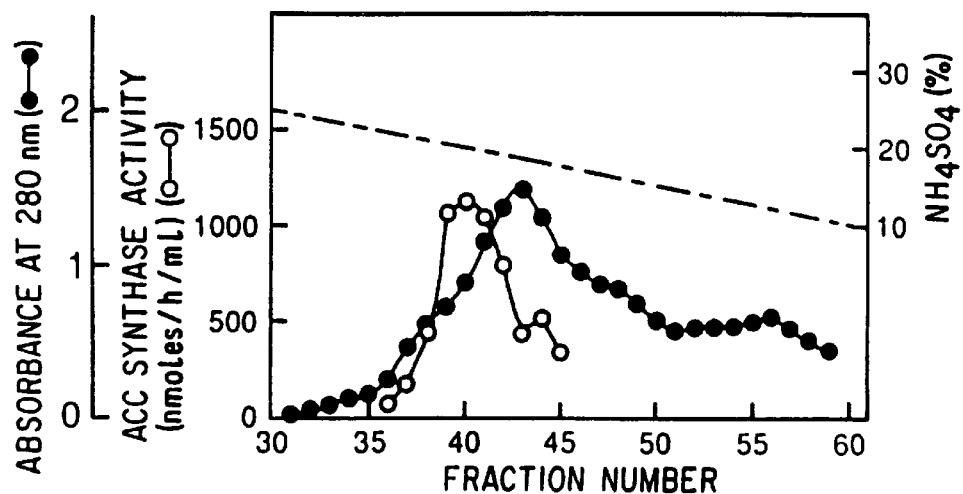
FIGS. 17A–17C show the elution patterns obtained in the purification of ACC synthase from zucchini using butyl Toyopearl chromatography, Sephacryl S-300 chromatography, and BioGel HT chromatography, respectively.

FIG. 17A shows the elution pattern. Solid ammonium sulfate was added to enzymatically active fractions to achieve 80% saturation and the solution was incubated at 4° C. for at least 4 hr. The precipitate was collected by centrifugation at 30,000×g for 30 min at 4° C. and dissolved in 3 ml of buffer D.

Sephacryl S-300 Chromatography

Figure 17B:
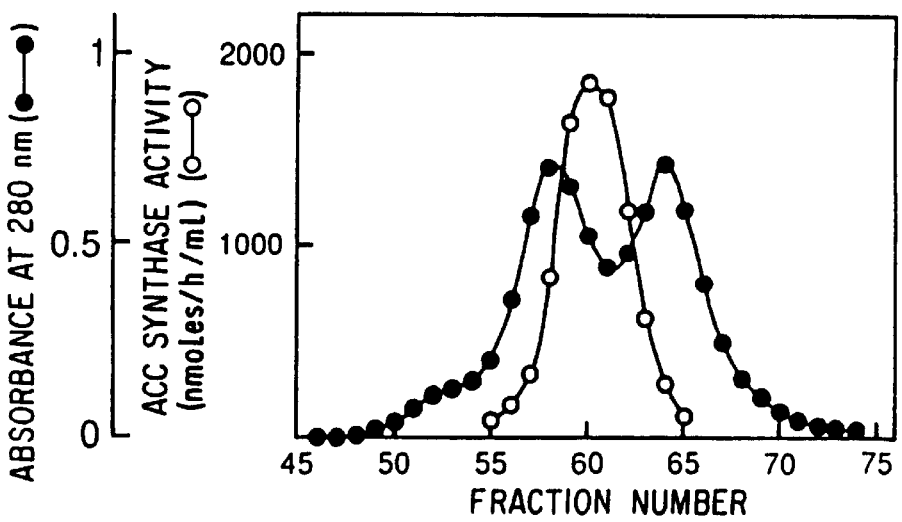

The resulting protein solution from above was applied to a column (2.5×100 cm) of Sephacryl S-300 equilibrated with buffer D. The column was eluted with buffer D at a flow rate of 0.5 ml/min. FIG. 17B shows the elution pattern.

Bio Gel-HT® Chromatography

Figure 17C:
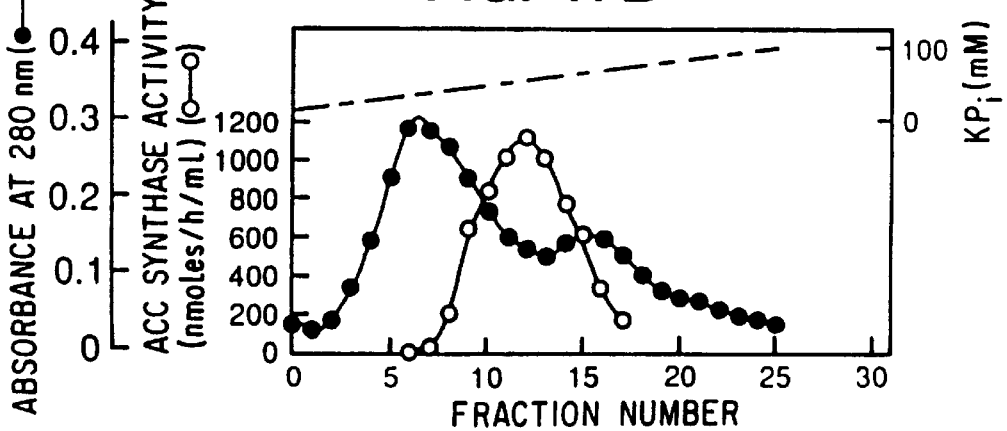

Active fractions from the Sephacryl step were combined and applied on a Bio Gel-HA column (0.75×14 cm) equilibrated with buffer D. The column was washed with buffer D until $A_{280}=0$ and it was then eluted with a 200 ml linear gradient: 10–100 mM potassium phosphate in buffer D with a flow rate of 0.1 ml/min. FIG. 17C shows the elution pattern. The active fractions were collected and concentrated with a Centricon 30 filtration apparatus, concomitantly the buffer of the concentrated protein solution was changed to buffer E.

FPLC Mono-Q Chromatography

Figure 18:
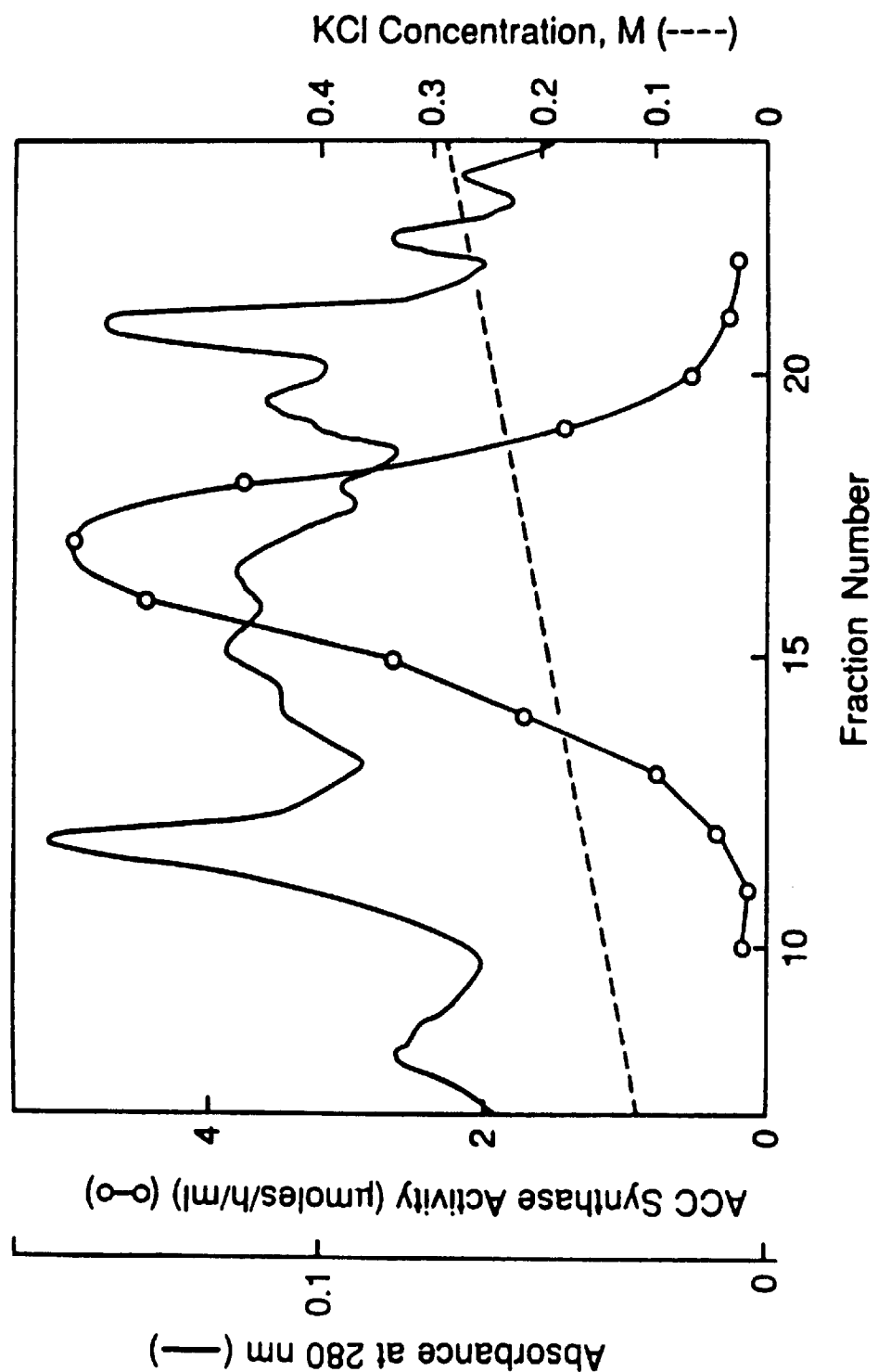
FIG. 18 shows the elution pattern obtained with FPLC Mono-Q chromatography.

The concentrated active fractions (~0.5 ml) from the Bio Gel-HT® column were applied to a mono-Q HS/5 column. The column was washed with buffer E containing 0.1M KCl until $A_{280}=0$. The column then was eluted with a 15 ml linear gradient: 0.1 to 0.4M KCl in buffer E. The flow rate of the gradient was 0.5 ml/min. FIG. 18 shows the elution pattern.

Table 2 shows the overall purification sequence and the increase in specific activity with each successive step. The overall process results in a 6000-fold purification with a recovery of 7.5w. The enzyme has a specific activity of 35,590 nmol ACC produced/hr/mg of protein.

TABLE 2

Partial Purification of ACC Synthase from Cucurbita Tissue Slices[a,b]

| Step | | Total Protein (mg) | Total Activity (nmol/h) | Specific Activity (nmol/h/mg protein) | Fold Purification | Recovery (%) |
|---|---|---|---|---|---|---|
| 1. | Crude Extract | 17,600 | 105,000 | 6 | 1 | 100 |
| 2. | Butyl Toyopearl 650M | 8,000 | 120,000 | 15 | 2.5 | 115 |
| 3. | SP-Sephadex ® | 800 | 49,000 | 62 | 10.4 | 47 |
| 4. | QAE-Sephadex ® | 336 | 45,800 | 136 | 23 | 44 |
| 5. | Butyl Toyopearl 650M | 67 | 13,500 | 201 | 34 | 13 |
| 6. | Sephacryl S-300 | 22 | 28,300 | 1,286 | 214 | 27 |
| 7. | Bio Gel-HT ® | 2.2 | 20,230 | 9,195 | 1,550 | 19 |
| 8. | Mono-Q | 0.22 | 7,830 | 35,590 | 6,000 | 7.5 |

[a]Amount of tissue: 10 kg
[b]Tissue treatment: IAA 0.5 mM + BA 0.1 mM + LiCl 50 mM + AOA 1 mM for 24 hr.

Figure 19:
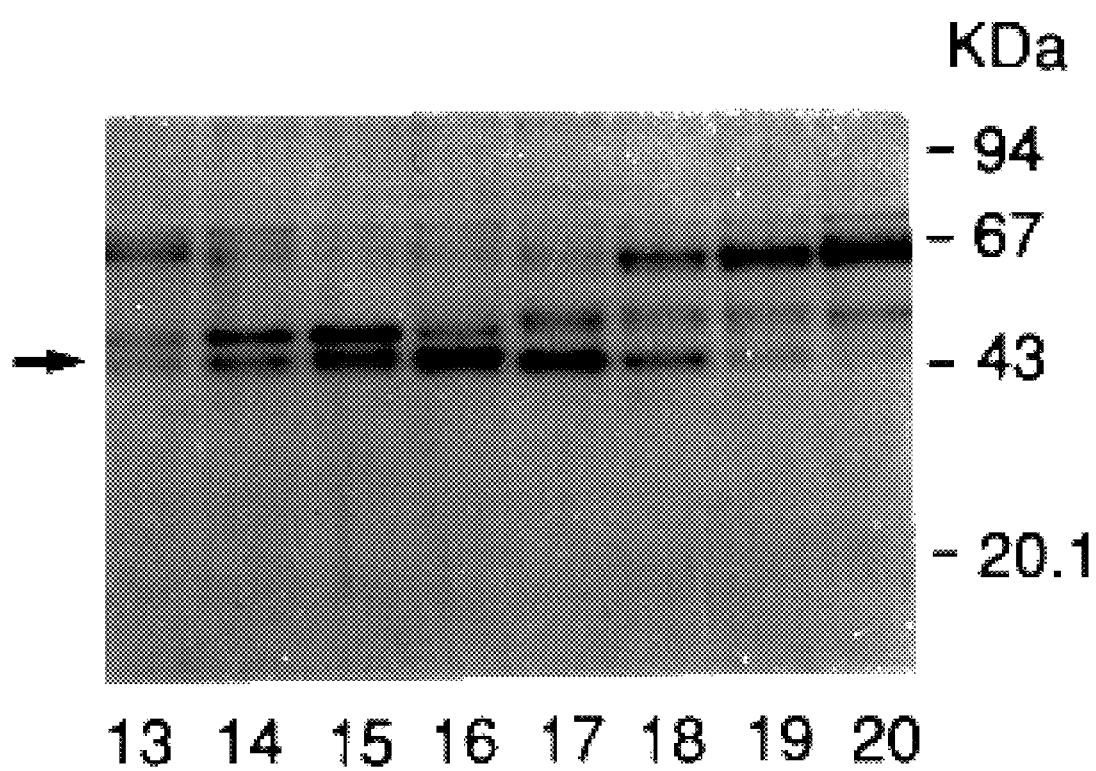
FIG. 19 is a halftone photograph showing the results of SDS-PAGE conducted on fractions obtained from the Mono-Q column of FIG. 18.

SDS-PAGE conducted on fractions 16 and 17 from the mono Q column, which have the highest ACC synthase activity, indicated that the protein was not completely pure. (See FIG. 19.) However, it was demonstrated that the ACC synthase activity resided in the 46 kd band. The electrophoresis was conducted by applying 7.5 ml of the eluted fractions mixed with an equal volume of 2× SDS loading buffer to a 10% polyacrylamide gel and silver staining. To determine the band containing ACC synthase activity, similar gels were run wherein the gels were cut into 3 mm thick slices and the ACC synthase activity was determined in half the slices; the other half were stained with silver.

The purified ACC synthase was also subjected to size exclusion chromatography on Sephacryl S-300. In this protocol, the ACC synthase eluted as an 86 kd species. This suggests that the Cucurbita ACC synthase consists of two identical 46 kd subunits. Further characterization showed that the pH optimum for ACC synthase activity is 9.5, and the isoelectric point is estimated at 5 using mono-P H 5/20 FPLC column chromatography. The Km for AdoMet is 16.7 mM, and pyridoxal phosphate is a cofactor. The enzyme is stable at −20° C. or −80° C. for over a year.

What is claimed is:

1. An isolated DNA molecule capable of encoding an amino acid sequence selected from the group consisting of SEQ ID NO:25, SEQ ID NO:27, and SEQ ID NO:32.

2. An isolated DNA molecule which comprises a nucleotide sequence encoding the amino acid sequence of the ACC synthase designated herein LE-ACC2.

3. A DNA molecule which comprises an expression system for the production of the ACC synthase LE-ACC2, which expression system comprises a nucleotide sequence encoding said ACC synthase operably linked to control sequences capable of effecting its expression.

4. A recombinant host cell modified to contain the DNA molecule of claim 3.

5. The host cell of claim 4 which is a plant cell.

6. A plant, plant part or plant cell modified to contain the DNA molecule of claim 3.

7. A method to produce ACC synthase LE-ACC2 which method comprises culturing the cell of claim 4 under conditions wherein said ACC synthase is produced and recovering said ACC synthase.

8. A method to produce ACC synthase LE-ACC2 which method comprises culturing the plant of claim 6 under conditions wherein said ACC synthase is produced and recovering said ACC synthase.

* * * * *